US008883766B2

(12) United States Patent
Martinborough et al.

(10) Patent No.: US 8,883,766 B2
(45) Date of Patent: Nov. 11, 2014

(54) ION CHANNEL MODULATORS AND METHODS OF USE

(75) Inventors: Esther Martinborough, San Diego, CA (US); Tim Neubert, San Diego, CA (US); Tara Whitney, Carlsbad, CA (US); Danielle Lehsten, Fayetteville, WV (US); Tara Hampton, Fort Worth, TX (US); Nicole Zimmermann, San Diego, CA (US); Andreas P. Termin, Encinitas (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/457,855

(22) Filed: Apr. 27, 2012

(65) Prior Publication Data

US 2012/0208790 A1 Aug. 16, 2012

Related U.S. Application Data

(62) Division of application No. 12/124,303, filed on May 21, 2008, now Pat. No. 8,193,194.

(60) Provisional application No. 60/931,722, filed on May 25, 2007.

(51) Int. Cl.
| | |
|---|---|
| *A61K 31/63* | (2006.01) |
| *A61K 31/655* | (2006.01) |
| *C07D 209/42* | (2006.01) |
| *C07D 215/06* | (2006.01) |
| *C07D 405/12* | (2006.01) |
| *C07D 209/08* | (2006.01) |
| *C07D 401/06* | (2006.01) |
| *C07D 401/04* | (2006.01) |
| *C07D 215/233* | (2006.01) |
| *C07D 317/60* | (2006.01) |
| *C07C 311/51* | (2006.01) |
| *C07C 311/53* | (2006.01) |

(52) U.S. Cl.
CPC ............ *C07D 209/08* (2013.01); *C07D 209/42* (2013.01); *C07D 215/06* (2013.01); *C07D 405/12* (2013.01); *C07D 401/06* (2013.01); *C07D 401/04* (2013.01); *C07D 215/233* (2013.01); *C07D 317/60* (2013.01); *C07C 311/51* (2013.01); *C07C 2102/08* (2013.01); *C07C 311/53* (2013.01)
USPC ............ 514/155; 514/156; 514/157; 514/158

(58) Field of Classification Search
CPC ............................ A61K 31/63; A61K 31/655
USPC .................................. 514/157, 158, 155, 156
See application file for complete search history.

(56) References Cited

U.S. PATENT DOCUMENTS

| | | | |
|---|---|---|---|
| 7,605,174 B2 | 10/2009 | Neubert et al. | |
| 7,615,563 B2 | 11/2009 | Gonzalez, III et al. | |
| 7,683,066 B2 | 3/2010 | Termin et al. | |
| 7,683,083 B2 | 3/2010 | Martinborough et al. | |
| 7,745,629 B2 | 6/2010 | Termin et al. | |
| 7,786,137 B2 | 8/2010 | Kawatkar et al. | |
| 7,799,822 B2 | 9/2010 | Martinborough et al. | |
| 7,842,819 B2 | 11/2010 | Martinborough et al. | |
| 7,846,954 B2 | 12/2010 | Zimmerman et al. | |
| 7,855,220 B2 | 12/2010 | Neubert et al. | |
| 7,968,545 B2 * | 6/2011 | Wilson et al. | 514/234.5 |
| 7,989,481 B2 | 8/2011 | Neubert et al. | |
| 7,994,166 B2 | 8/2011 | Stamos et al. | |
| 7,994,174 B2 | 8/2011 | Martinborough et al. | |
| 8,097,636 B2 | 1/2012 | Stamos et al. | |
| 8,129,546 B2 | 3/2012 | Martinborough et al. | |
| 8,143,297 B2 | 3/2012 | Hilgraf et al. | |
| 8,153,655 B2 | 4/2012 | Gonzalez, III et al. | |
| 8,163,720 B2 | 4/2012 | Martinborough et al. | |
| 8,193,194 B2 | 6/2012 | Martinborough et al. | |
| 8,202,861 B2 | 6/2012 | Gonzales, III et al. | |
| 8,236,829 B2 | 8/2012 | Neubert et al. | |
| 8,236,833 B2 | 8/2012 | Martinborough et al. | |
| 8,309,543 B2 | 11/2012 | Gonzalez, III et al. | |
| 8,309,587 B2 | 11/2012 | Martinborough et al. | |
| 8,314,125 B2 | 11/2012 | Termin et al. | |
| 8,343,763 B2 | 1/2013 | Hilgraf et al. | |
| 8,357,702 B2 | 1/2013 | Neubert et al. | |
| 8,362,032 B2 | 1/2013 | Kawatkar et al. | |
| 8,372,843 B2 | 2/2013 | Termin et al. | |
| 8,492,403 B2 | 7/2013 | Neubert et al. | |
| 8,536,195 B2 | 9/2013 | Termin et al. | |
| 2012/0010416 A1 | 1/2012 | Stamos et al. | |
| 2013/0035310 A1 | 2/2013 | Martinborough et al. | |
| 2013/0184258 A1 | 7/2013 | Gonzalez, III | |

\* cited by examiner

*Primary Examiner* — James O Wilson
*Assistant Examiner* — Ebenezer O Sackey
(74) *Attorney, Agent, or Firm* — Michael J. DiVerdi

(57) ABSTRACT

In general, the invention relates to compounds useful as ion channel modulators. It has now been found that compounds of this invention, and pharmaceutically acceptable compositions thereof, are useful as inhibitors of voltage-gated sodium channels.

28 Claims, No Drawings

ION CHANNEL MODULATORS AND METHODS OF USE

CROSS REFERENCE TO RELATED APPLICATIONS

This application is a divisional of U.S. patent application Ser. No. 12/124,303, filed May 21, 2008, which claims the benefit of priority under 35 U.S.C. §119 to U.S. provisional patent application Ser. No. 60/931,722, filed May 25, 2007, the entire contents of all applications are incorporated herein by reference.

TECHNICAL FIELD OF THE INVENTION

The present invention relates to compounds useful as inhibitors of ion channels.

The invention also provides pharmaceutically acceptable compositions comprising the compounds of the invention and methods of using the compositions in the treatment of various disorders.

BACKGROUND OF THE INVENTION

The present invention relates to compounds useful as inhibitors of ion channels.

The invention also provides pharmaceutically acceptable compositions comprising the compounds of the invention and methods of using the compositions in the treatment of various disorders.

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such, they play key roles in a variety of disease states such as epilepsy (See, Moulard, B. and D. Bertrand (2002) "Epilepsy and sodium channel blockers" Expert Opin. Ther. Patents 12(1): 85-91)), pain (See, Waxman, S. G., S. Dib-Hajj, et al. (1999) "Sodium channels and pain" Proc Natl Acad Sci USA 96(14): 7635-9 and Waxman, S. G., T. R. Cummins, et al. (2000) "Voltage-gated sodium channels and the molecular pathogenesis of pain: a review" J Rehabil Res Dev 37(5): 517-28), myotonia (See, Meola, G. and V. Sansone (2000) "Therapy in myotonic disorders and in muscle channelopathies" Neurol Sci 21(5): S953-61 and Mankodi, A. and C. A. Thornton (2002) "Myotonic syndromes" Curr Opin Neurol 15(5): 545-52), ataxia (See, Meisler, M. H., J. A. Kearney, et al. (2002) "Mutations of voltage-gated sodium channels in movement disorders and epilepsy" Novartis Found Symp 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" Proc Natl Acad Sci USA 97(21): 11598-602, and Renganathan, M., M. Gelderblom, et al. (2003) "Expression of Na(v)1.8 sodium channels perturbs the firing patterns of cerebellar purkinje cells" Brain Res 959(2): 235-42), irritable bowel (See, Su, X., R. E. Wachtel, et al. (1999) "Capsaicin sensitivity and voltage-gated sodium currents in colon sensory neurons from rat dorsal root ganglia" Am J Physiol 277(6 Pt 1): G1180-8, and Laird, J. M., V. Souslova, et al. (2002) "Deficits in visceral pain and referred hyperalgesia in NaV1.8 (SNS/PN3)—null mice" J Neurosci 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" J Neurosci 21(21): 8690-6), as well as an array of psychiatry dysfunctions such as anxiety and depression (See, Hurley, S. C. (2002) "Lamotrigine update and its use in mood disorders" Ann Pharmacother 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" Annu Rev Physiol 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" FEBS Lett 259(1): 213-6).

TABLE 1

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

(Abbreviations: CNS = central nervous system, PNS = peripheral nervous sytem, DRG = dorsal root ganglion, TG = Trigeminal ganglion)

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" Pain 87(1): 7-17.), bupivacaine, phenyloin (See, Jensen, T. S. (2002) "Anticonvulsants in neuropathic pain: rationale and clinical evidence" Eur J Pain 6 (Suppl A): 61-8), lamotrigine (See, Rozen, T. D. (2001) "Antiepileptic drugs in the management of cluster headache and trigeminal neuralgia" Headache 41 Suppl 1: S25-32 and Jensen, T. S. (2002) "Anticonvulsants in neuropathic pain: rationale and clinical evidence" Eur J Pain 6 (Suppl A): 61-8.), and carbamazepine (See, Backonja, M. M. (2002) "Use of anticonvulsants for treatment of neuropathic pain" Neurology 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" Annu Rev Physiol 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" Neurosci Lett 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" Nat Neurosci 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" Nature 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" Pain 95(1-2): 143-52, and Lai, J., J. C. Hunter, et al. (2000) "Blockade of neuropathic pain by antisense targeting of tetrodotoxin-resistant sodium channels in sensory neurons" Methods Enzymol 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states, there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." Pain 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "NaV1.3 sodium channels: rapid repriming and slow closed-state inactivation display quantitative differences after expression in a mammalian cell line and in spinal sensory neurons" J Neurosci 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." J Neurosci 22(17): 7425-33.). It has a slow rate of inactivation and left-shifted voltage dependence for activation (See, Dib-Hajj, S., J. A. Black, et al. (2002) "NaN/NaV1.9: a sodium channel with unique properties" Trends Neurosci 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" Acta Neurochir (Wien) 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to its role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" Embo J 14(6): 1084-90).

NaV1.1 (See, Sugawara, T., E. Mazaki-Miyazaki, et al. (2001) "Nav1.1 mutations cause febrile seizures associated with afebrile partial seizures." Neurology 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" Proc Natl Acad Sci USA 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" Novartis Found Symp 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." J Clin Invest 99(7): 1714-20).

Several Na channel blockers are currently used or being tested in the clinic to treat epilepsy (See, Moulard, B. and D. Bertrand (2002) "Epilepsy and sodium channel blockers" Expert Opin. Ther. Patents 12(1): 85-91.); acute (See, Wiffen, P., S. Collins, et al. (2000) "Anticonvulsant drugs for acute and chronic pain" Cochrane Database Syst Rev 3), chronic (See, Wiffen, P., S. Collins, et al. (2000) "Anticonvulsant drugs for acute and chronic pain" Cochrane Database Syst Rev 3, and Guay, D. R. (2001) "Adjunctive agents in the management of chronic pain" Pharmacotherapy 21(9): 1070-81), inflammatory (See, Gold, M. S. (1999) "Tetrodotoxin-resistant Na+ currents and inflammatory hyperalgesia." Proc Natl Acad Sci USA 96(14): 7645-9), and neuropathic pain (See, Strichartz, G. R., Z. Zhou, et al. (2002) "Therapeutic concentrations of local anaesthetics unveil the potential role of sodium channels in neuropathic pain" Novartis Found Symp 241: 189-201, and Sandner-Kiesling, A., G. Rumpold Seitlinger, et al. (2002) "Lamotrigine monotherapy for control of neuralgia after nerve section" Acta Anaesthesiol Scand 46(10): 1261-4); cardiac arrhythmias (See, An, R. H., R. Bangalore, et al. (1996) "Lidocaine block of LQT-3 mutant human Na+ channels" Circ Res 79(1): 103-8, and Wang, D. W., K. Yazawa, et al. (1997) "Pharmacological targeting of long QT mutant sodium channels" J Clin Invest 99(7): 1714-20); for neuroprotection (See, Taylor, C. P. and L. S, Narasimhan (1997) "Sodium channels and therapy of central nervous system diseases" Adv Pharmacol 39: 47-98) and as anesthetics (See, Strichartz, G. R., Z. Zhou, et al. (2002) "Therapeutic concentrations of local anaesthetics unveil the potential role of sodium channels in neuropathic pain." Novartis Found Symp 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3; non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including cluster headaches (see, Costa, A., et al., Cephalalgia. 2000; 20(2):85-91); chronic neuropathic pain, including post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J. Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hai™, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phanton pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including abdominal pain; pyelonephritis; appendicitis; cholecystitis; intestinal obstruction; hernias; etc (see, Giambernardino, M. A., et al., Pain. 1995; 61(3):459-69); chest pain, including cardiac Pain (see, Vergona, R. A., et al., Life Sci. 1984; 35(18):1877-84); pelvic pain, renal colic pain, acute obstetric pain, including labor pain (see, Segal, S., et al., Anesth Analg. 1998; 87(4):864-9); cesarean section pain; acute inflammatory, burn and trauma pain; acute intermittent pain, including endometriosis (see, Cason, A. M., et al., Horm Behay. 2003; 44(2):123-31); acute herpes zoster pain; sickle cell anemia; acute pancreatitis (see, Toma, H; Gastroenterology. 2000; 119(5):1373-81); breakthrough pain; orofacial pain, including sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cyctitis (IC) (see, Giannakopoulos& Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Unfortunately, as described above, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

In general, the invention relates to compounds useful as modulators of ion channel activity. It has now been found that compounds of this invention, and pharmaceutically acceptable compositions thereof, are useful as inhibitors of voltage-gated sodium channels. These compounds have the general formula I:

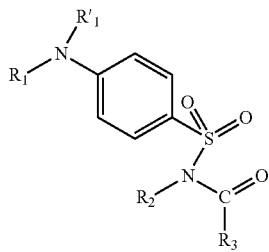

I or a pharmaceutically acceptable salt thereof, wherein $R_1$, $R'_1$, $R_2$, and $R_3$ are described herein.

The present invention also includes methods for treating or lessening the severity of a disease, condition, or disorder where activation or hyperactivity of sodium ion channels is implicated in the disease state. Methods for treating or lessening the severity of a pain condition are also disclosed. In one aspect, the method comprises the step of administering to the patient an effective amount of a pharmaceutical composition comprising at least one compound of the present invention.

The compounds of the present invention are useful for treating or lessening the severity of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

The present invention also presents novel pharmaceutical compositions formulated with the compounds described herein and a pharmaceutical carrier.

DETAILED DESCRIPTION OF THE INVENTION

I. Definitions

As used herein, the following definitions shall apply unless otherwise indicated.

The term "modulating" as used herein means increasing or decreasing, e.g. activity, by a measurable amount. Compounds that modulate ion channel activity, such as sodium ion channel activity, by increasing the activity of the ion channel, e.g., a sodium ion channel, are called agonists. Compounds that modulate ion channel activity, such as sodium ion channel activity, by decreasing the activity of the ion channel, e.g., sodium ion channel, are called antagonists. An agonist interacts with an ion channel, such as a sodium ion channel, to increase the ability of the receptor to transduce an intracellular signal in response to endogenous ligand binding. An antagonist interacts with an ion channel and competes with the endogenous ligand(s) or substrate(s) for binding site(s) on the receptor to decrease the ability of the receptor to transduce an intracellular signal in response to endogenous ligand binding.

The phrase "treating or reducing the severity of an ion channel mediated disease" refers both to treatments for diseases that are directly caused by ion channel activities and alleviation of symptoms of diseases not directly caused by ion channel activities. Examples of diseases whose symptoms may be affected by ion channel activities include, but are not limited to, acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

As described herein, compounds of the invention may optionally be substituted with one or more substituents, such as are illustrated generally above, or as exemplified by particular classes, subclasses, and species of the invention.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, or heterocycloaliphaticamino]; sulfonyl [e.g., aliphatic-S(O)$_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroarylalkoxy; alkoxycarbonyl; alkylcarbonyloxy; or hydroxy. Without limitation, some examples of substituted alkyls include carboxyalkyl (such as HOOC-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfonylamino)alkyl (such as alkyl-S(O)$_2$-aminoalkyl); aminoalkyl; amidoalkyl; (cycloaliphatic)alkyl; or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, heterocycloaliphaticamino, or aliphaticsulfonylamino]; sulfonyl [e.g., alkyl-S(O)$_2$—, cycloaliphatic-S(O)$_2$—, or aryl-S(O)$_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-S(O)$_2$-aminoalkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl; heteroaroyl; alkoxy; cycloalkyloxy; heterocycloalkyloxy; aryloxy; heteroaryloxy; aralkyloxy; nitro; carboxy; cyano; halo; hydroxy; sulfo; mercapto; sulfanyl [e.g., aliphatic-S— or cycloaliphatic-S—]; sulfinyl [e.g., aliphatic-S(O)— or cycloaliphatic-S(O)—]; sulfonyl [e.g., aliphatic-S(O)$_2$—, aliphaticamino-S(O)$_2$—, or cycloaliphatic-S(O)$_2$—]; amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl]; urea; thiourea; sulfamoyl; sulfamide; alkoxycarbonyl; alkylcarbonyloxy; cycloaliphatic; heterocycloaliphatic; aryl; heteroaryl; acyl [e.g., (cycloaliphatic)carbonyl or (heterocycloaliphatic)carbonyl]; amino [e.g., aliphaticamino]; sulfoxy; oxo; carbamoyl; (cycloaliphatic)oxy; (heterocycloaliphatic)oxy; or (heteroaryl)alkoxy.

As used herein, an "amido" encompasses both "aminocarbonyl" and "carbonylamino". These terms when used alone or in connection with another group refers to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy;

heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl, (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl]; sulfonyl [e.g., aliphatic-S(O)$_2$— or amino-S(O)$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl]; cycloaliphatic [e.g., cycloalkyl or cycloalkenyl]; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino]; cyano; halo; hydroxy; acyl; mercapto; alkylsulfanyl; sulfoxy; urea; thiourea; sulfamoyl; sulfamide; oxo; or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl]; cyano; halo; hydroxy; mercapto; sulfonyl [e.g., alkyl-S(O)$_2$— and aryl-S(O)$_2$—]; sulfinyl [e.g., alkyl-S(O)—]; sulfanyl [e.g., alkyl-S—]; sulfoxy; urea; thiourea; sulfamoyl; sulfamide; oxo; or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline to produce a heteroaryl group.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S).

Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy;

aroyl; heteroaroyl; amino; amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl]; nitro; cyano; halo; hydroxy; mercapto; sulfonyl [e.g., alkylsulfonyl or arylsulfonyl]; sulfinyl [e.g., alkylsulfinyl]; sulfanyl [e.g., alkylsulfanyl]; sulfoxy; urea; thiourea; sulfamoyl; sulfamide; oxo; or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, puryl, cinnolyl, quinolyl, quinazolyl, cinnolyl, phthalazyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$S(O)_2$— or amino-$S(O)_2$—]; sulfinyl [e.g., aliphatic-$S(O)$—]; sulfanyl [e.g., aliphatic-S—]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (e.g., carboxyalkyl, hydroxyalkyl, and haloalkyl such as trifluoromethyl); alkenyl; alkynyl; cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; aminocarbonyl; alkylcarbonylamino; cycloalkylcarbonylamino; (cycloalkylalkyl)carbonylamino; arylcarbonylamino; aralkylcarbonylamino; (heterocycloalkyl)carbonylamino; (heterocycloalkylalkyl)carbonylamino; heteroarylcarbonylamino; heteroaralkylcarbonylamino; cyano; halo; hydroxy; acyl; mercapto; alkylsulfanyl; sulfoxy; urea; thiourea; sulfamoyl; sulfamide; oxo; or carbamoyl.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ can be aliphatic, aryl, aralipatic, heterocycloaliphatic, heteroaryl, or heteroaraliphatic.

As used herein, a "carboxy" group refers to —COOH, —$COOR^X$, —OC(O)H, —OC(O)$R^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidino" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic group" or "cyclic moiety" include mono-, bi-, and tri-cyclic ring systems including cycloaliphatic, heterocycloaliphatic, aryl, or heteroaryl, each of which has been previously defined.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$- where Q is independently hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, R$_3$, and R$_4$, and other variables contained therein formulae I encompass specific groups, such as alkyl and aryl. Unless otherwise noted, each of the specific groups for the variables R$_1$, R$_2$, R$_3$, and R$_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Compounds

Compounds of the present invention are useful modulators of Na ion channel.

The present invention includes a compound of formula I,

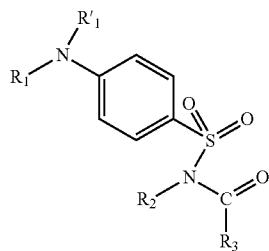

or a pharmaceutically acceptable salt thereof.

Each of $R'_1$ and $R_1$ is independently —$Z^A R_4$, wherein each $Z^A$ is independently a bond or an optionally substituted branched or straight $C_{1-12}$ aliphatic chain wherein up to three carbon units of $Z^A$ are optionally and independently replaced by —C(O)—, —C(S)—, —C(O)NR$^A$—, —C(O)NR$^A$NR$^A$—, —C(O)O—, —NR$^A$C(O)O—, —O—, —NR$^A$C(O)NR$^A$—, —NR$^A$NR$^A$—, —S—, —SO—, —SO$_2$—, —NR$^A$—, —SO$_2$NR$^A$—, or —NR$^A$SO$_2$NR$^A$—. Each $R_4$ is independently R$^A$, halo, —OH, —CN, —NO$_2$, —NH$_2$, or —OCF$_3$. Each R$^A$ is independently hydrogen, an optionally substituted aryl, or an optionally substituted heteroaryl. Alternatively, $R'_1$ and $R_1$ together with the nitrogen atom to which they are attached form a heterocycloaliphatic that is substituted with two of —$Z^B R_5$, wherein each $Z^B$ is independently a bond or an optionally substituted branched or straight $C_{1-6}$ aliphatic chain wherein up to three carbon units of $Z^B$ are optionally and independently replaced by —C(O)—, —C(S)—, —C(O)NR$^B$—, —C(O)NR$^B$NR$^B$—, —C(O)O—, —NR$^B$C(O)O—, —O—, —NR$^B$C(O)NR$^B$—, —NR$^B$NR$^B$—, —S—, —SO—, —SO$_2$—, —NR$^B$—, —SO$_2$NR$^B$—, or —NR$^B$SO$_2$NR$^B$—. Each $R_5$ is independently R$^B$, halo, —OH, —CN, —NO$_2$, —NH$_2$, =O, or —OCF$_3$. Each R$^B$ is independently hydrogen, an optionally substituted aryl, or an optionally substituted heteroaryl.

$R_2$ is —$Z^C R_6$, wherein each $Z^C$ is independently a bond or an optionally substituted branched or straight $C_{1-6}$ aliphatic chain wherein up to two carbon units of $Z^C$ are optionally and independently replaced by —C(O)—, —C(S)—, —C(O)NR$^C$—, —C(O)NR$^C$NR$^C$—, —C(O)O—, —NR$^C$C(O)O—, —O—, —NR$^C$C(O)NR$^C$—, —NR$^C$NR$^C$—, —S—, —SO—, —SO$_2$—, —NR$^S$—, —SO$_2$NR$^C$—, or —NR$^C$SO$_2$NR$^C$—. Each $R_6$ is independently R$^C$, halo, —OH, —CN, —NO$_2$, —NH$_2$, or —OCF$_3$. Each R$^C$ is independently hydrogen, optionally substituted cycloaliphatic, optionally substituted heterocycloaliphatic, optionally substituted aryl, or optionally substituted heteroaryl.

$R_3$ is —$Z^D R_2$, wherein each $Z^D$ is independently a bond or an optionally substituted branched or straight $C_{1-6}$ aliphatic chain wherein up to two carbon units of $Z^C$ are optionally and independently replaced by —C(O)—, —C(S)—, —C(O)NR$^D$—, —C(O)NR$^D$NR$^D$—, —C(O)O—, —NR$^D$C(O)O—, —O—, —NR$^D$C(O)NR$^D$—, —NR$^D$NR$^D$—, —S—, —SO—, —SO$_2$—, —NR$^D$—, —SO$_2$NR$^D$—, or —NR$^D$SO$_2$NR$^D$—. Each $R_7$ is independently R$^D$, halo, —OH, —CN, —NO$_2$, —NH$_2$, or —OCF$_3$. Each R$^D$ is independently hydrogen, optionally substituted cycloaliphatic, optionally substituted heterocycloaliphatic, optionally substituted aryl, or optionally substituted heteroaryl.

1. $R_1$ and $R'_1$ Groups

Each of $R'_1$ and $R_1$ is independently —$Z^A R_4$, wherein each $Z^A$ is independently a bond or an optionally substituted branched or straight $C_{1-12}$ aliphatic chain wherein up to three carbon units of $Z^A$ are optionally and independently replaced by —C(O)—, —C(S)—, —C(O)NR$^A$—, —C(O) NR$^A$NR$^A$—, —C(O)O—, —NR$^A$C(O)O—, —O—, —NR$^A$C (O)NR$^A$—, —NR$^A$NR$^A$—, —S—, —SO—, —SO$_2$—, —NR$^A$—, —SO$_2$NR$^A$—, or —NR$^A$SO$_2$NR$^A$—. Each R$_4$ is independently R$^A$, halo, —OH, —CN, —NO$_2$, —NH$_2$, or —OCF$_3$. Each R$^A$ is independently hydrogen, an optionally substituted aryl, an optionally substituted heteroaryl, or an optionally substituted cycloaliphatic. Alternatively, R'$_1$ and R$_1$ together with the nitrogen atom to which they are attached form a heterocycloaliphatic that is substituted with two of —Z$^D$R$_5$, wherein each Z$^B$ is independently a bond or an optionally substituted branched or straight C$_{1-6}$ aliphatic chain wherein up to three carbon units of Z$^B$ are optionally and independently replaced by —C(O)—, —C(S)—, —C(O) NR$^B$—, —C(O)NR$^B$NR$^B$—, —C(O)O—, —NR$^B$C(O)O—, —O—, —NR$^B$C(O)NR$^B$—, —NR$^B$NR$^B$—, —S—, —SO—, —SO$_2$—, —NR$^B$—, —SO$_2$NR$^B$—, or —NR$^B$SO$_2$NR$^B$—. Each R$_5$ is independently R$^B$, halo, —OH, —CN, —NO$_2$, —NH$_2$, =O, or —OCF$_3$. Each R$^B$ is independently hydrogen, an optionally substituted aryl, or an optionally substituted heteroaryl.

In several embodiments, one of R'$_1$ and R$_1$ is —Z$^A$R$_4$, wherein Z$^A$ is independently a bond or an optionally substituted branched or straight C$_{1-6}$ aliphatic chain wherein up to 2 carbon units of Z$^A$ are optionally and independently replaced by —C(O)—, —C(O)NR$^A$—, —C(O)O—, —O—, or —NR$^A$—; R$_4$ is R$^A$, halo, —OH, —CN, —NO$_2$, —NH$_2$, or —OCF$_3$; and each R$^A$ is independently hydrogen, an optionally substituted aryl, or an optionally substituted heteroaryl.

In other embodiments, each of R'$_1$ and R$_1$ is independently

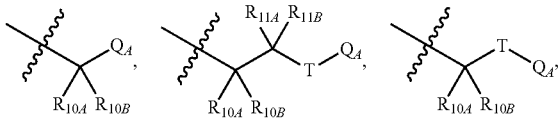

or -Q$_A$, wherein each of R$_{10A}$ and R$_{10B}$ is independently hydrogen, unsubstituted straight or branched C$_{1-3}$ aliphatic, or R$_{10A}$ and R$_{10B}$ together form an oxo group; each of R$_{11A}$ and R$_{11B}$ is independently hydrogen, optionally substituted straight or branched C$_{1-5}$ aliphatic, or R$_{11A}$ and R$_{11B}$ together with the carbon atom to which they are attached form an unsubstituted 3-5 membered cycloaliphatic; T is independently a bond, —O—, —NR$_{10A}$—, or —CH$_2$—; and Q$_A$ is hydrogen or an aryl or heteroaryl, each of which is optionally substituted with 1-3 of halo, hydroxy, optionally substituted C$_{1-3}$ alkoxy, or optionally substituted C$_{1-3}$ aliphatic.

In several embodiments, R$_{10A}$ and R$_{10B}$ together form an oxo group; one of R$_{11A}$ and R$_{11B}$ is hydrogen and the remaining R$_{11A}$ or R$_{11B}$ is optionally substituted straight or branched C$_{1-5}$ aliphatic or hydrogen; T is a bond, —O—, —NR$_{10A}$—, or —CH$_2$—; and Q$_A$ is phenyl, monocyclic heteroaryl, or bicyclic heteroaryl, each of which is optionally substituted with 1-3 of halo, —OH, —CN, optionally substituted C$_{1-3}$ aliphatic, or combinations thereof.

In several examples, one of R$_{11A}$ and R$_{11B}$ is hydrogen and the remaining R$_{11A}$ or R$_{11B}$ is optionally substituted straight or branched C$_{1-5}$ alkyl, optionally substituted straight or branched C$_{2-5}$ alkenyl, or hydrogen. For example, one of R$_{11A}$ and R$_{11B}$ is hydrogen and the remaining R$_{11A}$ or R$_{11B}$ is optionally substituted straight or branched C$_{1-5}$ alkyl. In several compounds, one of R$_{11A}$ and R$_{11B}$ is hydrogen and the remaining R$_{11A}$ or R$_{11B}$ is methyl, ethyl, propyl, isopropyl, butyl, isobutyl, or tertbutyl, each of which is optionally substituted with hydroxy.

In several examples, T is independently a bond, —O—, —NR$_{10A}$—, or —CH$_2$—, wherein —NR$_{10A}$— is —NH—.

In several additional examples, Q$_A$ is phenyl, bicyclic aryl, monocyclic heteroaryl, or bicyclic heteroaryl, each of which is optionally substituted with 1-3 of halo, —OH, —CN, optionally substituted C$_{1-3}$ alkoxy, optionally substituted C$_{1-3}$ aliphatic, or combinations thereof. For example, Q$_A$ is a phenyl that is substituted with 1-3 of halo, unsubstituted C$_{1-3}$ alkyl, or unsubstituted C$_{1-3}$ alkoxy. In other embodiments, Q$_A$ is an unsubstituted phenyl.

In several examples, Q$_A$ is an optionally substituted 9-10 membered bicyclic aryl. For example, Q$_A$ is naphthylene-yl or 2,3-dihydro-1H-indene-yl, either of which is unsubstituted.

In alternative embodiments, Q$_A$ is a monocyclic or bicyclic heteraryl, each of which is optionally substituted with 1-3 of halo, —OH, —CN, optionally substituted C$_{1-3}$ alkoxy, optionally substituted C$_{1-3}$ aliphatic, or combinations thereof. In several compounds of the present invention, Q$_A$ is an optionally substituted 5-6 membered monocyclic heteroaryl. In other examples, Q$_A$ is an optionally substituted 5-6 membered monocyclic heteroaryl having 1-3 heteroatoms selected from N, O, and S. In still other examples, Q$_A$ is a 5-6 membered monocyclic heteroaryl that is optionally substituted with 1-3 of halo, —OH, —CN, optionally substituted C$_{1-3}$ alkoxy, optionally substituted C$_{1-3}$ aliphatic, or combinations thereof. For example, Q$_A$ is furan-yl, thiophene-yl, oxazole-yl, pyridine-yl, pyramidine-yl, pyrazine-yl, or 1,3,5-triazine-yl each of which is optionally substituted with 1-3 of halo, —OH, —CN, optionally substituted C$_{1-3}$ alkoxy, optionally substituted C$_{1-3}$ aliphatic, or combinations thereof.

In other embodiments, Q$_A$ is an optionally substituted bicyclic heteroaryl. For example, Q$_A$ is an optionally substituted bicyclic heteroaryl having 1-3 heteroatoms selected from N, O, and S. In other examples, Q$_A$ is an optionally substituted 9-10 membered heteroaryl having 1-3 heteroatoms selected from N, O, and S. In still other examples, Q$_A$ is indolizine-yl, indole-yl, isoindole-yl, 3H-indole-yl, indoline-yl, 1,2,3,4-tetrahydroquinoline-yl, benzo[d][1,3]dioxole-yl, quinoline-yl, each of which is optionally substituted with 1-3 of halo, —OH, —CN, optionally substituted C$_{1-3}$ alkoxy, optionally substituted C$_{1-3}$ aliphatic, or combinations thereof.

In alternative embodiments, one of R'$_1$ and R$_1$ is hydrogen and the remaining R'$_1$ or R$_1$ is selected from:

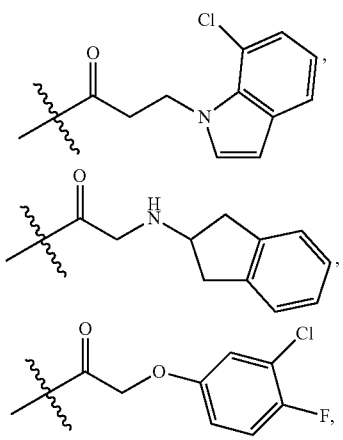

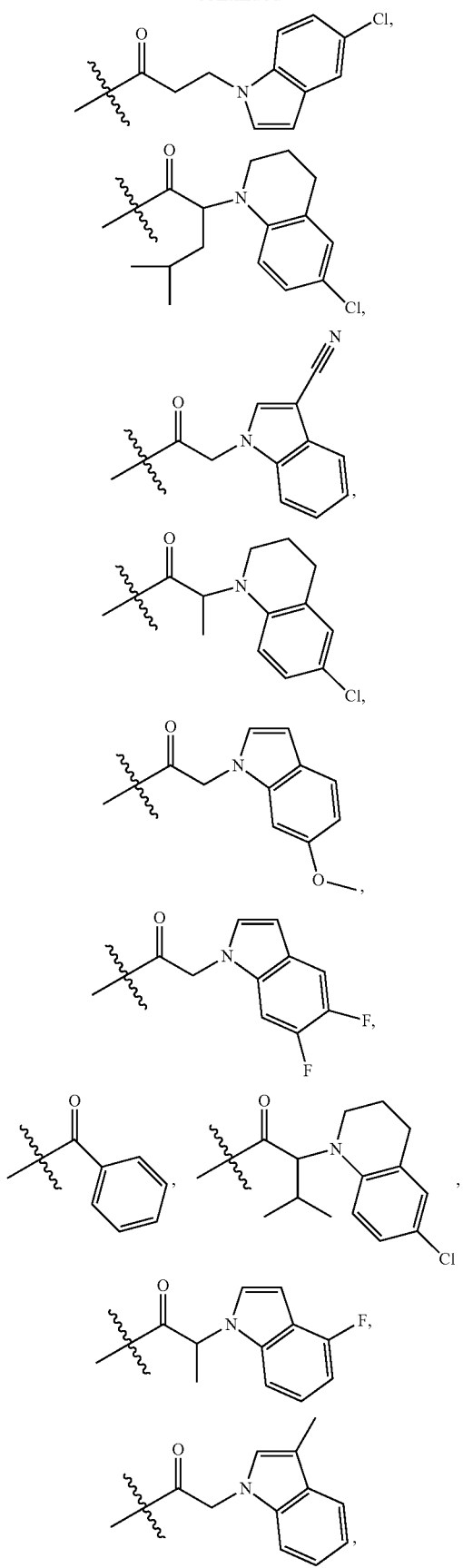
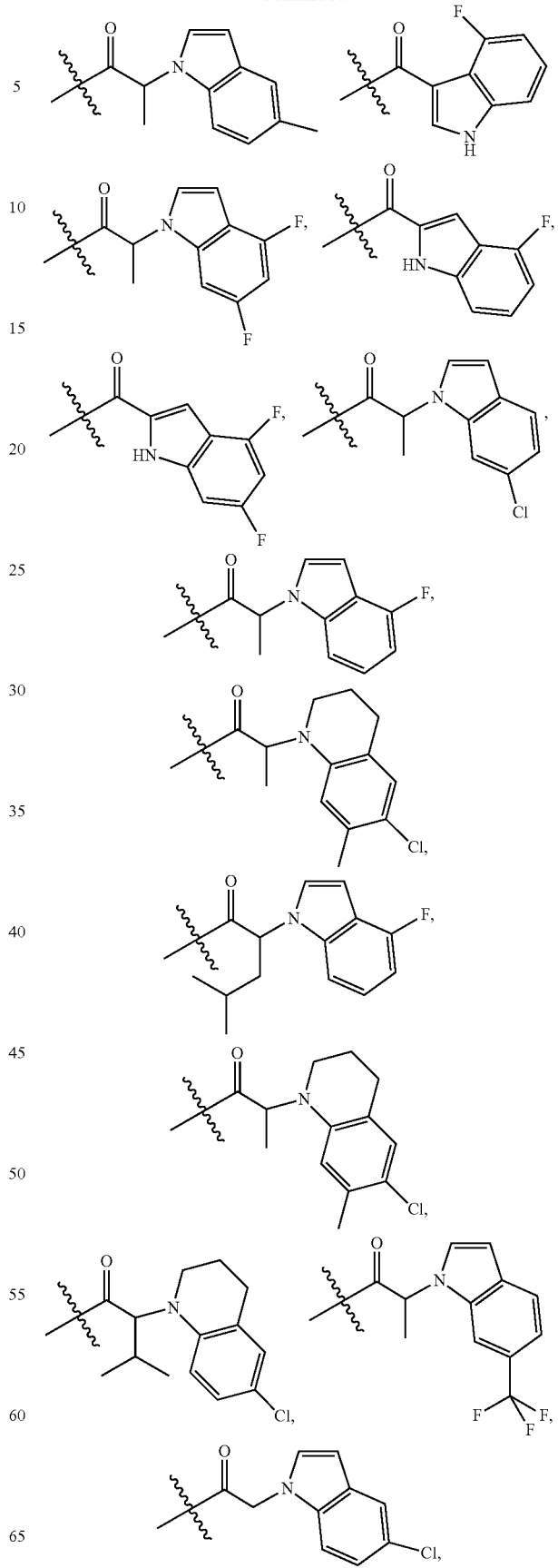

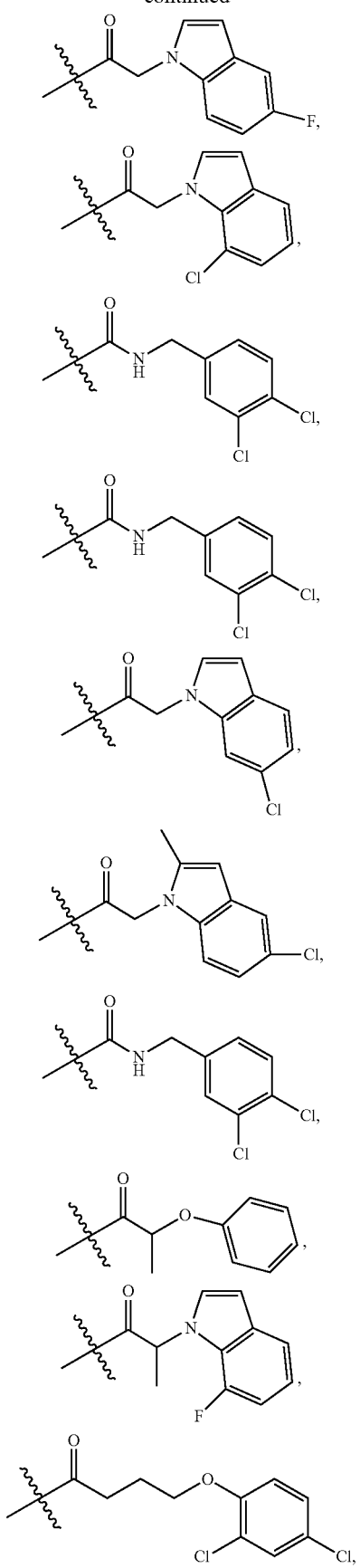
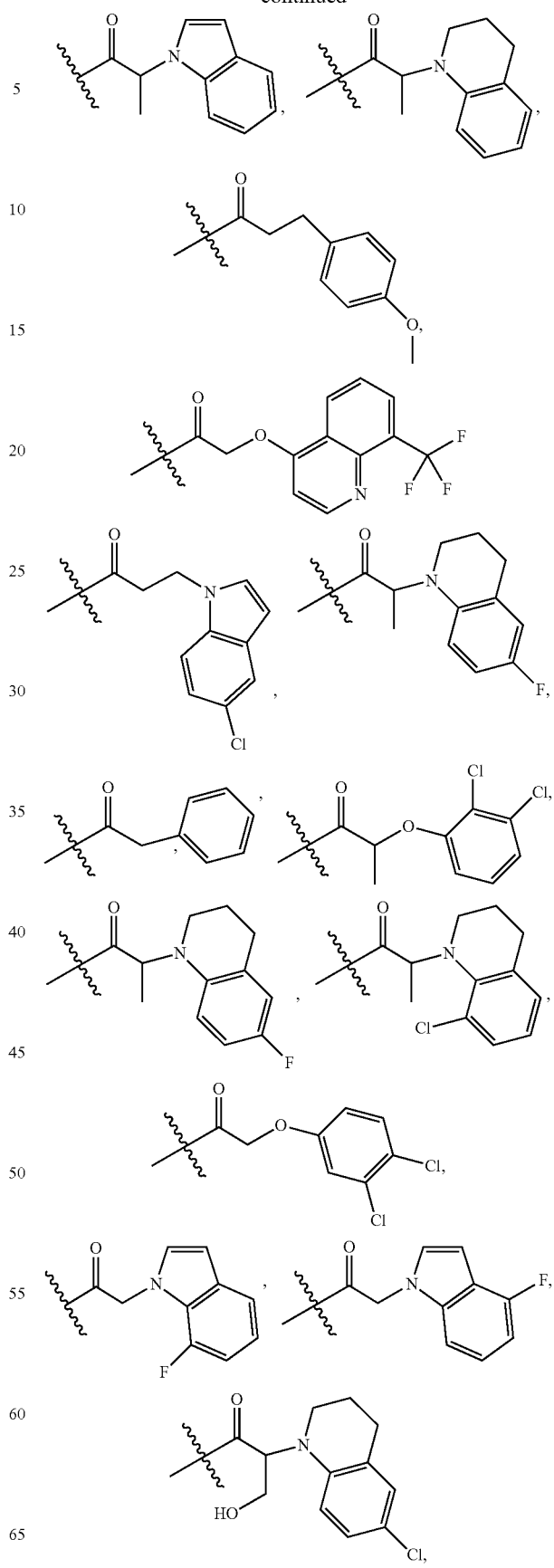

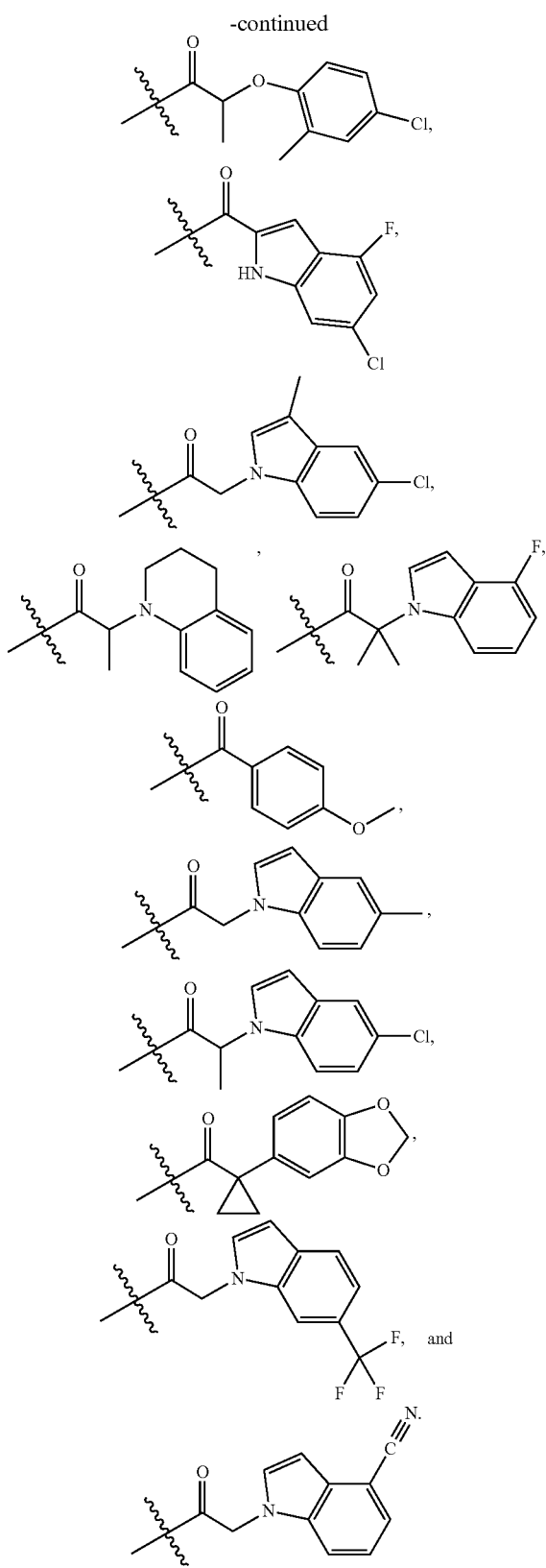

In several embodiments, R'₁ and R₁ together with the nitrogen atom to which they are attached form a heterocycloaliphatic that is substituted with two of —Z^B R₅, wherein each Z^B is independently a bond or an optionally substituted branched or straight C₁₋₆ aliphatic chain wherein up to three carbon units of Z^B are optionally and independently replaced by —C(O)—, —C(S)—, —C(O)NR^B—, —C(O)NR^B-NR^B—, —C(O)O—, —NR^B C(O)O—, —O—, —NR^B C(O)NR^B—, —NR^B NR^B—, —S—, —SO—, —SO₂—, —NR^B—, —SO₂NR^B—, or —NR^B SO₂NR^B—. Each R₅ is independently R^B, halo, —OH, —CN, —NO₂, —NH₂, =O, or —OCF₃. Each R^B is independently hydrogen, an optionally substituted aryl, or an optionally substituted heteroaryl.

In several embodiments, R'₁ and R₁ together with the nitrogen atom to which they are attached form a 5-7 membered heterocycloaliphatic that is substituted with at least one of an acyl group, an oxo group, a heteroaryl group, or combinations thereof. For example, R'₁ and R₁ together with the nitrogen atom to which they are attached form a form a 5-7 membered heterocycloaliphatic having 1-3 heteroatoms independently selected from N, O, and S that is substituted with at least one of an acyl group, an oxo group, a heteroaryl group, or combinations thereof. In other examples, R'₁ and R₁ together with the nitrogen atom to which they are attached form piperidine-yl, piperazine-yl, or pyrrolidone-yl, each of which is substituted with at least one of an acyl group, an oxo group, a heteroaryl group, or combinations thereof.

In other examples, R'₁ and R₁ together with the nitrogen atom to which they are attached form a heterocycloaliphatic selected from:

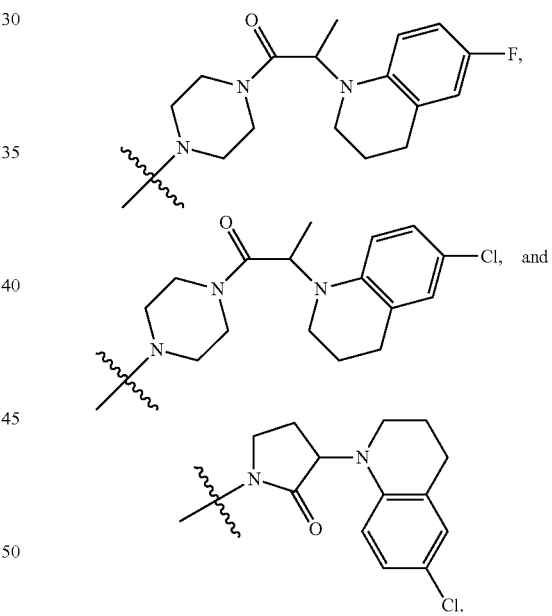

2. R₂ Group

R₂ is —Z^C R₆, wherein each Z^C is independently a bond or an optionally substituted branched or straight C₁₋₆ aliphatic chain wherein up to two carbon units of Z^C are optionally and independently replaced by —C(O)—, —C(S)—, —C(O)NR^C—, —C(O)NR^C NR^C—, —C(O)O—, —NR^C C(O)O—, —O—, —NR^C C(O)NR^C—, —NR^C NR^C—, —S—, —SO—, —SO₂—, —NR^S—, —SO₂NR^C—, or —NR^C SO₂NR^C—. Each R₄ is independently R^A, halo, —OH, —CN, —NO₂, —NH₂, or —OCF₃. Each R^C is independently hydrogen, optionally substituted cycloaliphatic, optionally substituted heterocycloaliphatic, optionally substituted aryl, or optionally substituted heteroaryl.

In several embodiments, $R_2$ is an optionally substituted $C_{1-4}$ aliphatic. For example, $R_2$ is an optionally substituted straight or branched $C_{1-4}$ alkyl, an optionally substituted straight or branched $C_{2-4}$ alkenyl, or an optionally substituted straight or branched $C_{2-4}$ alkynyl.

In other embodiments, $R_2$ is hydrogen.

3. $R_3$ Group $R_3$ is $-Z^D R_7$, wherein each $Z^D$ is independently a bond or an optionally substituted branched or straight $C_{1-6}$ aliphatic chain wherein up to two carbon units of $Z^D$ are optionally and independently replaced by $-C(O)-$, $-C(S)-$, $-C(O)NR^D-$, $-C(O)NR^D NR^D-$, $-C(O)O-$, $-NR^D C(O)O-$, $-O-$, $-NR^D C(O)NR^D-$, $-NR^D NR^D-$, $-S-$, $-SO-$, $-SO_2-$, $-NR^D-$, $-SO_2 NR^D-$, or $-NR^D SO_2 NR^D-$. Each $R_7$ is independently $R^D$, halo, $-OH$, $-CN$, $-NO_2$, $-NH_2$, or $-OCF_3$. Each $R^D$ is independently hydrogen, optionally substituted cycloaliphatic, optionally substituted heterocycloaliphatic, optionally substituted aryl, or optionally substituted heteroaryl.

In many embodiments, $R_3$ is $-Z^D R_7$, wherein each $Z^D$ is independently a bond or an optionally substituted straight or branched $C_{1-6}$ aliphatic chain wherein up to one carbon units of $Z^D$ is optionally and independently replaced by $-O-$, or $-NR^D-$; and each $R_7$ is independently $R^D$, halo, $-OH$, $-CN$, $-NO_2$, $-NH_2$, or $-OCF_3$. Each $R^D$ is independently hydrogen, optionally substituted cycloaliphatic, optionally substituted heterocycloaliphatic, optionally substituted aryl, or optionally substituted heteroaryl.

In some examples, $R_3$ is an optionally substituted $C_{1-5}$ alkoxy. For instance, $R_3$ is methoxy, ethoxy, propoxy, butoxy, or isopropoxy, each of which is unsubstituted. In other instances, $R_3$ is an optionally substituted $C_{1-5}$ alkynyl-oxy. For example, $R_3$ is unsubstituted pent-2-yn-yloxy.

In several embodiments, $R_3$ is an optionally substituted branched or straight $C_{1-6}$ aliphatic. In other examples, $R_3$ is methyl, ethyl, propyl, butyl, isoptopyl, isobutyl, tert butyl, or neopentyl, each of which is optionally substituted. In other instances, $R_3$ is methyl, ethyl, propyl, butyl, isoptopyl, isobutyl, tert butyl, or neopentyl, each of which is unsubstituted.

In several examples, $R_3$ is an optionally substituted cycloaliphatic. In several compounds, $R_3$ is an optionally substituted monocyclic cycloaliphatic. For instance, $R_3$ is an optionally substituted 3-7 membered monocyclic cycloaliphatic. In other compounds, $R_3$ is cyclopropyl, cyclobutyl, cyclopentyl, or cyclohexyl, each of which is unsubstituted.

In some embodiments, $R_3$ is an optionally substituted heterocycloaliphatic. For instance, $R_3$ is a monocyclic or bicyclic heterocycloaliphatic. In other embodiments, $R_3$ is an optionally substituted monocyclic heterocycloaliphatic having 1-3 heteroatoms selected from N, O, and S. For instance, $R_3$ is a piperidine-yl, piperazine-yl, pyrrolidine-yl, tetrahydrofuran-yl, tetrahydropyran-yl, thiomorpholine-yl, or imidazolidine-yl, each of which is optionally substituted with an unsubstituted $C_{1-3}$ aliphatic.

In alternative embodiments, $R_3$ is an optionally substituted aryl. For example, $R_3$ is an optionally substituted phenyl or an optionally substituted naphthyl. In other examples, $R_3$ is a phenyl optionally substituted with 1-3 of halo, alkoxy, aliphatic, or combinations thereof.

In several embodiments, $R_3$ is an optionally substituted aryloxy. For example, $R_3$ is an optionally substituted phenyloxy or an optionally substituted naphthyloxy. In other examples, $R_3$ is a phenyloxy optionally substituted with 1-3 of halo, alkoxy, aliphatic, or combinations thereof.

In several embodiments, $R_3$ is an optionally substituted heteroaryl. For example, $R_3$ is an optionally substituted heteroaryl having 1-3 heteroatoms selected from N, O, and S. In other examples, $R_3$ is a monocyclic or bicyclic heteroaryl, each of which is optionally substituted with 1-3 of halo, alkoxy, aliphatic, or combinations thereof. In several examples, $R_3$ is furan-yl, thiophene-yl, pyridine-yl, or pyrazine-yl, each of which is optionally substituted with 1-3 of halo, alkoxy, aliphatic, or combinations thereof.

In other examples, $R_3$ is optionally substituted amino. For example, $R_3$ is an optionally substituted (aliphatic)amino, (cycloaliphatic)amino, (aryl)amino, or an amido group. In other examples, $R_3$ is an unsubstituted amino group ($-NH_2$). In other examples, $R_3$ is an optionally substituted $C_{1-5}$ straight or branched (aliphatic)amino. For instance, $R_3$ is (methyl)amino, (butyl)amino or (tertbutyl)amino, each of which is unsubstituted.

In several examples, $R_3$ is one selected from: $-CH_3$, $-NH_2$,

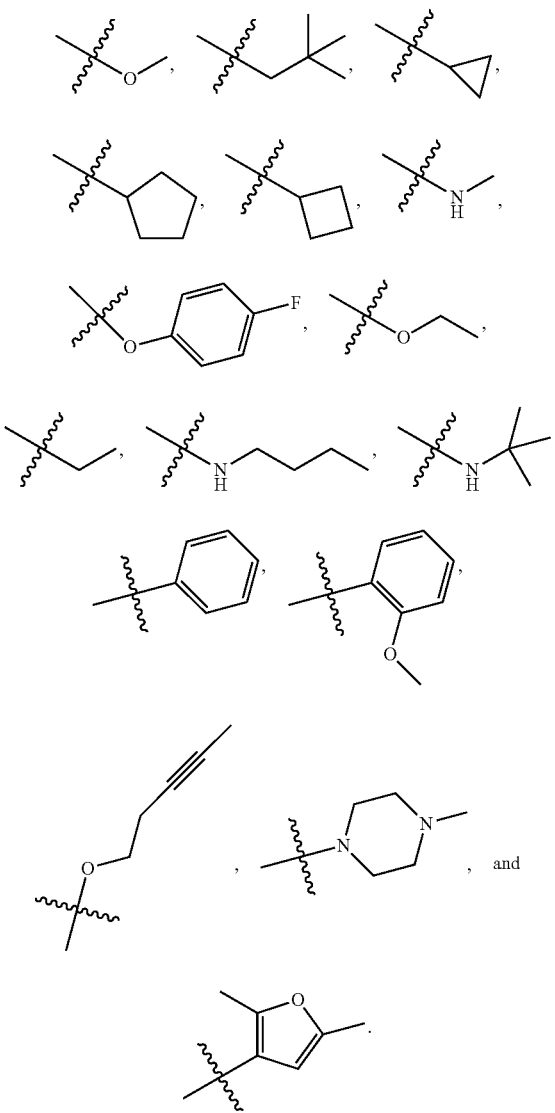

and

Another aspect of the present invention provides another group of compounds, and pharmaceutically acceptable compositions thereof, that are useful as inhibitors of voltage-gated sodium channels in the treatment of disorders where activation or hyperactivity of sodium ion channels is implicated in the disease state. These compounds have formula Ia:

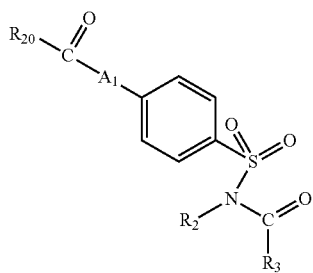

Ia or a pharmaceutically acceptable salt thereof, wherein $R_2$ and $R_3$ are defined above in formula I.

$A_1$ is —$NR_{21}$—, wherein $R_{21}$ is —$Z^E R_{22}$, wherein each $Z^E$ is independently a bond or an optionally substituted branched or straight $C_{1-6}$ aliphatic chain wherein up to three carbon units of $Z^E$ are optionally and independently replaced by —C(O)—, —C(O)$NR^E$—, —C(O)O—, —$NR^E$C(O)O—, —O—, or —$NR^E$—. Each $R_{22}$ is independently $R^E$, halo, —OH, —CN, —NO$_2$, —NH$_2$, or —OCF$_3$. Each $R^E$ is independently hydrogen, an optionally substituted aryl, or an optionally substituted heteroaryl.

$R_{20}$ is —$Z^F R_{30}$, wherein each $Z^F$ is independently a bond or an optionally substituted branched or straight $C_{1-6}$ aliphatic chain wherein up to three carbon units of $Z^F$ are optionally and independently replaced by —C(O)—, —C(O)$NR^F$—, —C(O)O—, —$NR^F$C(O)O—, —O—, or —$NR^F$—. Each $R_{30}$ is independently $R^F$, halo, —OH, —CN, —NO$_2$, —NH$_2$, or —OCF$_3$. Each $R^F$ is independently hydrogen, an optionally substituted aryl, or an optionally substituted heteroaryl.

Another aspect of the present invention provides another group of compounds, and pharmaceutically acceptable compositions thereof, that are useful as inhibitors of voltage-gated sodium channels in the treatment of disorders where activation or hyperactivity of sodium ion channels is implicated in the disease state. These compounds have formula Ib:

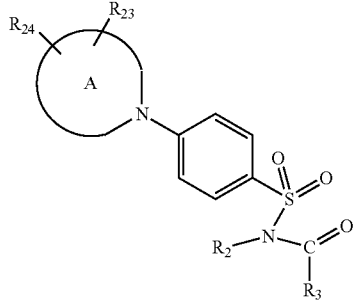

Ib or a pharmaceutically acceptable salt thereof, wherein $R_2$ and $R_3$ are defined above in formula I.

Ring A is a 5-6 membered heterocycloaliphatic ring having at least one nitrogen atom, wherein ring A attaches to the phenyl of formula Ib at ring A's nitrogen atom, and ring A is further attached to $R_{23}$ and $R_{24}$ at any chemically feasible position.

$R_{23}$ is independently —$Z^G R_{25}$, wherein each $Z^G$ is independently a bond or an optionally substituted branched or straight $C_{1-3}$ aliphatic chain wherein up to two carbon units of $Z^G$ are optionally and independently replaced by —C(O)—, —C(O)$NR^G$—, —C(O)O—, —$NR^G$C(O)O—, —O—, or —$NR^G$—. Each $R_{25}$ is independently $R^G$, halo, —OH, —CN, —NO$_2$, —NH$_2$, or —OCF$_3$. Each $R^G$ is independently hydrogen or an optionally substituted heteroaryl.

$R_{24}$ is hydrogen or an oxo group.

Another aspect of the present invention provides another group of compounds, and pharmaceutically acceptable compositions thereof, that are useful as inhibitors of voltage-gated sodium channels in the treatment of disorders where activation or hyperactivity of sodium ion channels is implicated in the disease state. These compounds have formula Ic:

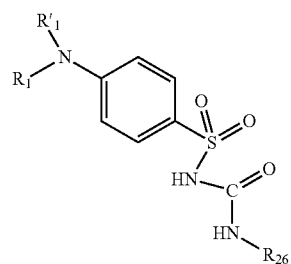

Ic or a pharmaceutically acceptable salt thereof, wherein $R'_1$ and $R_1$ are defined above in formula I.

$R_{26}$ is hydrogen or straight or branched $C_{1-5}$ aliphatic.

Another aspect of the present invention provides another group of compounds, and pharmaceutically acceptable compositions thereof, that are useful as inhibitors of voltage-gated sodium channels in the treatment of disorders where activation or hyperactivity of sodium ion channels is implicated in the disease state. These compounds have formula Id:

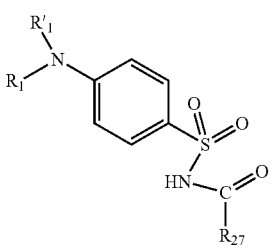

Id or a pharmaceutically acceptable salt thereof, wherein $R'_1$ and $R_1$ are defined above in formula I.

$R_{27}$ is cycloaliphatic, heterocycloaliphatic, aryl, or heteroaryl, each of which is optionally substituted.

Exemplary compounds of the present invention include, but are not limited to, those illustrated in Table 2 below.

TABLE 2
Examples of compounds of the present invention.
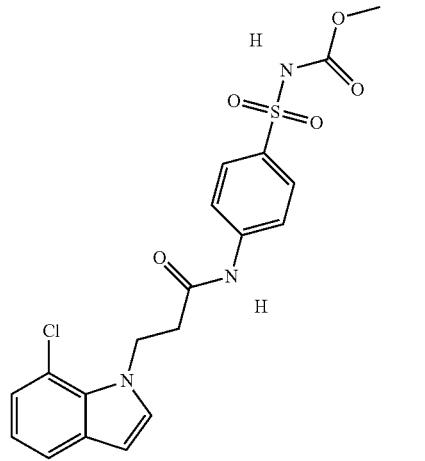
1
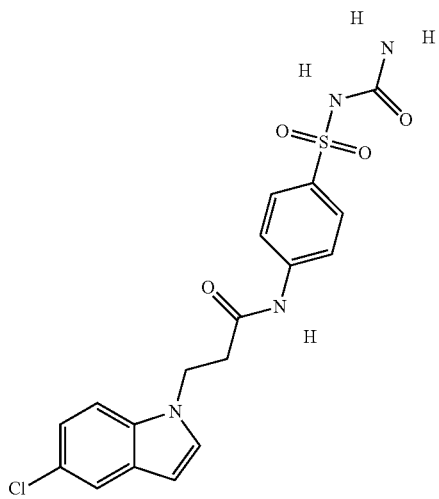
2
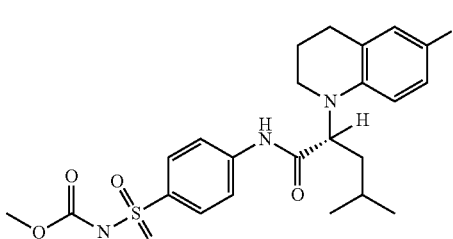
3
TABLE 2-continued
Examples of compounds of the present invention.
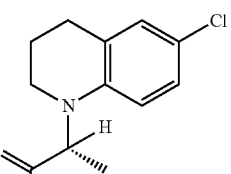
4
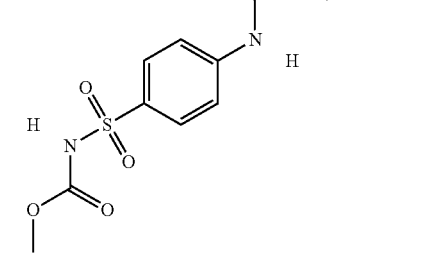
5
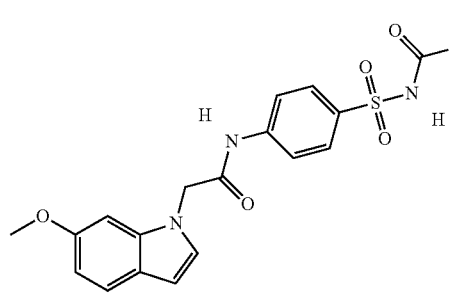
6
7

TABLE 2-continued
Examples of compounds of the present invention.
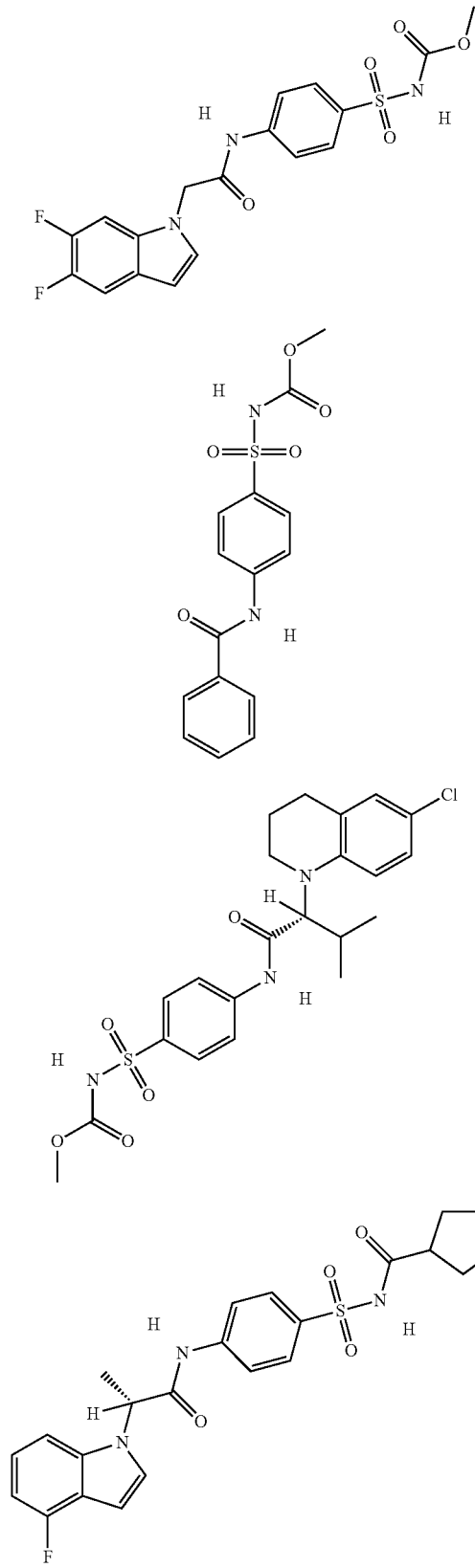
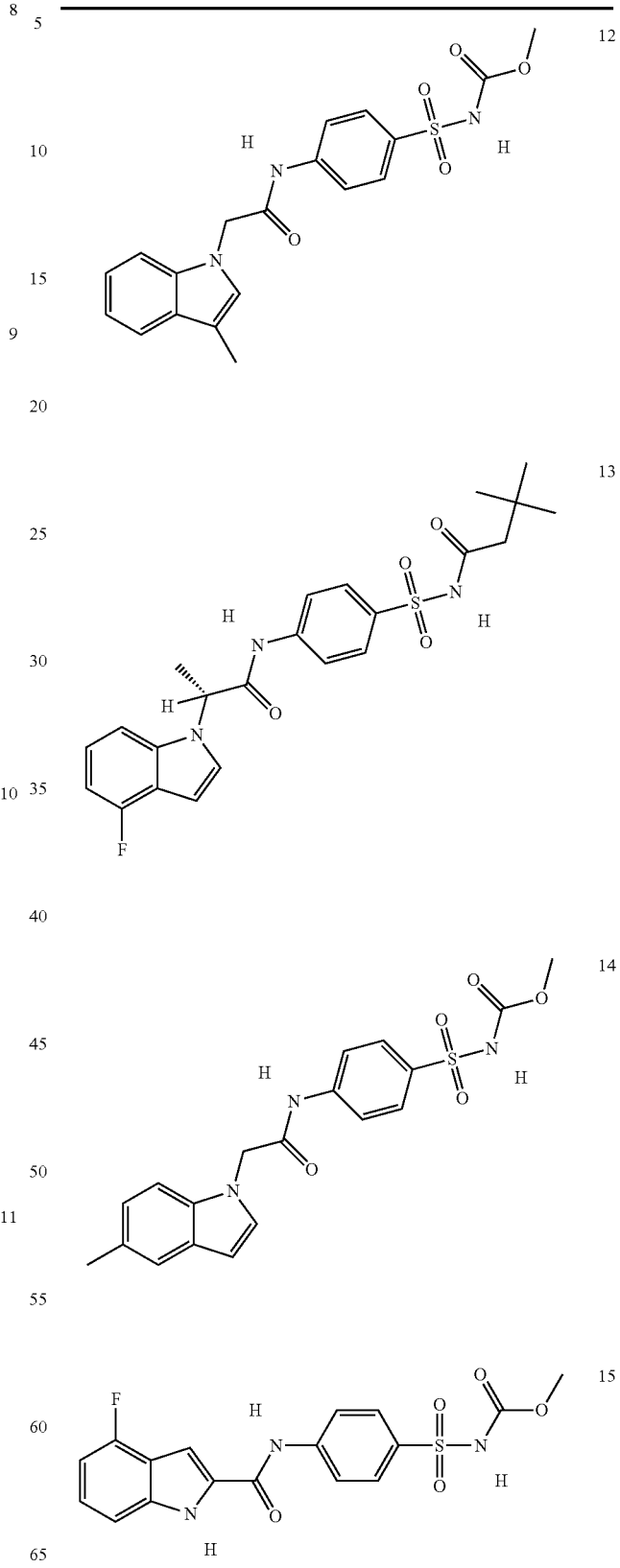

TABLE 2-continued
Examples of compounds of the present invention.
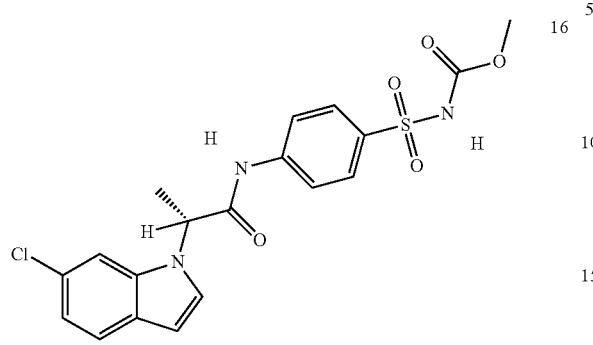
16
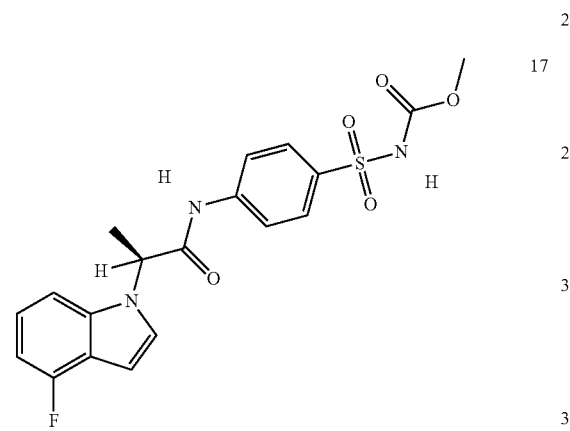
17
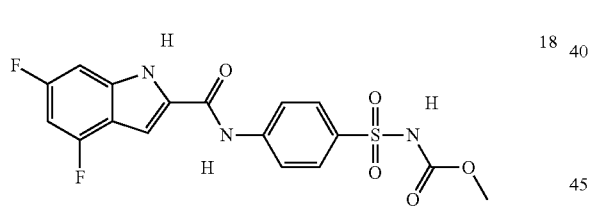
18
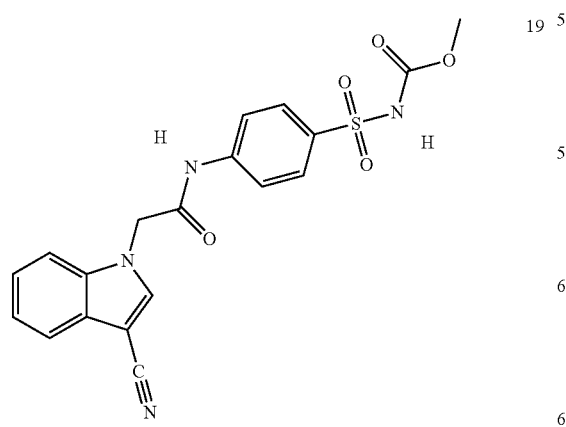
19
TABLE 2-continued
Examples of compounds of the present invention.
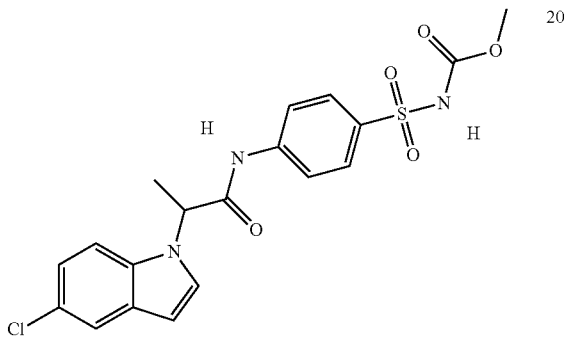
20
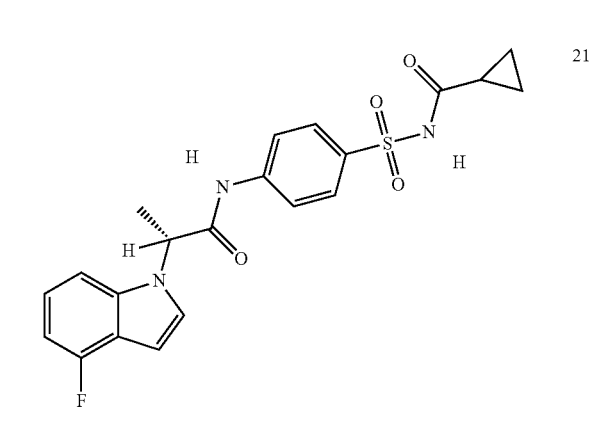
21
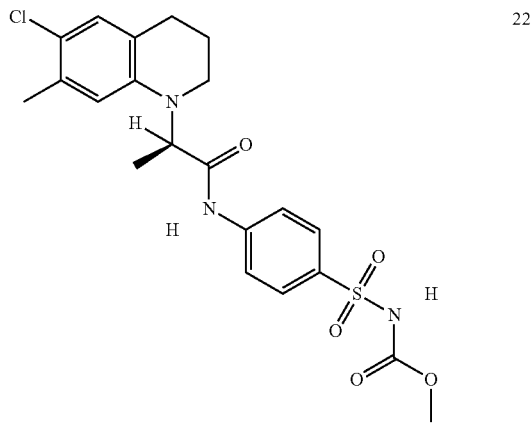
22
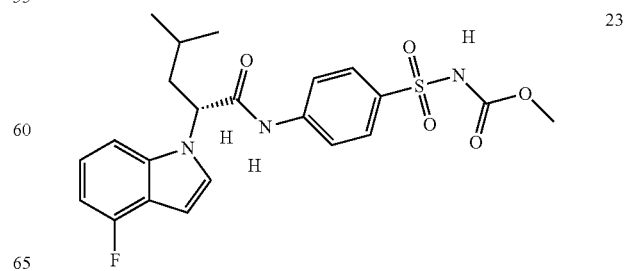
23

TABLE 2-continued
Examples of compounds of the present invention.
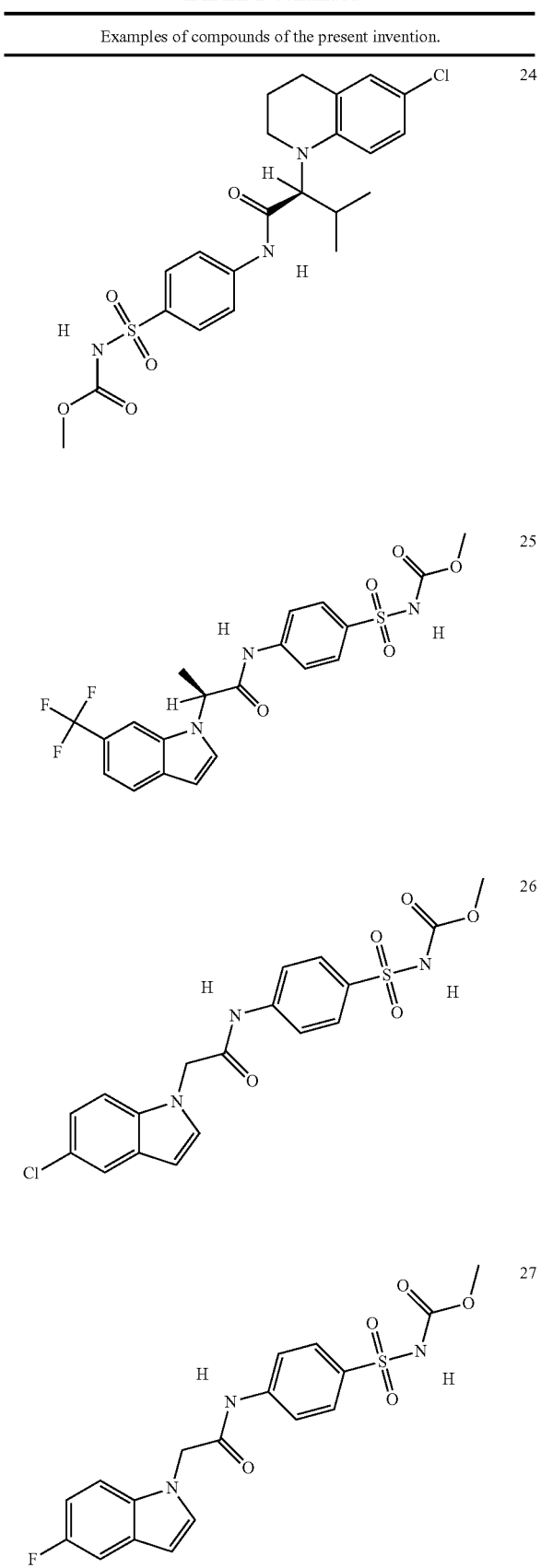
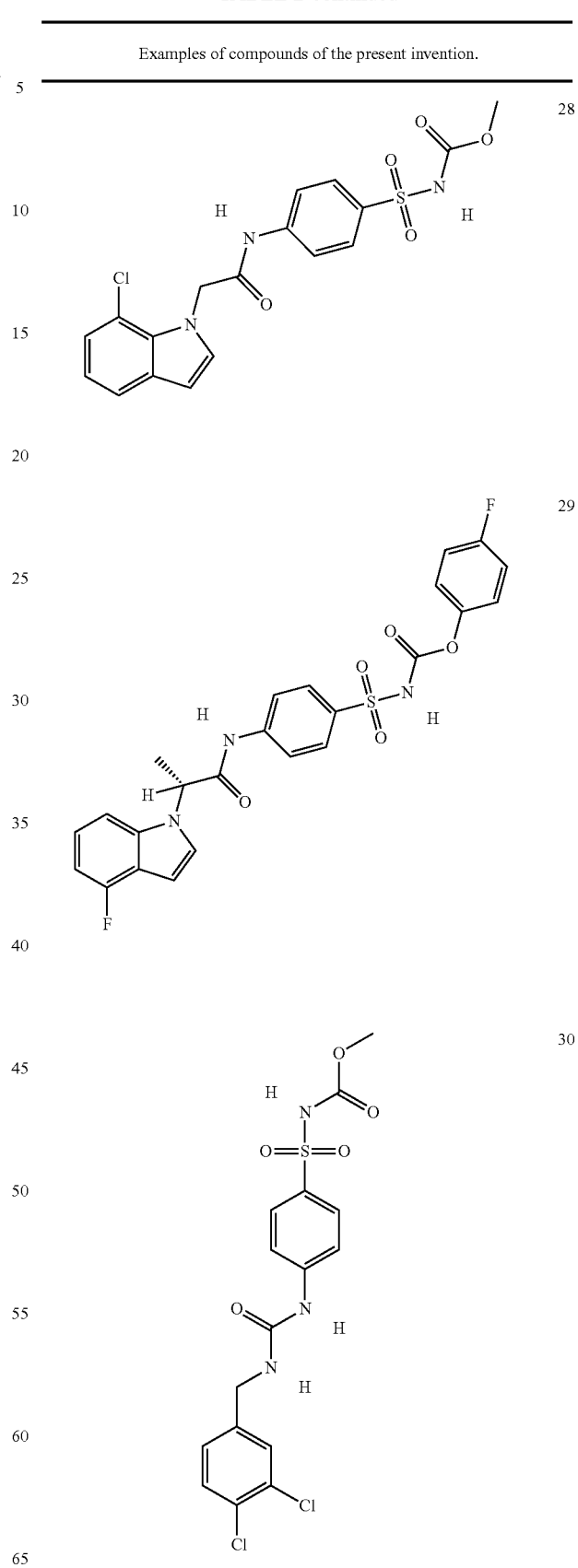

TABLE 2-continued
Examples of compounds of the present invention.
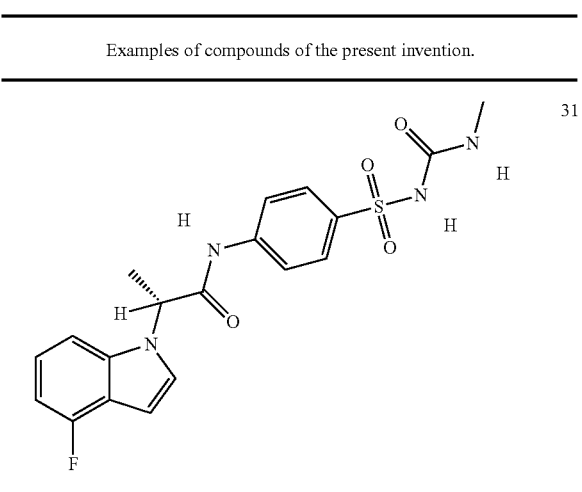
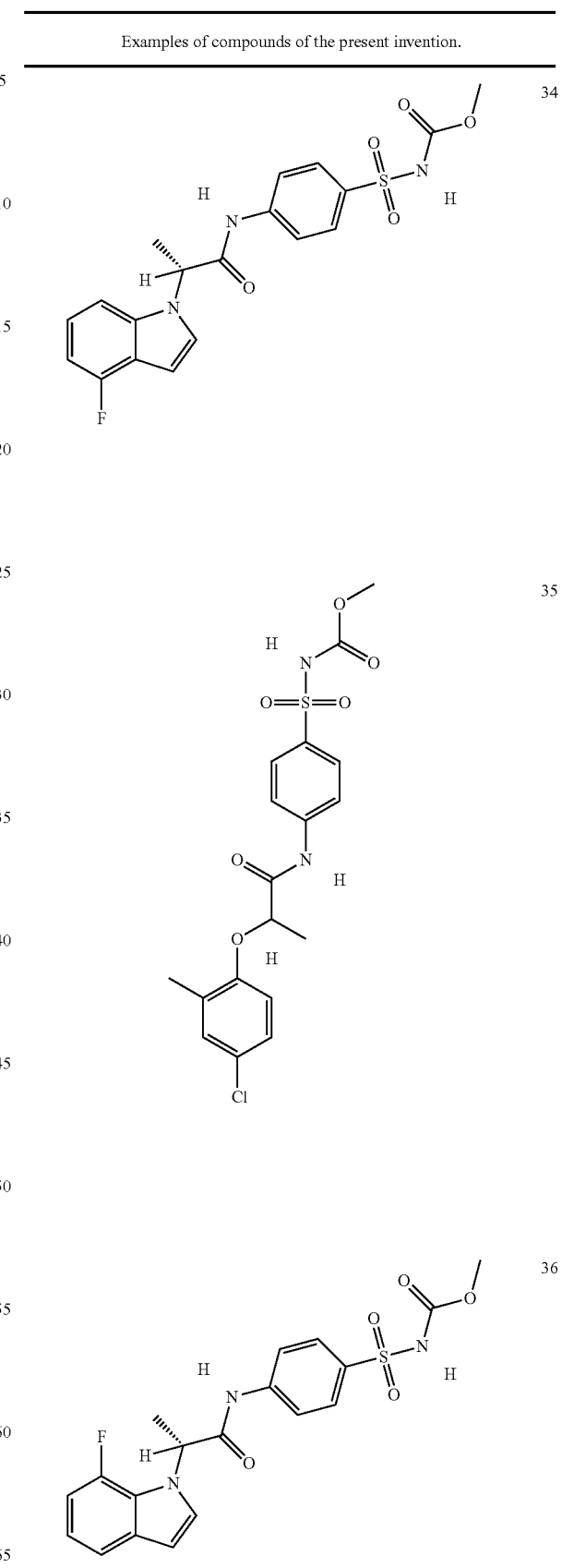

TABLE 2-continued
Examples of compounds of the present invention.
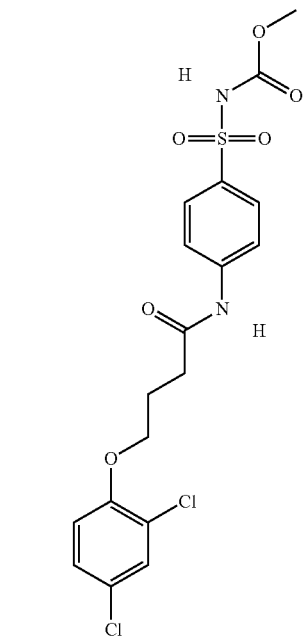
37
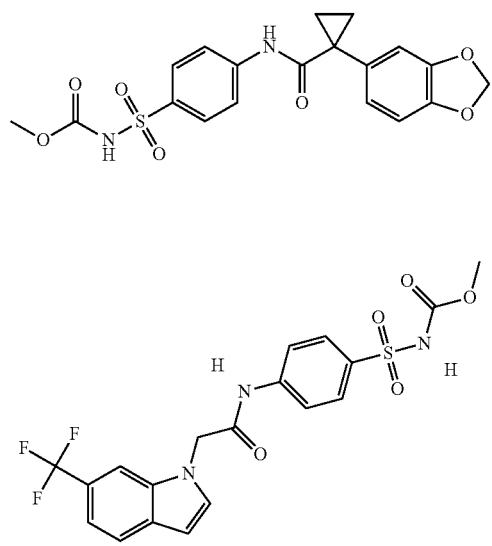
38
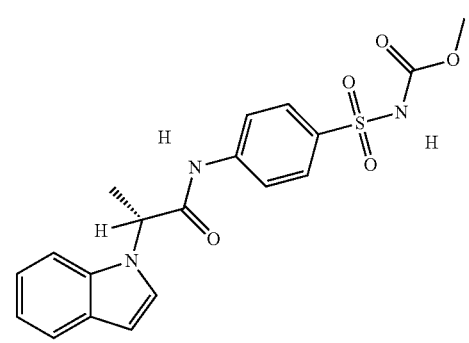
39
40
TABLE 2-continued
Examples of compounds of the present invention.
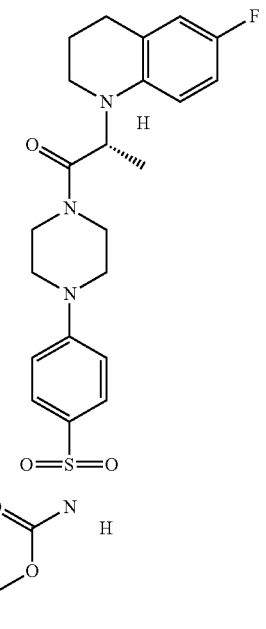
41
42
43

TABLE 2-continued
Examples of compounds of the present invention.
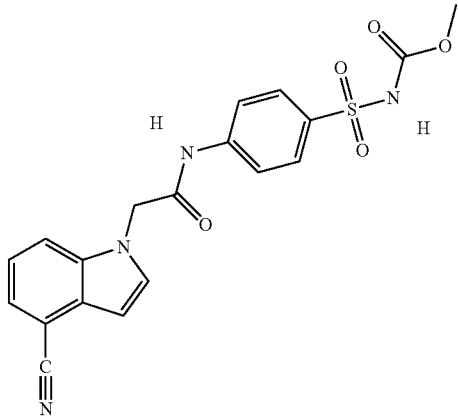
44
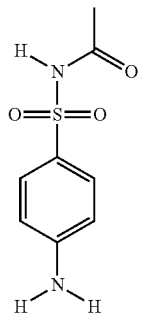
45
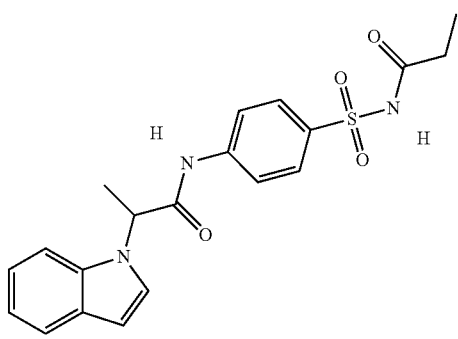
46
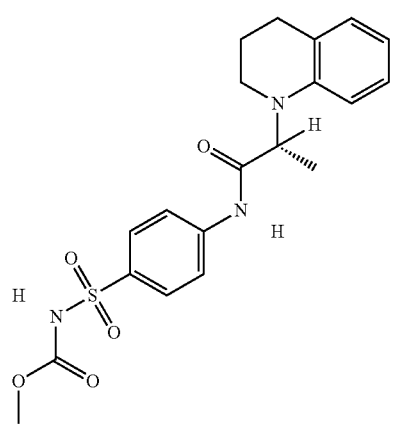
47
TABLE 2-continued
Examples of compounds of the present invention.
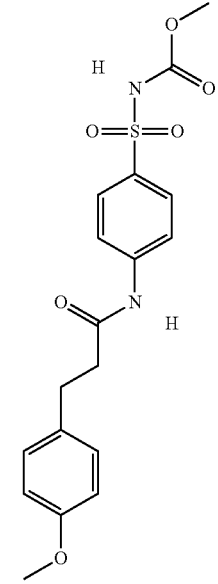
48
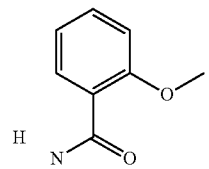
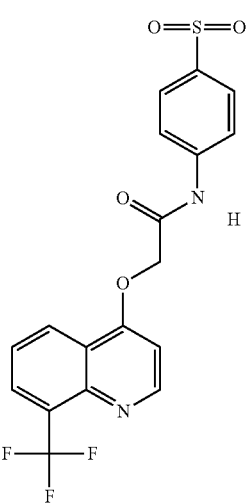
49

TABLE 2-continued
Examples of compounds of the present invention.
50 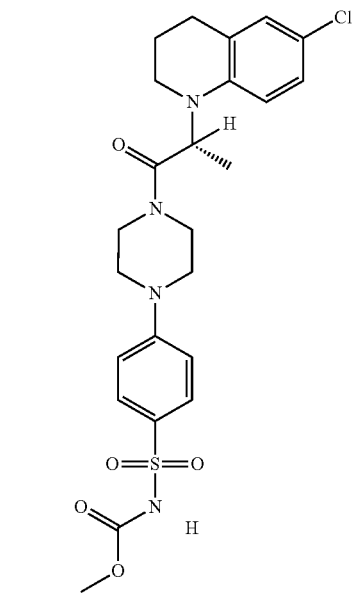
52 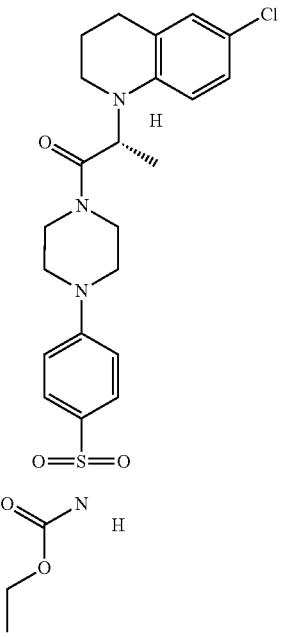
51 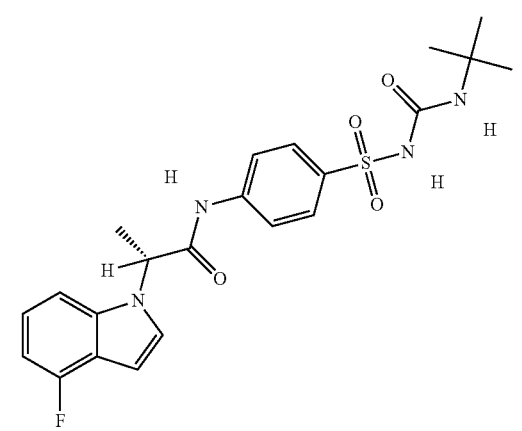
53 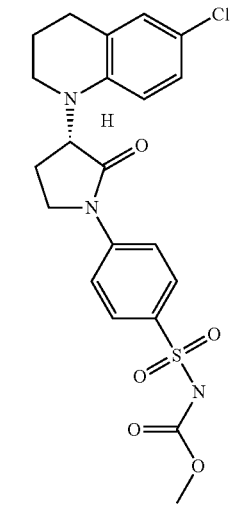
54 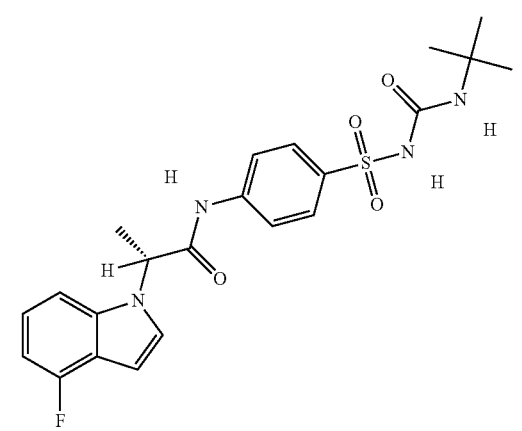

TABLE 2-continued
Examples of compounds of the present invention.
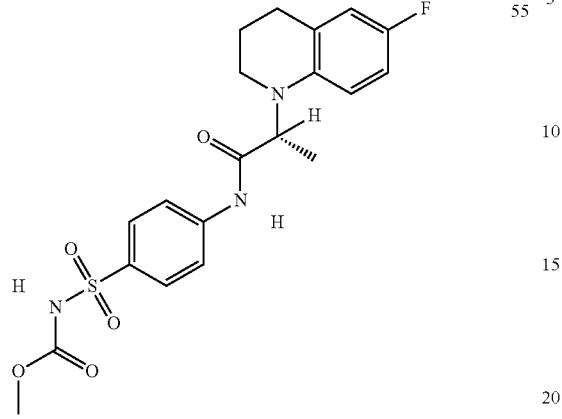
55
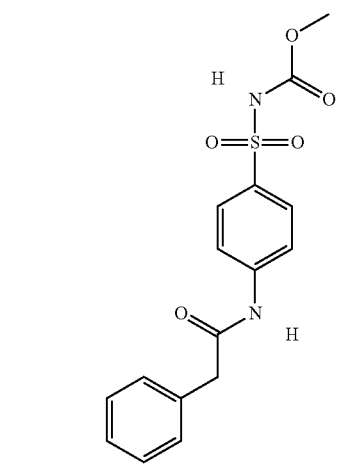
56
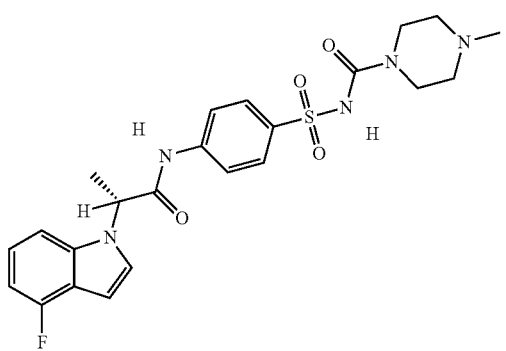
57
TABLE 2-continued
Examples of compounds of the present invention.
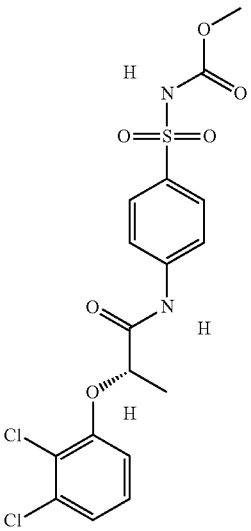
58
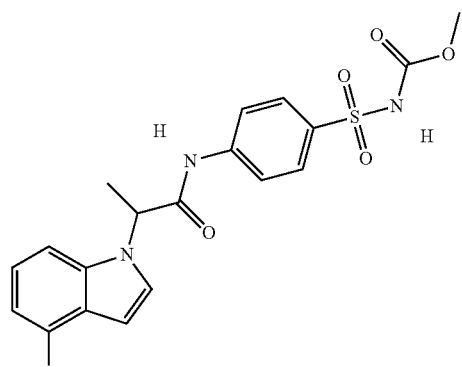
59
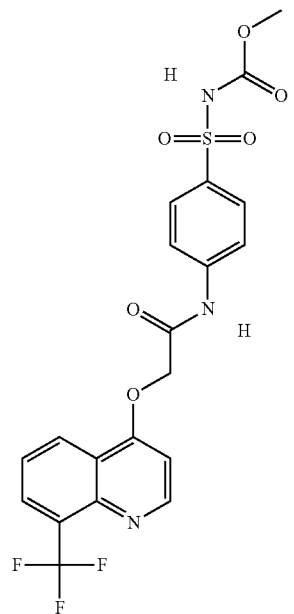
60

TABLE 2-continued
Examples of compounds of the present invention.
61 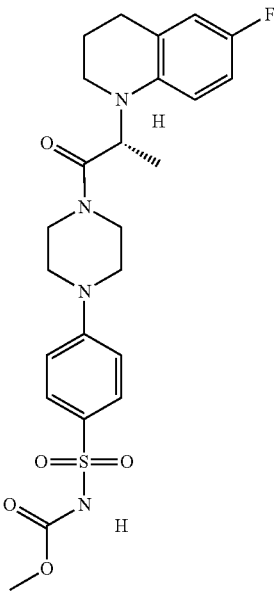
62 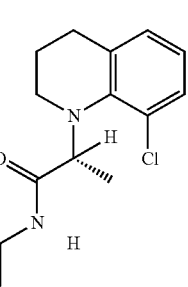
63 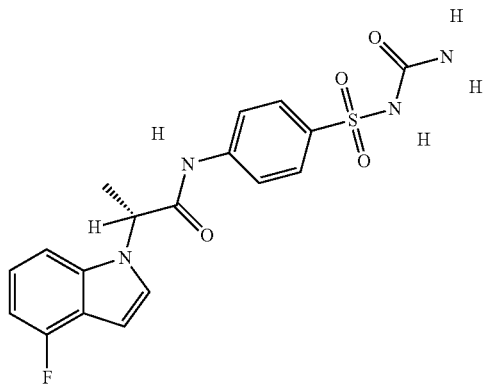
TABLE 2-continued
Examples of compounds of the present invention.
64 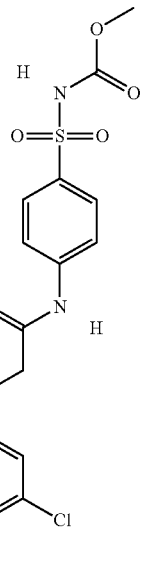
65 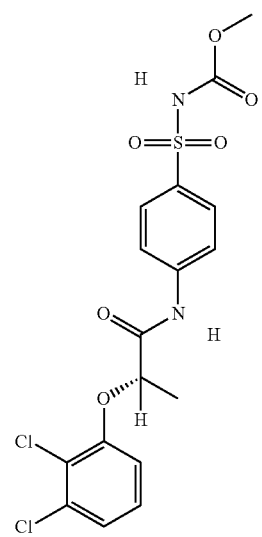
66 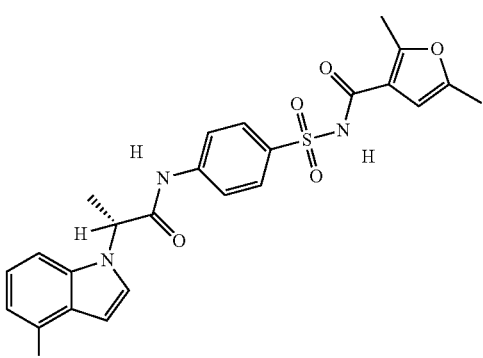

TABLE 2-continued
Examples of compounds of the present invention.
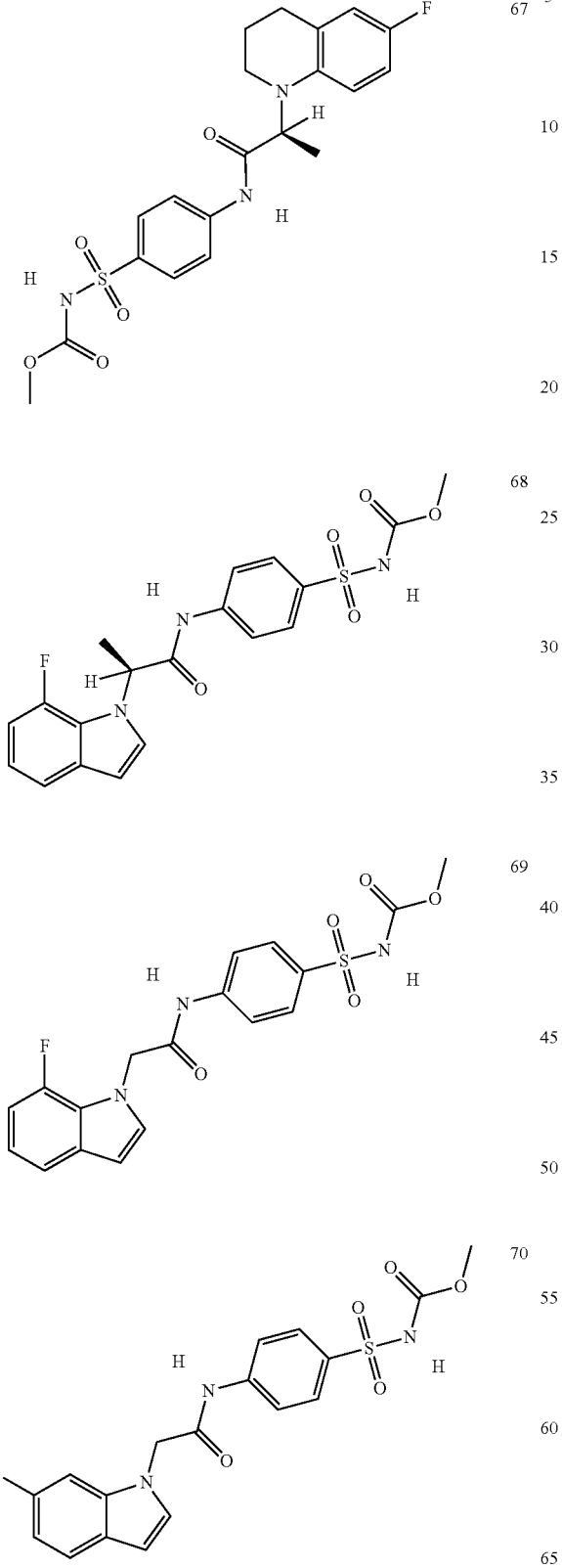
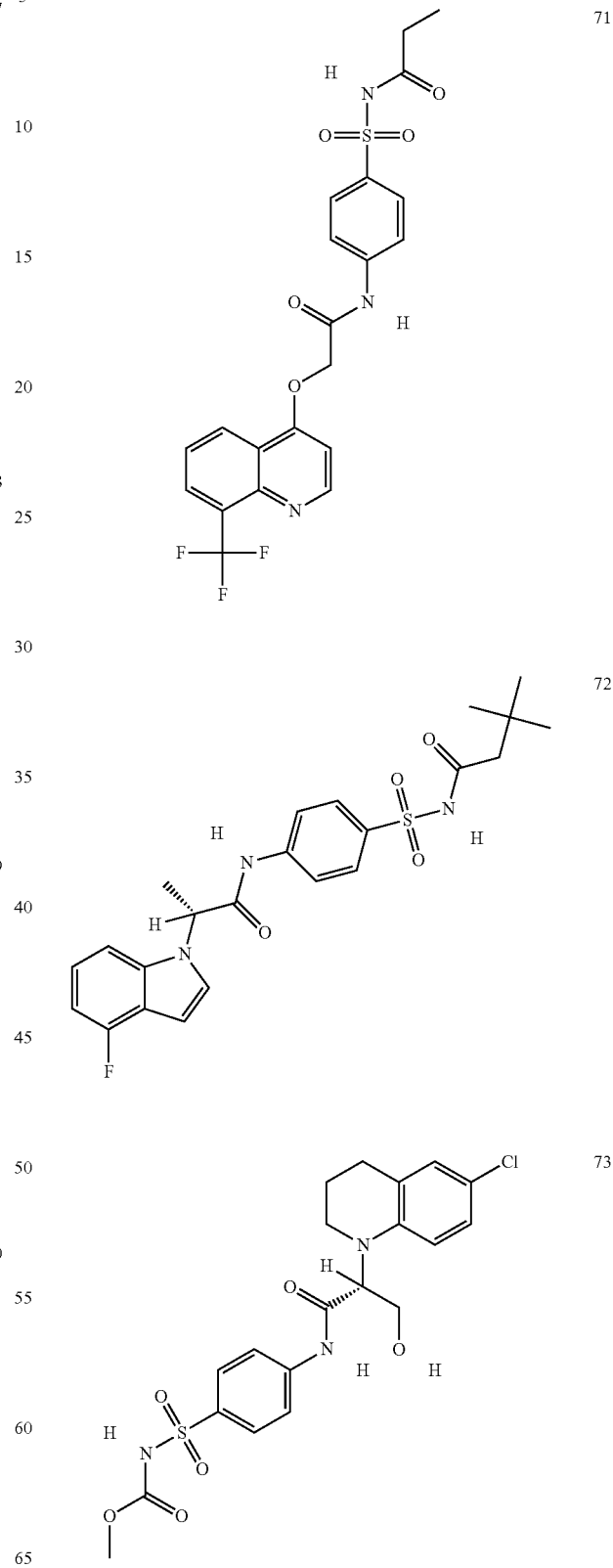

TABLE 2-continued
Examples of compounds of the present invention.
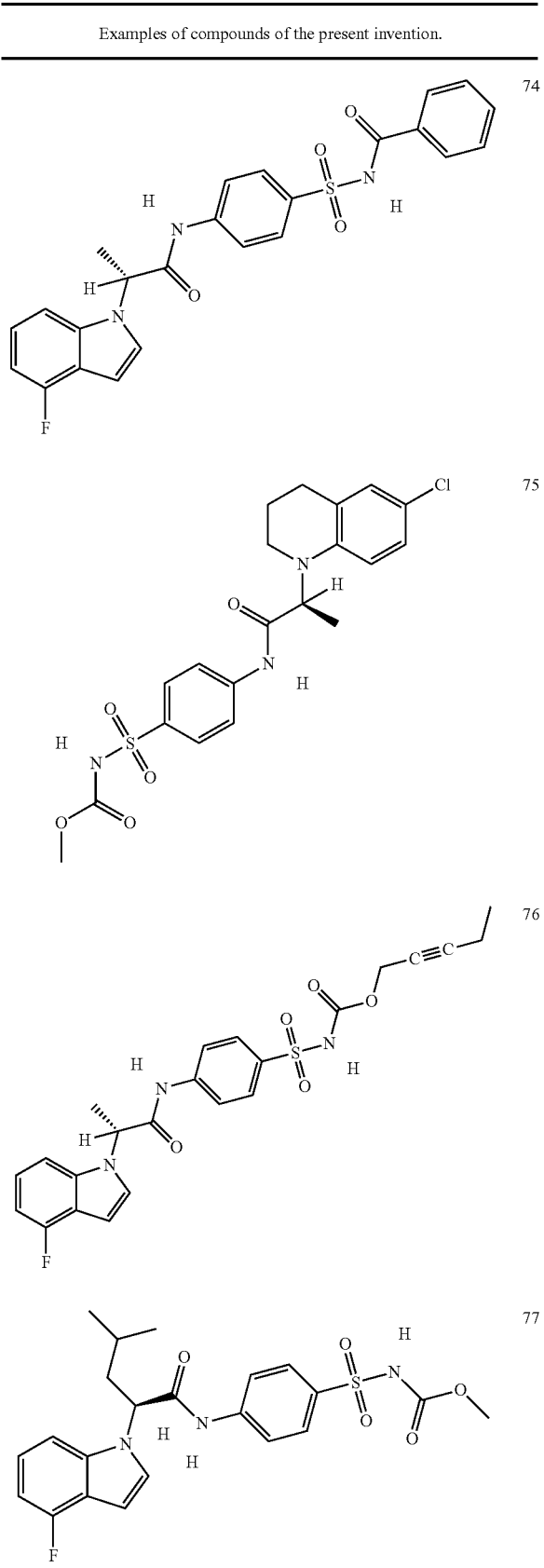

TABLE 2-continued
Examples of compounds of the present invention.
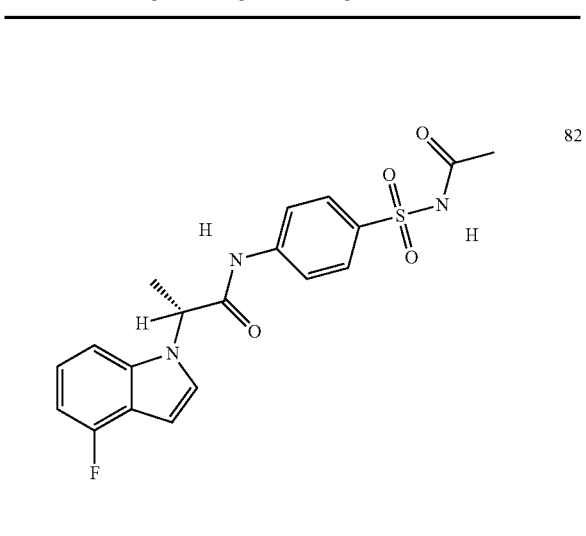 82
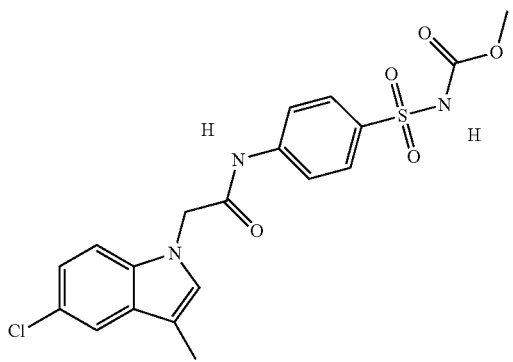 83
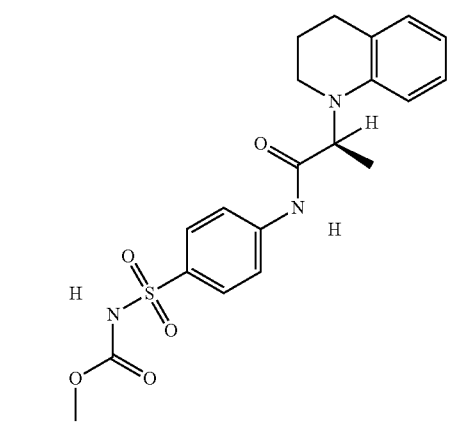 84
TABLE 2-continued
Examples of compounds of the present invention.
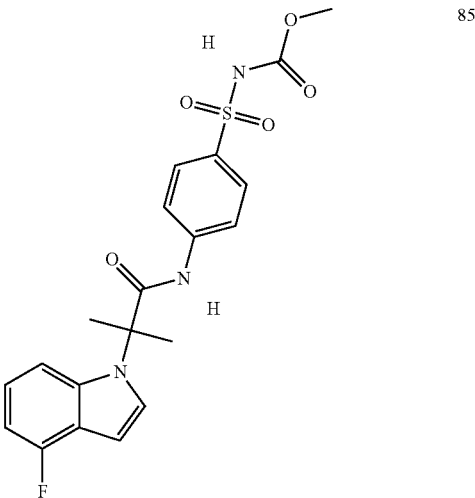 85
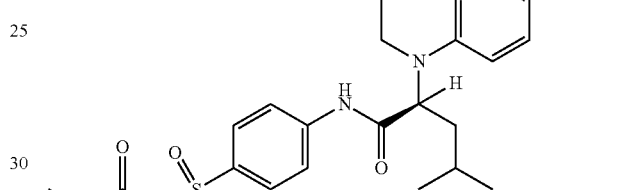 86
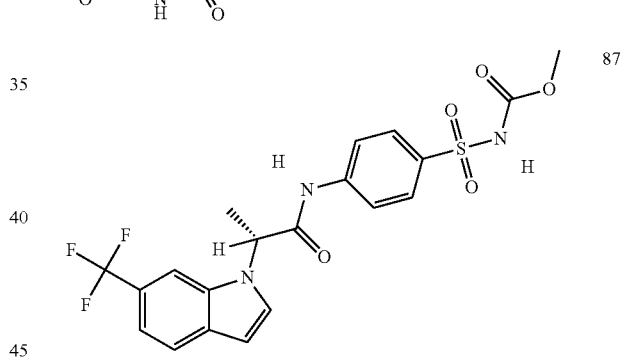 87
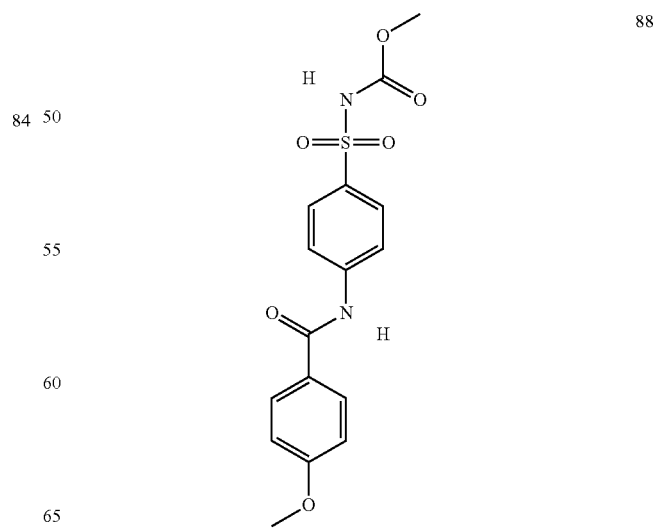 88

III. Synthetic Schemes

Compounds of the invention may be prepared by well-known methods in the art. Exemplary methods are illustrated below in Schemes 1-14.

In one method, compounds of the invention wherein $R_1$ is —C(O)$R_4$ may be prepared as illustrated in Scheme 1.

Scheme 1:

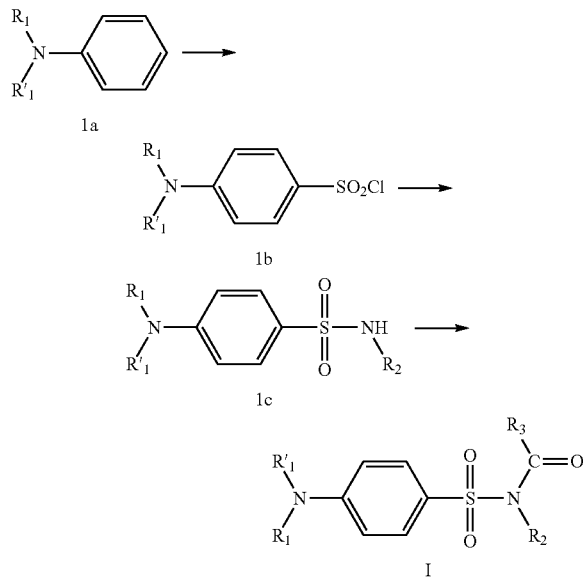

Referring to Scheme 1, the aniline 1a reacts with excess chlorosulfonyl chloride under known conditions to provide the sulfonyl chloride 1b. Reaction of 1b with excess amine $R_2NH_2$, optionally in the presence of a tertiary amine, provides the sulfonamide 1c. Reaction of 1c with an activated carboxy derivative, for example a chloroformate, an acyl halide, an isocyanate or an anhydride, in the presence of a tertiary base such as, for example, triethylamine, provides the inventive compounds I.

Alternatively, compounds of the invention I may be prepared as illustrated in Scheme 2.

Scheme 2:

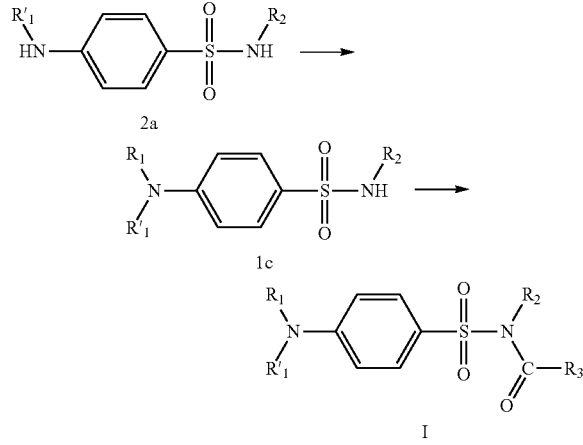

Referring to Scheme 2, the aminosulfonamide 2a is treated with an activated carboxy derivative, for example a chloroformate, an acyl halide, an isocyanate or an anhydride, in the presence of a tertiary base such as, for example, triethylamine, to provide the sulfonamide 1c. Acylation of 2b as described in Scheme 1 provides the inventive compounds.

Alternatively, compounds of the invention I may be prepared as illustrated in Scheme 3.

Scheme 3:

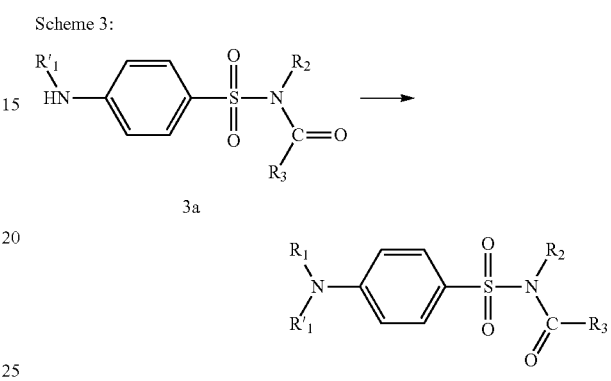

Referring to Scheme 3, acylation of the sulfonamide 3a by methods described in Schemes 1 and 2 provides compounds of the invention I.

In one method, compounds of the invention I wherein $R_1$ is —C(O)$R_4$ may be prepared as illustrated in Scheme 4.

Scheme 4:

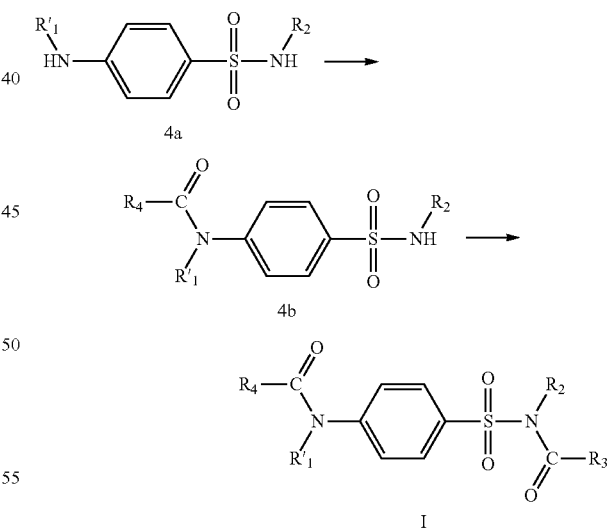

Referring to Scheme 4, the aminosulfonamide 4a is treated with an activated carboxy derivative, for example a chloroformate, an acyl halide, an isocyanate or an anhydride, in the presence of a tertiary base such as, for example, triethylamine, to provide the sulfonamide 4b. Acylation of 4b, as described in Scheme 1, provides the inventive compounds.

Alternatively, compounds of the invention I wherein $R_1$ is —C(O)$R_4$ may be prepared as illustrated in Scheme 5.

Scheme 5:

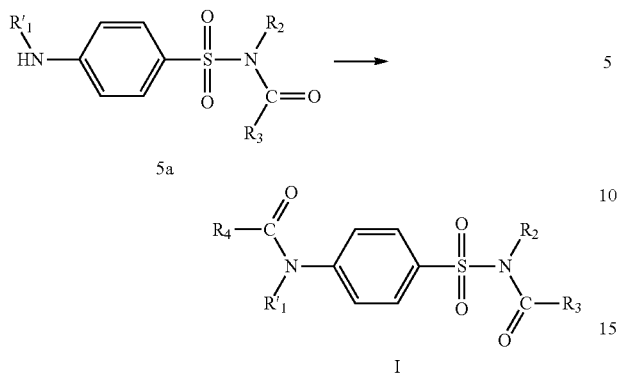

Alternatively, compounds of the invention I wherein $R_1$ is —C(O)$R_4$ may be prepared as illustrated in Scheme 6.

Scheme 6:

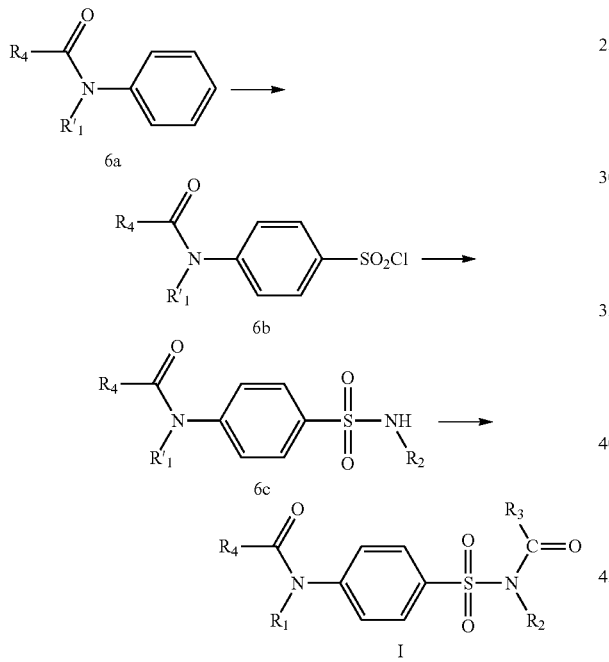

Referring to Scheme 6, the acyl aniline 6a is treated with chlorsulfonyl chloride to provide the sulfonyl chloride 6b which reacts with an amine $R_2NH_2$, optionally in the presence of a tertiary base, to provide the sulfonamide 6c. Acylation of 6c as previously described provides inventive compounds I.

Compounds of the invention Ia may be prepared as illustrated in Scheme 7.

Scheme 7:

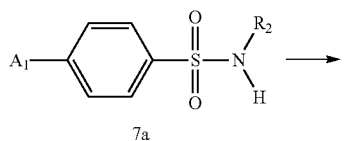

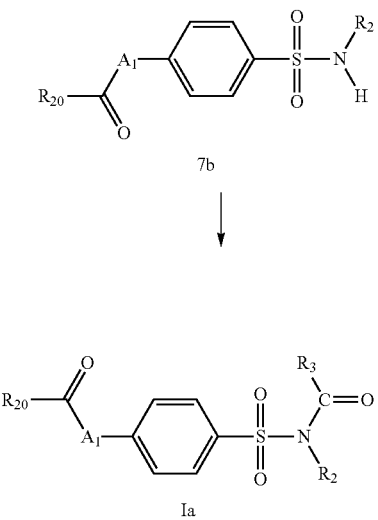

Referring to Scheme 7, the sulfonamide 7a is treated with an activated carboxy derivative, for example a chloroformate, an acyl halide, an isocyanate or an anhydride, in the presence of a tertiary base such as, for example, triethylamine, to provide the sulfonamide 7b. Acylation of 7b as described in Scheme 1 provides the inventive compounds.

Alternatively, compounds of the invention Ia may be prepared as illustrated in Scheme 8.

Scheme 8:

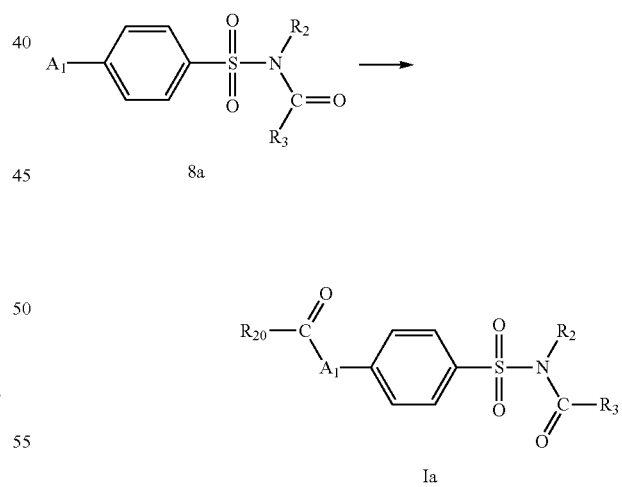

Referring to Scheme 8, the sulfonamide 8a is treated with an activated $R_{20}$ carboxy derivative, for example a chloroformate, an acyl halide, an isocyanate or an anhydride, in the presence of a tertiary base such as, for example, triethylamine, to provide the inventive compounds Ia.

Alternatively, compounds of the invention Ia may be prepared as illustrated in Scheme 9.

Scheme 9:

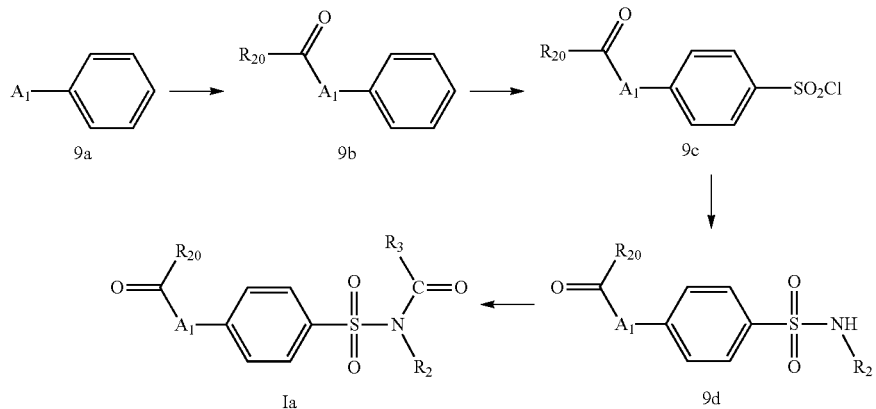

Referring to Scheme 9, the aniline 9a is acylated with an activated $R_{20}$ carboxy derivative, for example a chloroformate, an acyl halide, an isocyanate or an anhydride, in the presence of a tertiary base such as, for example, triethylamine, to provide 9b. Reaction of 9b with chlorosulfonyl chloride under known conditions provides the sulfonyl chloride 9c. Reaction of 9c with excess amine $R_2NH_2$, optionally in the presence of a tertiary amine, provides the sulfonamide 9d. Reaction of 9d with an activated carboxy derivative, for example a chloroformate, an acyl halide, an isocyanate or an anhydride, in the presence of a tertiary base such as, for example, triethylamine, provides the inventive compounds Ia.

Compounds of the invention Ib wherein $R_{23}$ is —C(O)$R_{25}$ may be prepared as illustrated in Scheme 10.

Referring to Scheme 10, Reaction of 10a with an activated $R_{25}$ carboxy derivative, for example a chloroformate, an acyl halide, an isocyanate or an anhydride, in the presence of a tertiary base such as, for example, triethylamine, provides 10b which reacts with chlorosulfonyl chloride to provide the sulfonyl chloride 10c. Reaction of 10c with amine $R_2NH_2$, optionally in the presence of a tertiary amine, provides the sulfonamide 10d. Reaction of 10d with an activated carboxy derivative, for example a chloroformate, an acyl halide, an isocyanate or an anhydride, in the presence of a tertiary base such as, for example, triethylamine, provides the inventive compounds Ib.

Alternatively, compounds of the invention Ib may be prepared as illustrated in Scheme 11.

Scheme 10:

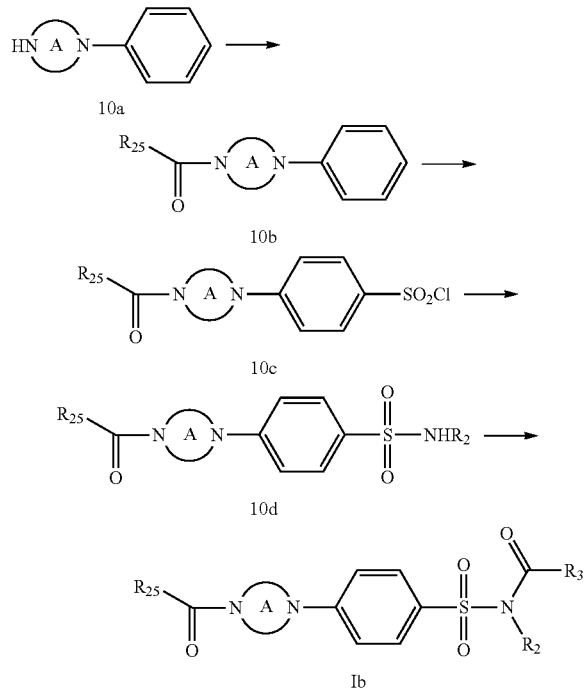

Scheme 11:

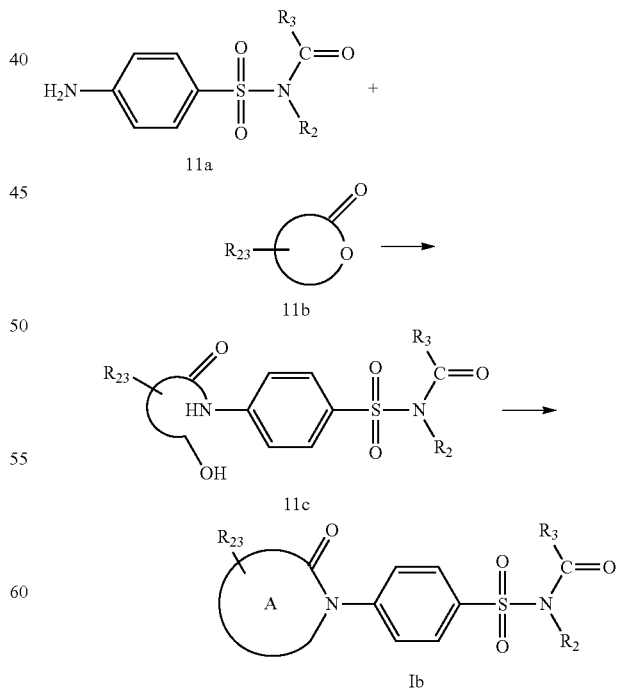

Referring to Scheme 11, the sulfonamide 11a reacts with a lactone 11b in the presence of trimethylaluminum to provide the intermediate 11c. Cyclization of 11c with di-tert-butylazodicarboxylate and tributylphosphine provides compounds of the invention Ib.

Compounds of the invention Ic may be prepared as illustrated in Scheme 12.

Scheme 12:

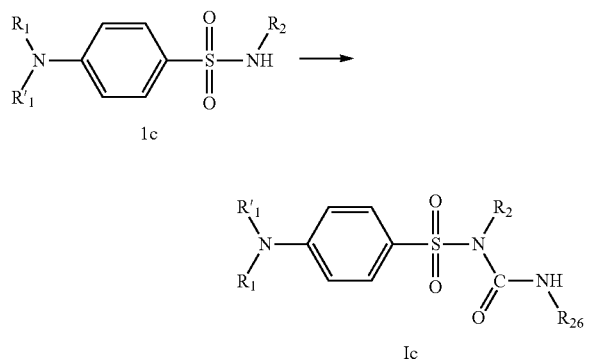

Referring to Scheme 12, the sulfonamide 1c reacts with an isocyanate in the presence of potassium carbonate in a polar solvent such as, for example, N-methylpyrrolidone to provide compounds of the invention Ic.

Compounds of the invention Id may be prepared as illustrated in Scheme 13.

Scheme 13:

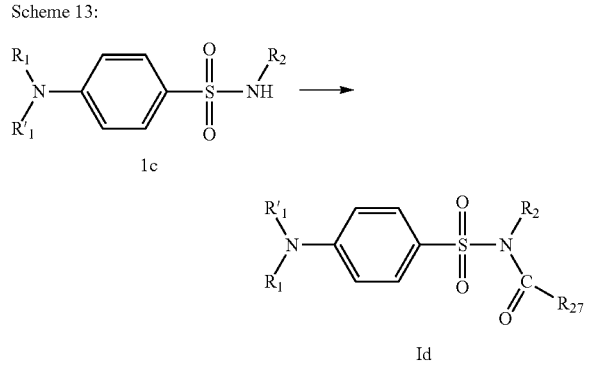

Referring to Scheme 13, the sulfonamide 1c reacts with an acid chloride in the presence of potassium carbonate in a polar solvent such as, for example, N-methylpyrrolidone to provide compounds of the invention Id.

Alternatively, compounds of the invention Id, wherein $R_1$ is an acyl group, may be prepared as illustrated in Scheme 14.

Scheme 14:

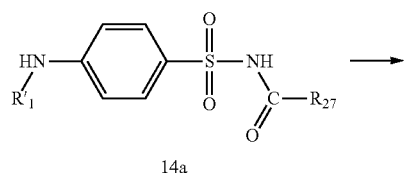

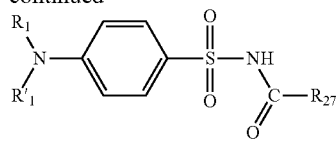

Reaction of 14a with an activated $R_1$ carboxy derivative, for example a chloroformate, an acyl halide, an isocyanate or an anhydride, in the presence of a tertiary base such as, for example, triethylamine, provides the inventive compounds Id.

IV. Formulations, Administrations, and Uses

A. Pharmaceutically Acceptable Compositions

As discussed above, the present invention provides compounds that are inhibitors of voltage-gated sodium ion channels and/or calcium channels, and thus the present compounds are useful for the treatment of diseases, disorders, and conditions including, but not limited to acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel or calcium channel.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

B. Uses of Compounds and Pharmaceutically Acceptable Compositions

In yet another aspect, a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the present invention, may be administered using any amount and any route of administration effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitus or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form", as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.3.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

V. Preparations and Examples

Step 1: (S)-Ethyl 2-(trifluoromethylsulfonyloxy)propanoate

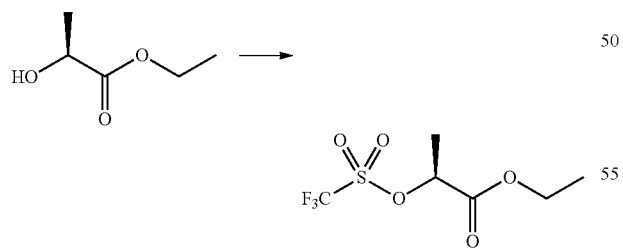

Under an $N_2$ atmosphere, at −30° C., triflic anhydride (24.2 mL, 144 mmol) was slowly added to a stirring solution of (S)-ethyl 2-hydroxypropanoate (15 mL, 131 mmol) in $CH_2Cl_2$ (300 mL). After stirring the reaction mixture for 10 minutes, 2,6-lutidine (17.5 mL, 151 mmol) was added. The reaction was stirred at room temperature for 16 h. The reaction mixture was filtered over a small silica pad and washed with ethyl acetate and hexane (1:4, 400 mL). The solution was concentrated using a bath temperature of 20° C. and vacuum greater than 50 mm Hg to obtain the desired triflate as a red oil (32.7 g).

Step 2: (R)-Ethyl 2-(6-fluoro-3,4-dihydroquinolin-1(2H)-yl)-3-methylproanoate

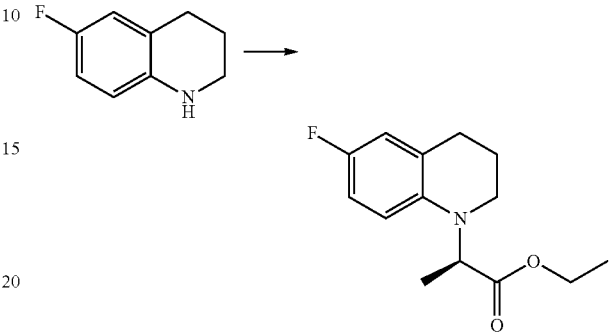

(S)-ethyl 2-(trifluoromethylsulfonyloxy)propanoate (10.9 g, 44 mmol), was slowly added to a stirring solution of 6-fluoro-1,2,3,4-tetrahydroquinoline (6.1 g, 40 mmol), 2,6-lutidine (5.3 mL, 46 mmol), and 1,2-dichloroethane (100 mL), under $N_2$, at 25° C. The reaction was heated at 70° C. for 19 h. The mixture was washed with $H_2O$ and extracted twice with $CH_2Cl_2$. The organic layer was dried over $MgSO_4$, filtered, and concentrated. The residue was purified by silica gel chromatography using 0-20% EtOAc in hexanes gave the desired ester as a yellow oil (12.9 g). LC/MS (10%-99% $CH_3CN$ (0.035% TFA)/$H_2O$ (0.05% TFA), m/z: M+1 obs=251.8; $t_R$=3.68 min.

Step 3: (R)-2-(6-fluoro-3,4-dihydroquinolin-1(2H)-yl)-3-methylpropanoic acid

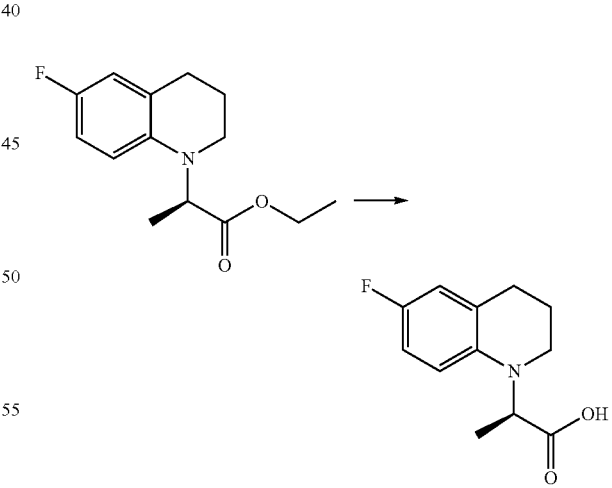

At 0° C., an aqueous 2.0 M KOH solution (15.9 mL, 31.8 mmol) was added to a stirring solution of (R)-2-(6-fluoro-3,4-dihydroquinolin-1(2H)-yl)-3-methylpropanoate (2.0 g, 7.96 mmol) in MeOH (16 mL). The reaction was allowed to warm up to RT and left stirring overnight. Due to the instability of the final product as a solid, the solution containing (R)-2-(6-fluoro-3,4-dihydroquinolin-1(2H)-yl)-3-methylbutanoic acid was used for the next step without further work up.

LC/MS (10%-99% CH₃CN (0.035% TFA)/H₂O (0.05% TFA), m/z: M+1 obs=223.24; $t_R$=2.92 min.

Step 4: (R)-2-(6-fluoro-3,4-dihydroquinolin-1(2H)-yl)-1-(4-phenylpiperazin-1-yl)propan-1-one

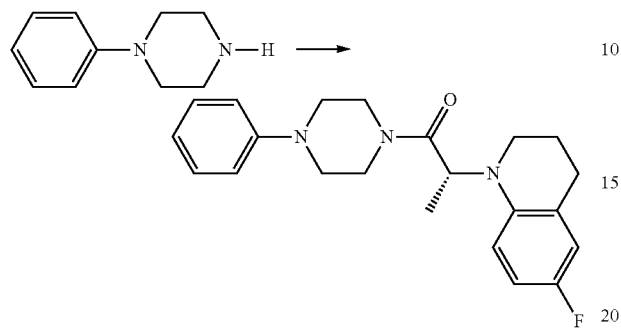

The (R)-2-(6-fluoro-3,4-dihydroquinolin-1(2H)-yl)propanoic acid (7.9 mmol), 1-phenyl piperazine (1.2 mL, 7.9 mmol), HATU (3.0 g, 7.9 mmol), NaHCO₃ (660 mg, 7.9 mmol) and CH₂Cl₂ (10 mL): DMF (10 ml) were stirred at rt for 19 h. The solution was poured into an ice-water mixture (100 ml), followed by an extraction with CH₂Cl₂ (3×75 mL). The organic layer was dried over MgSO₄ and evaporated in vacuo. After evaporating the solvents under reduced pressure, the residue was purified by silica gel chromatography using 20-50% ethyl acetate in hexane gave (R)-2-(6-fluoro-3,4-dihydroquinolin-1(2H)-yl)-1-(4-phenylpiperazin-1-yl)propan-1-one (1.96 g) as white solid. LC/MS (10%-99% CH₃CN (0.035% TFA)/H₂O (0.05% TFA)), m/z: M+1 obs=369.47; $t_R$=3.36 min.

Step 5: (R)-4-(4-(2-(6-fluoro-3,4-dihydroquinolin-1(2H)-yl)propanoyl)piperazin-1-yl)benzene-1-sulfonyl chloride

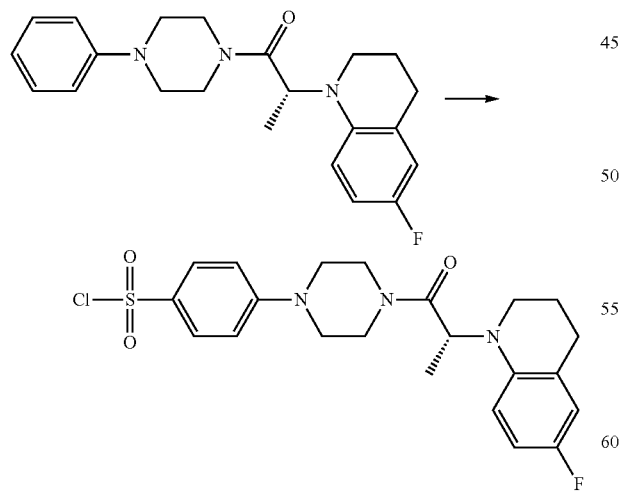

After cooling chlorosulfonic acid (5.5 ml, 3 eq) to 0° C. under N₂, (R)-2-(6-fluoro-3,4-dihydroquinolin-1(2H)-yl)-1-(4-phenylpiperazin-1-yl)propan-1-one (1 g, 2.72 mmol) was added and then allowed to warm up to rt. The solution was poured into an ice-water mixture (250 ml), followed by an extraction with CH₂Cl₂ (3×100 mL). The organic layer was dried over MgSO₄ and evaporated in vacuo. The crude product was used without further purification for next step. LC/MS (10%-99% CH₃CN (0.035% TFA)/H₂O (0.05% TFA)), m/z: M+1 obs=466.3; $t_R$=3.49 min.

Step 6: (R)-4-(4-(2-(6-fluoro-3,4-dihydroquinolin-1(2H)-yl)propanoyl)piperazin-1-yl)benzenesulphonamide

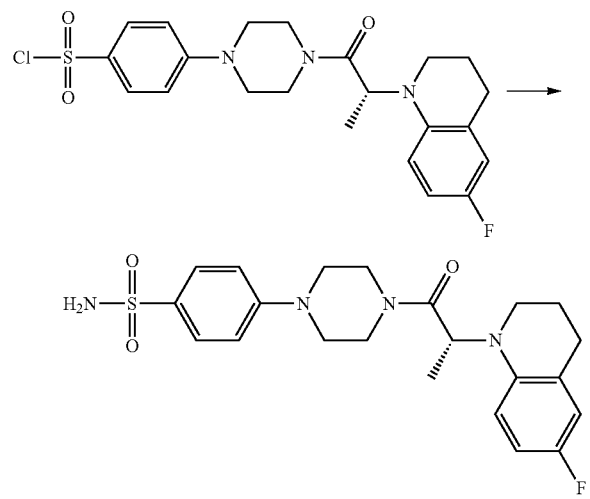

Ammonium hydroxide (28-30% solution, 7.5 mL) was added dropwise to a solution of the (R)-4-(4-(2-(6-fluoro-3,4-dihydroquinolin-1(2H)-yl)propanoyl)piperazin-1-yl)benzene-1-sulfonyl chloride (375 mg, 0.56 mmol) in acetonitrile (5 mL) at 0° C. The reaction mixture was stirred at 0° C. for 4 h. The solution was cooled to 0° C. and aqueous 1.0 M HCl was added dropwise. The reaction mixture was extracted with CH₂Cl₂ (3×50 mL). The combined organic phases were dried over MgSO₄. After evaporating the solvents under reduced pressure, the residue was purified by silica gel chromatography using 2-10% methanol in CH₂Cl₂ to give (R)-4-(4-(2-(6-fluoro-3,4-dihydroquinolin-1(2H)-yl)propanoyl)piperazin-1-yl)benzene sulfonamide as colourless oil (94 mg). LC/MS (10%-99% CH₃CN (0.035% TFA)/H₂O (0.05% TFA)), m/z: M+1 obs=447.1; $t_R$=2.68 min.

General Procedure 1

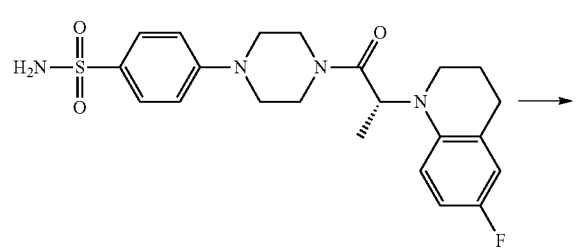

-continued

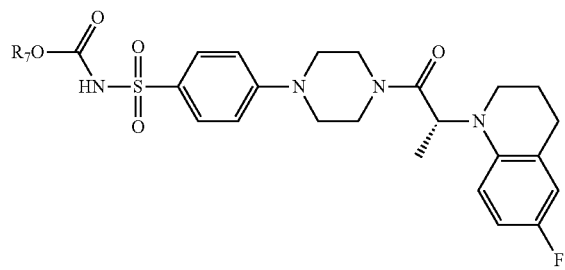

A solution of the sulfonamide (0.07 mmol) and triethyl amine (2.0-3.0 equivalent, 0.18 mmol) in acetonitrile (0.15 M-0.25 M) was stirred under an $N_2$ atmosphere. To this was added the appropriate chloroformate (1.5 equivalent, 0.11 mmol) and the mixture stirred at RT for 19 h. The mixture was concentrated and the residue purified by reverse phase HPLC using 10%-99% $CH_3CN$ (0.035% TFA)/$H_2O$ (0.05% TFA) to give the desired product.

Example 1

(R)-methyl 4-(4-(2-(6-fluoro-3,4-dihydroquinolin-1 (2H)-yl)propanoyl)piperazin-1-yl)phenylsulfonylcarbamate

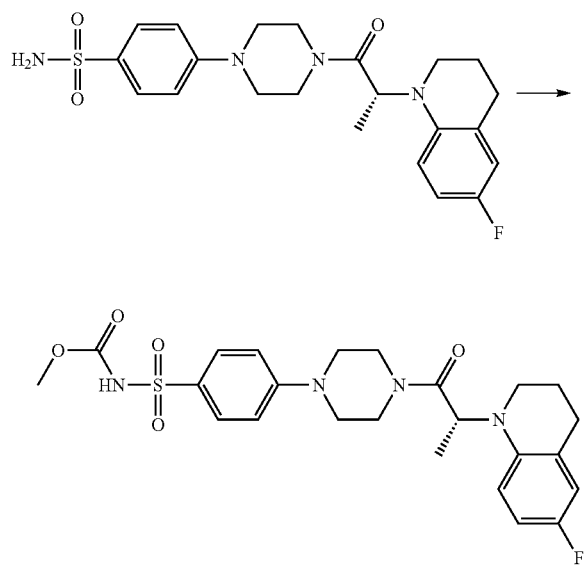

Synthesized according to General Procedure 1. The reaction was set-up with 0.07 mmol of (R)-4-(4-(2-(6-fluoro-3,4-dihydroquinolin-1(2H)-yl)propanoyl)piperazin-1-yl)benzene sulfonamide, 0.18 mmol of triethyl amine, 0.11 mmol of methyl chloroformate and 0.75 mL of acetonitrile. LC/MS (10%-99% $CH_3CN$ (0.035% TFA)/$H_2O$ (0.05% TFA)), m/z: M+1 obs=505.3; $t_R$=2.28 min.

Example 2

(R)-ethyl 4-(4-(2-(6-fluoro-3,4-dihydroquinolin-1 (2H)-yl)propanoyl)piperazin-1-yl)phenylsulfonylcarbamate

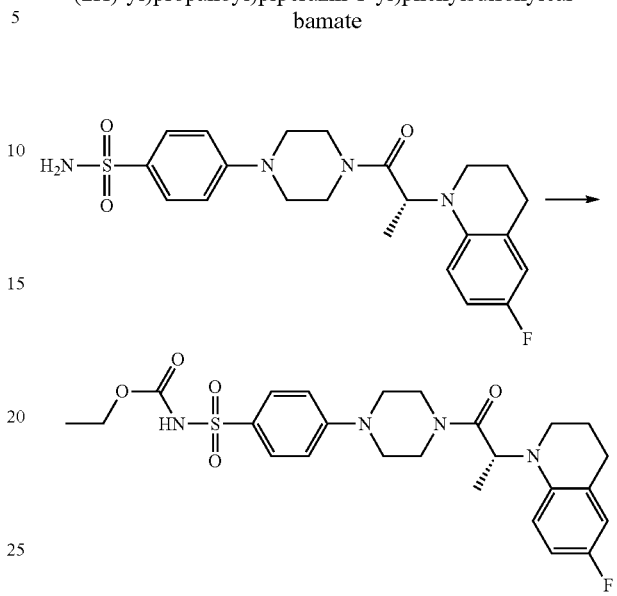

Synthesized according to General Procedure 1. LC/MS (10%-99% $CH_3CN$ (0.035% TFA)/$H_2O$ (0.05% TFA)), m/z: M+1 obs=519.3; $t_R$=2.93 min.

Example 3

(S)-methyl 4-(3-(6-chloro-3,4-dihydroquinolin-1 (2H)-yl)-2-oxopyrrolidin-1-yl)phenylsulfonylcarbamate Step 1: (S)-3-(6-chloro-3,4-dihydroquinolin-1(2H)-yl)dihydrofuran-2(3H)-one

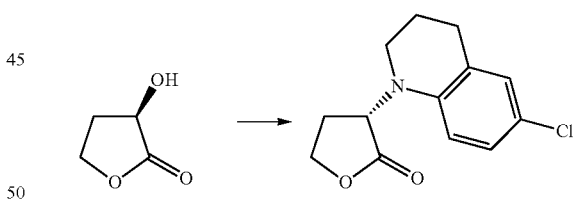

Under an $N_2$ atmosphere at −20° C., N,N-diisopropylethylamine (1.74 mL, 10 mmol) was added dropwise to a solution of (R)-(+)α-hydroxy-γ-butyrolactone (0.39 mL, 5 mmol) in dichloromethane (8 mL). Then trifluoromethanesulfonic anhydride (0.88 mL, 5.25 mmol) was added dropwise by maintaining internal temperature of the reaction mixture <−20° C. Upon completion of addition, the mixture was stirred at −20° C. for 1 hour. Then at −20° C., 6-Cl tetrahydroquinolin (1.26 g, 7.5 mmol) was added dropwise. The reaction was allowed to warm to RT over a period of 30 minutes and continued to stir at RT for 16 h. The reaction mixture was diluted with 200 mL of ethylacetate and washed with saturated sodium bicarbonate (3×). The organic layer was washed with a saturated aqueous NaCl solution (2×). The solution was dried over magnesium sulfate, filtered, and concentrated. Purification of the residue by silica gel chromatography using 10-30% ethyl acetate in hexane gave (S)-3-(6-chloro-3,4-dihydroquinolin-1(2H)-yl)dihydrofuran-2(3H)-one (1.14 g) as white solid. LC/MS (10%-99% CH$_3$CN (0.035% TFA)/H$_2$O (0.05% TFA)), m/z: M+1 obs=252.2; t$_R$=3.20 min.

Step 2: (S)-methyl 4-(2-(6-chloro-3,4-dihydroquinolin-1(2H)-yl)-4-hydroxybutanamido)phenylsulfonylcarbamate

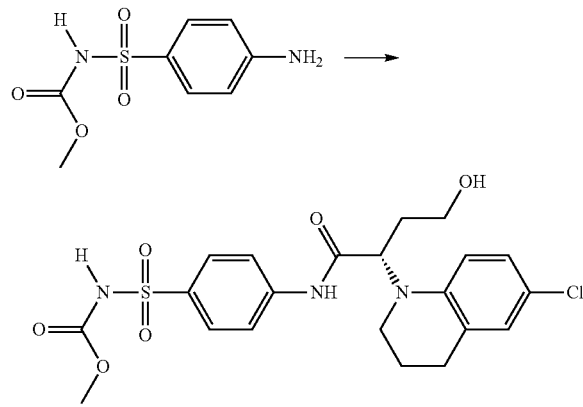

To a stirring suspension of the methyl 4-aminophenylsulfonylcarbamate (111 mg, 0.48 mmol) and CH$_2$Cl$_2$ (1 mL) under N$_2$, at 0° C., was added trimethylaluminum (0.24 mL, 0.48 mmol) dropwise over 20 minutes. The solution was stirred at ambient temperature for 30 minutes. The solution was cooled to 0° C. followed by the dropwise addition of (S)-3-(6-chloro-3,4-dihydroquinolin-1(2H)-yl)dihydrofuran-2(3H)-one (100 mg, 0.40 mmol) in CH$_2$Cl$_2$ (1.0 mL) over 30 minutes. The solution was stirred at ambient temperature for 19 h. The solution was cooled to 0° C. and quenched by slow addition of aqueous 1.0 M HCl. The organic portion was washed with 1.0 N aqueous HCl (2×1.0 mL) and evaporated to dryness under reduced pressure. The crude product of (R)-methyl 4-(2-(6-chloro-3,4-dihydroquinolin-1(2H)-yl)-4-hydroxybutanamido)phenylsulfonylcarbamate was used without purification in the next step.

Step 3: (S)-methyl 4-(3-(6-chloro-3,4-dihydroquinolin-1(2H)-yl)-2-oxopyrrolidin-1-yl)phenylsulfonylcarbamate

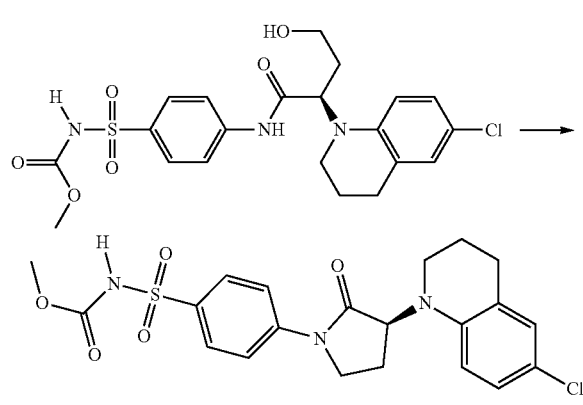

To a stirring solution of di-tert-butyl-azodicarboxylate (230 mg, 1.0 mmol) and THF (2.0 mL), under N$_2$, at 0° C. was added tributylphosphine (0.25 mL, 1.0 mmol), dropwise over 5 minutes. The colourless solution was stirred at 0° C. for 30 minutes. A solution of (R)-methyl 4-(2-(6-chloro-3,4-dihydroquinolin-1(2H)-yl)-4-hydroxybutanamido)phenyl sulfonyl carbamate (240 mg, 0.498 mmol) in THF (1 mL) was added dropwise over 5 minutes. The solution was stirred at ambient temperature for 2 h concentrated and purified by reverse phase HPLC using 10%-99% CH$_3$CN (0.035% TFA)/H$_2$O (0.05% TFA) to give the methyl 4-(3-(3,4-dichlorobenzyl)ureido)phenylsulfonylcarbamate. LC/MS (10%-99% CH$_3$CN (0.035% TFA)/H$_2$O (0.05% TFA)), m/z: M+1 obs=464.3; t$_R$=3.48 min.

Example 5 methyl 4-(3(3,4-dichlorobenzyl)ureido)phenylsulfonylcarbamate

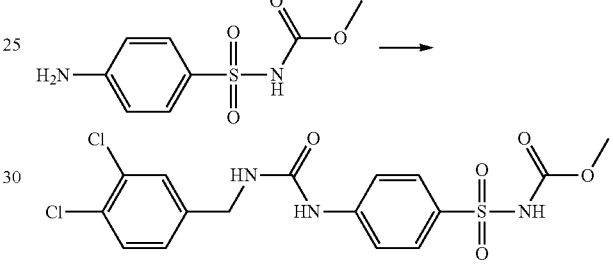

A solution of methyl 4-aminophenylsulfonylcarbamate (50 mg, 0.2 mmol), N,N-diisopropylethylamine (35 L, 0.2 mmol), 3,4-dichlorobenzylisocyanate (30 L, 0.2 mmol) in acetonitrile was stirred under an N$_2$ atmosphere for 19 h. The mixture was concentrated and the residue purified by reverse phase HPLC using 10%-99% CH$_3$CN (0.035% TFA)/H$_2$O (0.05% TFA) to give methyl 4-(3-(3,4-dichlorobenzyl)ureido)phenylsulfonylcarbamate. LC/MS (10%-99% CH$_3$CN (0.035% TFA)/H$_2$O (0.05% TFA)), m/z: M+1 obs=431.01; t$_R$=2.9 min.

General Procedure 2

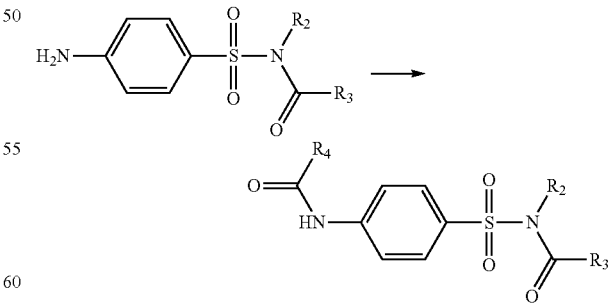

A solution of the sulfonamide (1 equivalent, 0.11 mmol) in CH$_2$Cl$_2$ (0.15-0.25M) was added to a solution of the appropriate carboxylic acid (1.0-3.0 equivalent, 0.12 mmol), DIEA (1.0-3.0 equivalent, 0.12 mmol) and HATU (1.0-3.0 equivalent, 0.12 mmol) in CH$_2$Cl$_2$ (0.15-0.25M). The mixture was stirred at RT for 19 h. The mixture was concentrated and the residue purified by reverse phase HPLC using 10%-99% CH₃CN (0.035% TFA)/H₂O (0.05% TFA).

Example 6

(R)-methyl 4-(2-4-fluoro-1H-indol-1-yl)propanamido) phenylsulfonylcarbamate

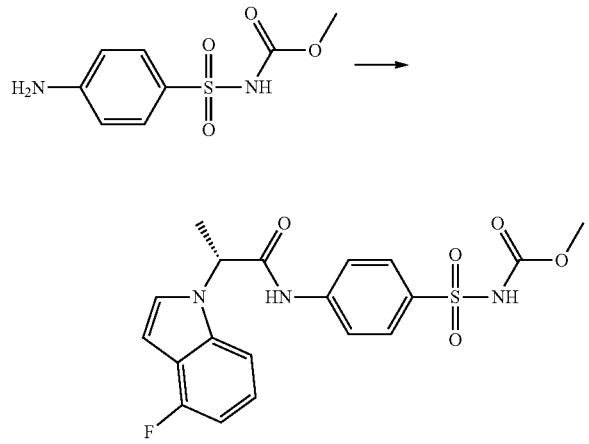

Prepared using General Procedure 2. ¹H NMR (400 MHz, DMSO-d6) δ 7.84 (q, J=9.3 Hz, 4H), 7.62 (d, J=3.4 Hz, 1H), 7.36 (d, J=8.3 Hz, 1H), 7.16-7.11 (m, 1H), 6.86-6.82 (m, 1H), 6.57 (d, J=3.2 Hz, 1H), 5.42 (q, J=7.1 Hz, 1H), 3.55 (s, 3H), 1.81 (d, J=7.1 Hz, 3H). LC/MS (10%-99% CH₃CN (0.035% TFA)/H₂O (0.05% TFA)), m/z: M+1 obs=420.1; $t_R$=3.15 min.

Example 7

(R)-methyl 4-(2-(6-chloro-3,4-dihydroquinolin-1 (2H)-yl)propanamido)phenylsulfonylcarbamate

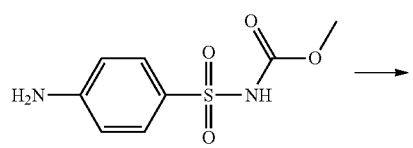

Prepared using General Procedure 2. LC/MS (10%-99% CH₃CN (0.035% TFA)/H₂O (0.05% TFA)), m/z: M+1 obs=452.3; $t_R$=3.34 min.

Example 8

(R)-methyl 4-(2-(6-(trifluoromethyl)-1H-indol-1-yl) propanamido)phenylsulfonylcarbamate Prepared using General Procedure 2. LC/MS (10%-99% CH₃CN (0.035% TFA)/H₂O (0.05% TFA)), m/z: M+1 obs=470.2; $t_R$=3.2 min.

Example 9

(R)-methyl 4-(2-(4-fluoro-1H-indol-1-yl)-4-methylpentanamido) phenylsulfonylcarbamate

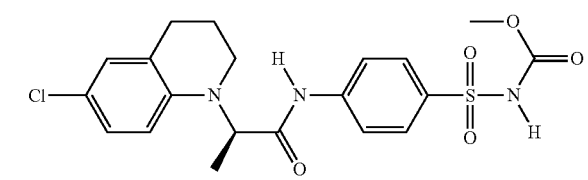

Prepared using General Procedure 2. LC/MS (10%-99% CH₃CN (0.035% TFA)/H₂O (0.05% TFA)), m/z: M+1 obs=462.2; $t_R$=3.65 min.

Example 10

(R)-methyl 4-(2,3-dichlorophenoxy)propanamido) phenylsulfonylcarbamate

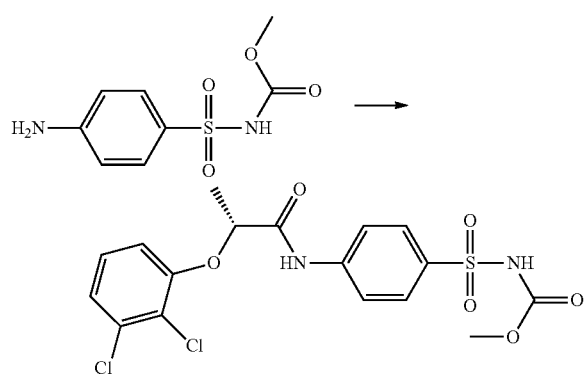

Prepared using General Procedure 2. LC/MS (10%-99% CH₃CN (0.035% TFA)/H₂O (0.05% TFA)), m/z: M+1 obs=447.2; $t_R$=3.36 min.

Step 1: (2R)-2-(4-Fluoroindol-1-yl)propionic acid

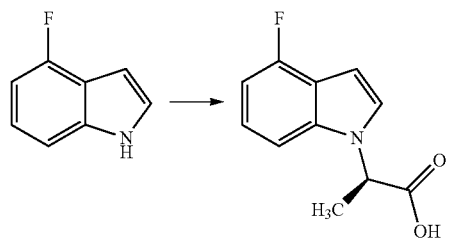

To a cooled (0-5° C.) solution of 4-fluoroindole (44.2 g, 327 mmol) in dry DMF (400 mL) was added sodium hydride (55-65% dispersion in mineral oil, 36 g, 817 mmol) in portions. The resulting suspension was stirred at 0-5° C. for 20 minutes. (2S)-(−)-2-Bromopropionic acid (31.8 mL, 343 mmol) was added dropwise. During the addition, the temperature was kept below 10° C. by cooling in an ice-bath. Upon completion of addition, the mixture was stirred at RT for 2 hours. The mixture was poured into water (1300 mL), and the aqueous solution was washed with heptanes (400 mL) and EtOAc (2×400 mL). The aqueous layer was acidified with concentrated aqueous HCl solution (85 mL, pH<1), and extracted with EtOAc (2×400 mL). The combined organic layers were washed with 1 N aq. HCl solution (2×300 mL) and with a saturated aqueous NaCl solution (300 mL). The solution was dried over sodium sulfate, filtered, and evaporated to dryness to afford a yellow oil (67.6 g). This oil (67.6 g, 323 mmol) was dissolved in 200 mL n-butyl acetate and (S)-L-(−)-α-methylbenzylamine (41.1 mL, 323 mmol) was added to the warm (50° C.) solution. The mixture was left to crystallize over several days. The formed solid was collected by filtration and washed with butyl acetate and heptanes (2×) (68.7 g). This material was recrystallized twice from 500 mL water/15% ethanol (1st recrystallization: 95% ee, 2nd recrystallization: 97.5% ee). This material was dissolved in EtOAc (300 mL) and washed with 1 N aqueous HCl (2×200 mL) and saturated aqueous NaCl solution (200 mL), dried over sodium sulfate, filtered, and evaporated to dryness giving (2R)-2-(4-fluoro-indol-1-yl)-propionic acid (18.7 g) as a greenish oil.

Example 11

(R)-Ethyl 4-(2-(4-fluoro-1H-indol-1-yl)propanamido)phenylsulfonyl-carbamate

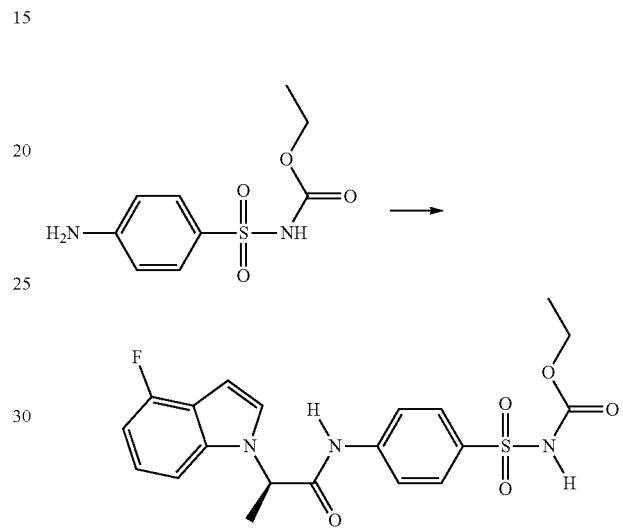

Prepared using General Procedure 2. LC/MS (10%-99% CH₃CN (0.035% TFA)/H₂O (0.05% TFA)), m/z: M+1 obs=434.2; $t_R$=3.13 min.

Example 12

(R)—N-(4-carbamoylsulfamoyl)phenyl-(2-(4-fluoro-1H indol-1-yl)propanamide

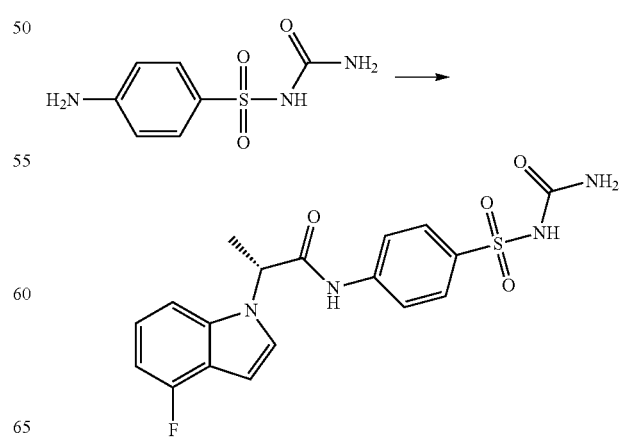

Prepared using General Procedure 2. LC/MS (10%-99% CH₃CN (0.035% TFA)/H₂O (0.05% TFA)), m/z: M+1 obs=405.5; $t_R$=2.65 min.

(R)-2-(4-Fluoro-1H-indol-1-yl)-N-(4-sulfamoylphenyl)propanamide

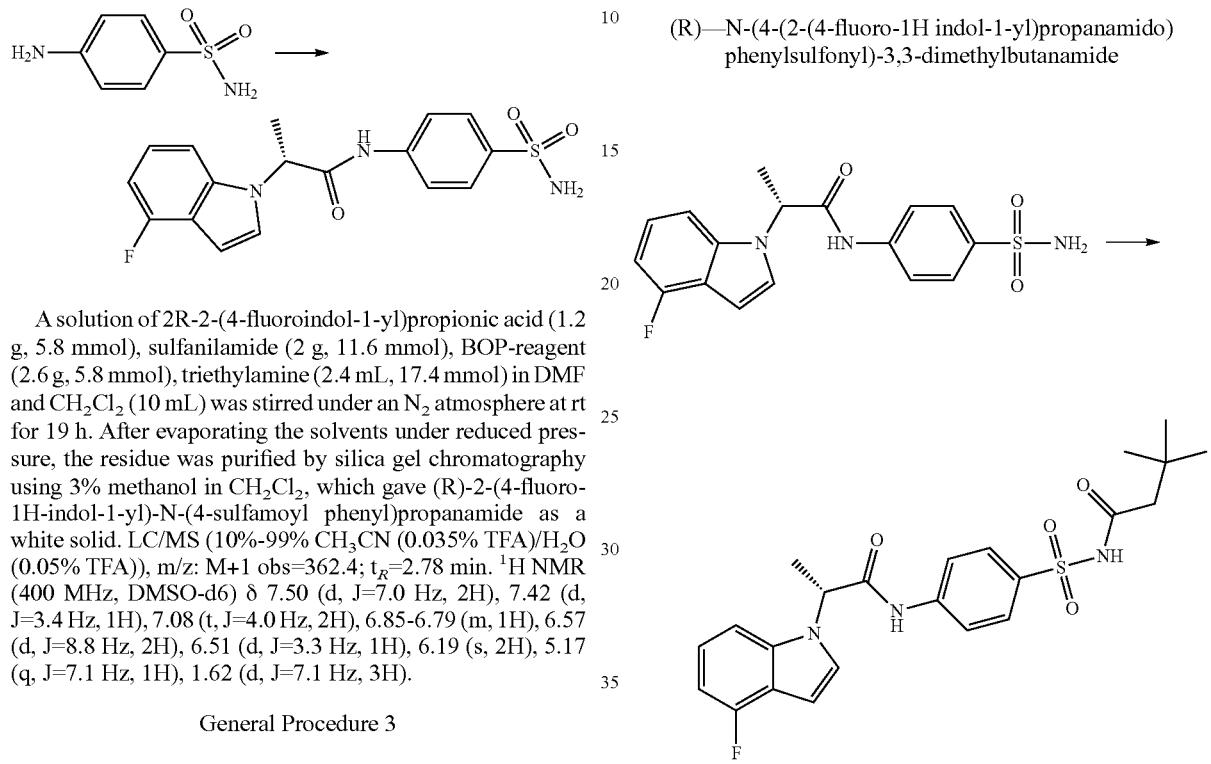

A solution of 2R-2-(4-fluoroindol-1-yl)propionic acid (1.2 g, 5.8 mmol), sulfanilamide (2 g, 11.6 mmol), BOP-reagent (2.6 g, 5.8 mmol), triethylamine (2.4 mL, 17.4 mmol) in DMF and CH₂Cl₂ (10 mL) was stirred under an N₂ atmosphere at rt for 19 h. After evaporating the solvents under reduced pressure, the residue was purified by silica gel chromatography using 3% methanol in CH₂Cl₂, which gave (R)-2-(4-fluoro-1H-indol-1-yl)-N-(4-sulfamoyl phenyl)propanamide as a white solid. LC/MS (10%-99% CH₃CN (0.035% TFA)/H₂O (0.05% TFA)), m/z: M+1 obs=362.4; $t_R$=2.78 min. ¹H NMR (400 MHz, DMSO-d6) δ 7.50 (d, J=7.0 Hz, 2H), 7.42 (d, J=3.4 Hz, 1H), 7.08 (t, J=4.0 Hz, 2H), 6.85-6.79 (m, 1H), 6.57 (d, J=8.8 Hz, 2H), 6.51 (d, J=3.3 Hz, 1H), 6.19 (s, 2H), 5.17 (q, J=7.1 Hz, 1H), 1.62 (d, J=7.1 Hz, 3H).

General Procedure 3

An appropriate acid chloride or isocyanate (1 equivalent, 0.08 mmol) was added to a stirring mixture of (R)-2-(4-fluoro-1H-indol-1-yl)-N-(4-sulfamoylphenyl)propanamide (1 equivalent, 0.08 mmol), potassium carbonate (3 equivalent, 0.24 mmol) and NMP (0.15-0.25M, 300 μL). The mixture was stirred until complete. The mixture was concentrated and the residue purified by reverse phase HPLC using 10%-99% CH₃CN (0.035% TFA)/H₂O (0.05% TFA) to provide the desired product.

Example 13

(R)—N-(4-(2-(4-fluoro-1H indol-1-yl)propanamido)phenylsulfonyl)-3,3-dimethylbutanamide

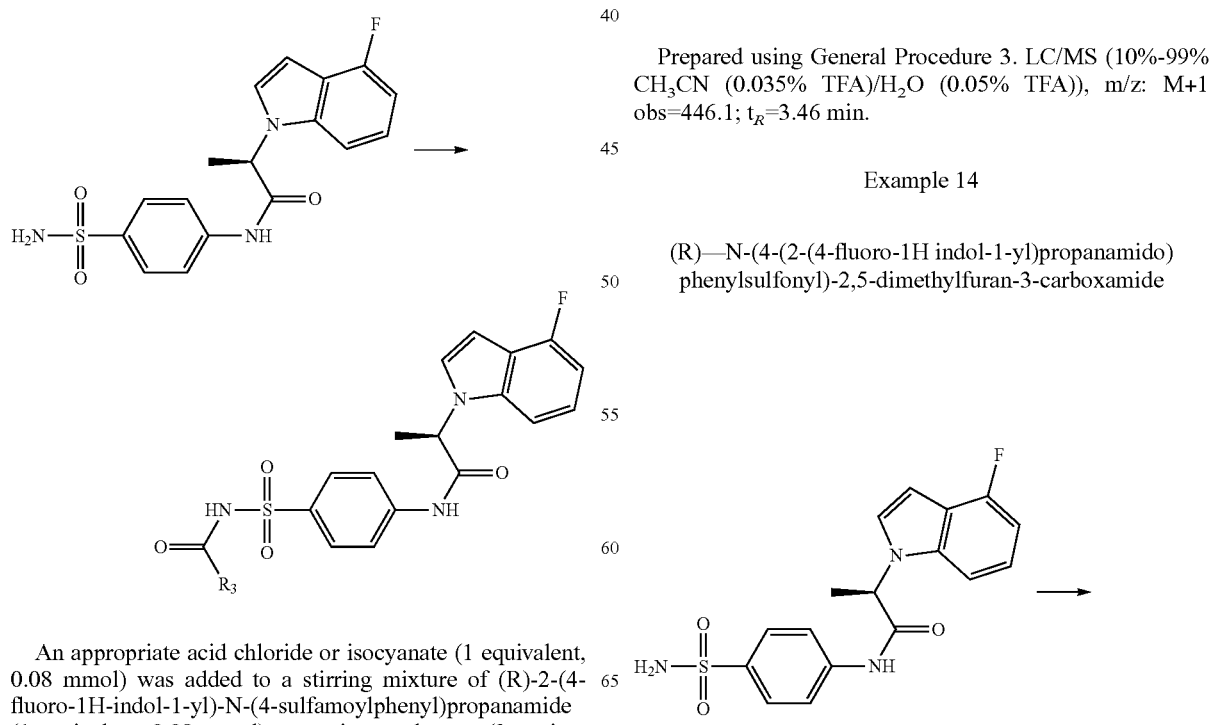

Prepared using General Procedure 3. LC/MS (10%-99% CH₃CN (0.035% TFA)/H₂O (0.05% TFA)), m/z: M+1 obs=446.1; $t_R$=3.46 min.

Example 14

(R)—N-(4-(2-(4-fluoro-1H indol-1-yl)propanamido)phenylsulfonyl)-2,5-dimethylfuran-3-carboxamide -continued

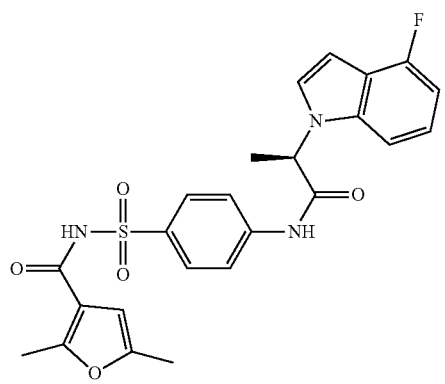

Prepared using General Procedure 3. LC/MS (10%-99% CH₃CN (0.035% TFA)/H₂O (0.05% TFA)), m/z: M+1 obs=484.1; t_R=3.58 min.

Example 15

(R)—N-(4-(2-(4-fluoro-1H indol-1-yl)propanamido)phenylsulfonyl)cyclopentanecarboxamide

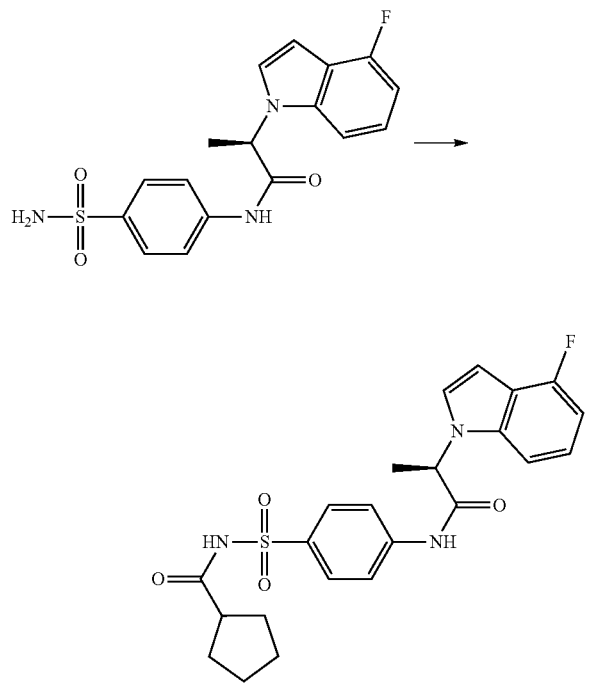 [SMILES: C[C@H](C(=O)Nc1ccc(S(N)(=O)=O)cc1)n1ccc2c(F)cccc21 ; C[C@H](C(=O)Nc1ccc(S(=O)(=O)NC(=O)C2CCCC2)cc1)n1ccc2c(F)cccc21]

Prepared using General Procedure 3. LC/MS (10%-99% CH₃CN (0.035% TFA)/H₂O (0.05% TFA)), m/z: M+1 obs=458.5; t_R=3.48 min.

Example 16

(R)-4-fluorophenyl-(4-(2-(4-fluoro-1H indol-1-yl)propanamido)phenylsulfonylcarbamate

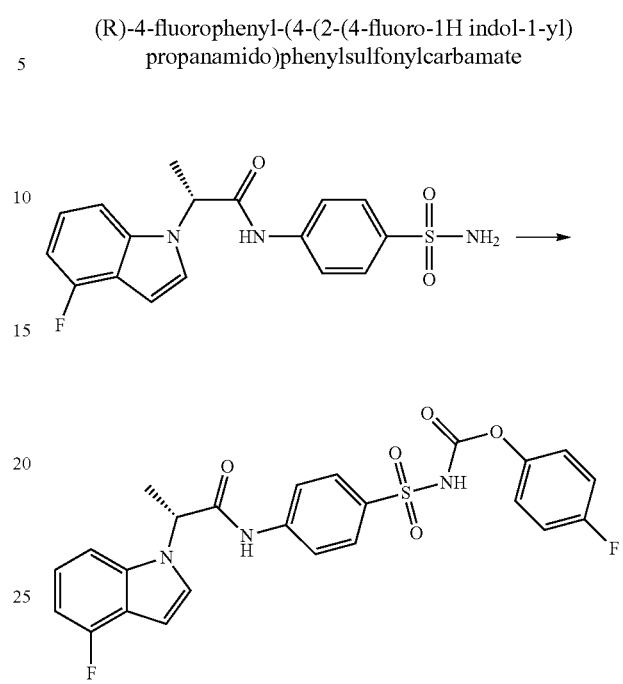

Prepared using General Procedure 3. LC/MS (10%-99% CH₃CN (0.035% TFA)/H₂O (0.05% TFA)), m/z: M+1 obs=500.3; t_R=4.48 min.

Example 17

(R)—N-(4-(2-(4-fluoro-1H indol-1-yl)propanamido)phenylsulfonyl)benzamide

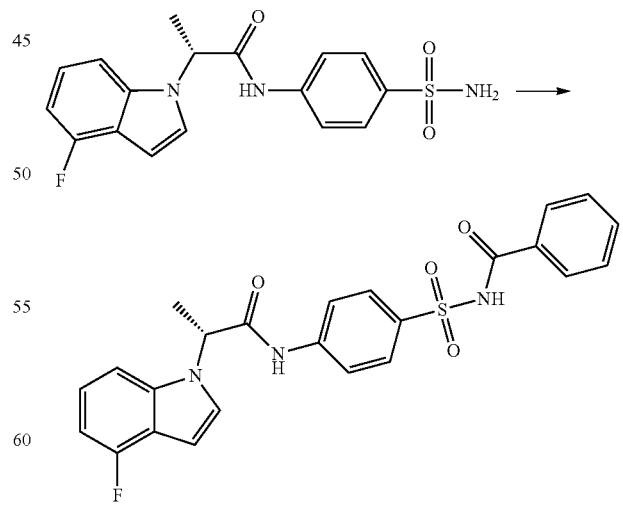

Prepared using General Procedure 3. LC/MS (10%-99% CH₃CN (0.035% TFA)/H₂O (0.05% TFA)), m/z: M+1 obs=466.3; t_R=3.43 min.

Example 18

(R)-2-(4-fluoro-1H indol-1-yl)-N-(4-(N-(methylcarbamoyl)sulfamoyl)phenyl)propanamide

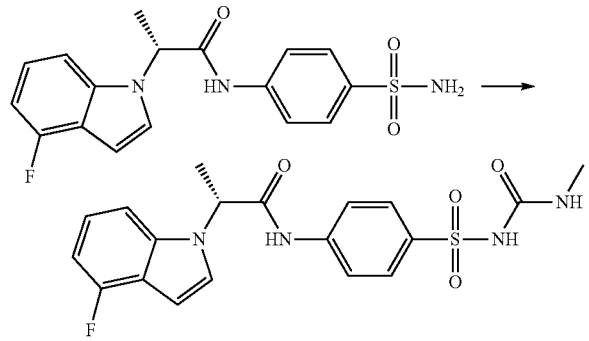

Prepared using General Procedure 3. LC/MS (10%-99% CH$_3$CN (0.035% TFA)/H$_2$O (0.05% TFA)), m/z: M+1 obs=419.3; t$_R$=2.92 min.

Example 19

(R)—N-(4-(N-(butylcarbamoyl)sulfamoyl)phenyl)-2-(4-fluoro-1H indol-1-yl)propanamide

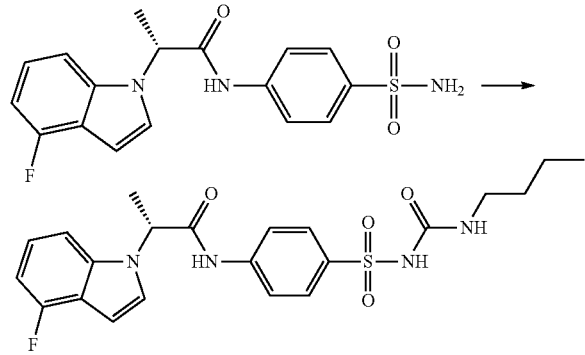

Prepared using General Procedure 3. LC/MS (10%-99% CH$_3$CN (0.035% TFA)/H$_2$O (0.05% TFA)), m/z: M+1 obs=461.3; t$_R$=3.38 min.

Example 20

(R)—N-(4-(N-(butylcarbamoyl)sulfamoyl)phenyl)-2-(4-fluoro-1H indol-1-yl)propanamide

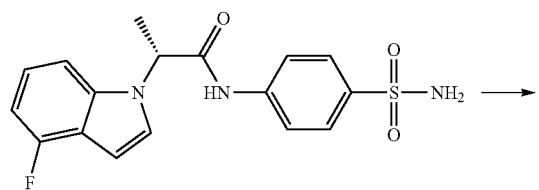

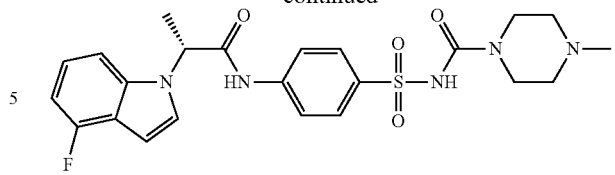

Prepared using General Procedure 3. LC/MS (10%-99% CH$_3$CN (0.035% TFA)/H$_2$O (0.05% TFA)), m/z: M+1 obs=488.1; t$_R$=2.48 min.

A person skilled in the chemical arts can use the examples and schemes along with known synthetic methodologies to synthesize compounds of the present invention, including the compounds in Table 3 below.

TABLE 3

Physical data for exemplary compounds.

| Compound No. | LC/MS M + 1 | LC/RT min |
|---|---|---|
| 1 | 436.3 | 3.06 |
| 2 | 390.2 | 2.69 |
| 3 | 417.3 | 2.91 |
| 4 | 421.1 | 2.7 |
| 5 | 494.5 | 2.2 |
| 6 | 452.3 | 3.34 |
| 7 | 418.3 | 2.97 |
| 8 | 424.3 | 3.13 |
| 9 | 335.1 | 2.48 |
| 10 | 480.3 | 2.04 |
| 11 | 458.5 | 3.48 |
| 12 | 402.3 | 3.17 |
| 13 | 460.5 | 3.53 |
| 14 | 402.3 | 3.14 |
| 15 | 392.1 | 3.09 |
| 16 | 436.2 | 3.33 |
| 17 | 420.1 | 2.96 |
| 18 | 410.3 | 3.16 |
| 19 | 413.3 | 2.94 |
| 20 | 436.2 | 3.33 |
| 21 | 430.5 | 3.21 |
| 22 | 466 | 3.64 |
| 23 | 462.2 | 3.65 |
| 24 | 480.3 | 3.83 |
| 25 | 470.2 | 3.19 |
| 26 | 422.3 | 3.23 |
| 27 | 406.3 | 3.07 |
| 28 | 422.1 | 2.9 |
| 29 | 500.3 | 4.48 |
| 30 | 431.01 | 2.9 |
| 31 | 419.3 | 2.92 |
| 32 | 490.3 | 1.72 |
| 33 | 436.3 | 3.31 |
| 34 | 420.1 | 3.06 |
| 35 | 427.2 | 3.39 |
| 36 | 420 | 2.96 |
| 37 | 461.3 | 3.2 |
| 38 | 419.3 | 2.86 |
| 39 | 456.3 | 3.29 |
| 40 | 402.5 | 2.9 |
| 41 | 519.3 | 2.93 |
| 42 | 444.4 | 3.18 |
| 43 | 434.2 | 3.13 |
| 44 | 413.3 | 2.95 |
| 45 | 215 | 0.6 |
| 46 | 400.3 | 3.16 |
| 47 | 418 | 3.31 |
| 48 | 393.3 | 2.68 |
| 49 | 560.3 | 3.4 |
| 50 | 521.3 | 2.95 |
| 51 | 436.1 | 3.05 |
| 52 | 535.3 | 3.05 |
| 53 | 464.3 | 3.48 |
| 54 | 461.3 | 3.41 |

TABLE 3-continued

Physical data for exemplary compounds.

| Compound No. | LC/MS M + 1 | LC/RT min |
|---|---|---|
| 55 | 436 | 3.34 |
| 56 | 349.3 | 2.55 |
| 57 | 488.1 | 2.48 |
| 58 | 447.2 | 3.36 |
| 59 | 420.2 | 3.2 |
| 60 | 484.5 | 2.68 |
| 61 | 505.3 | 2.8 |
| 62 | 452 | 3.43 |
| 63 | 405.5 | 2.65 |
| 64 | 433.3 | 3.09 |
| 65 | 447.2 | 3.35 |
| 66 | 484.5 | 3.58 |
| 67 | 436 | 3.35 |
| 68 | 420.2 | 2.99 |
| 69 | 406.3 | 3.08 |
| 70 | 422.3 | 2.98 |
| 71 | 482.3 | 2.98 |
| 72 | 446.3 | 3.46 |
| 73 | 468.2 | 3.11 |
| 74 | 466.3 | 3.43 |
| 75 | 452.2 | 3.55 |
| 76 | 472.3 | 3.48 |
| 77 | 462.3 | 3.71 |
| 78 | 427.2 | 3.38 |
| 79 | 461.3 | 3 |
| 80 | 436.2 | 3.12 |
| 81 | 426.3 | 3.32 |
| 82 | 404.3 | 3.07 |
| 83 | 436.6 | 3.33 |
| 84 | 418 | 3.32 |
| 85 | 434.2 | 3.08 |
| 86 | 494.4 | 4.01 |
| 87 | 470.2 | 3.2 |
| 88 | 365.1 | 2.54 |

VI. Assays for Detecting and Measuring Inhibition

A. Assays for Detecting and Measuring NaV Inhibition Properties of Compounds

1. Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" Drug Discov Today 4(9): 431-439).

2. VIPR® Optical Membrane Potential Assay Method with Chemical Stimulation

Cell Handling and Dye Loading 24 hours before the assay on VIPR, CHO cells endogenously expressing a NaV1.2 type voltage-gated are seeded in 96-well poly-lysine coated plates at 60,000 cells per well. Other subtypes are performed in an analogous mode in a cell line expressing the NaV of interest.

1.) On the day of the assay, medium is aspirated and cells are washed twice with 225 μL of Bath Solution #2 (BS#2).

2.) A 15 μM CC2-DMPE solution is prepared by mixing 5 mM coumarin stock solution with 10% Pluronic 127 1:1 and then dissolving the mix in the appropriate volume of BS#2.

3.) After bath solution is removed from the 96-well plates, the cells are loaded with 80 μL of the CC2-DMPE solution. Plates are incubated in the dark for 30 minutes at room temperature.

4.) While the cells are being stained with coumarin, a 15 μL oxonol solution in BS#2 is prepared. In addition to DiSBAC$_2$(3), this solution should contain 0.75 mM ABSC1 and 30 μL veratridine (prepared from 10 mM EtOH stock, Sigma #V-5754).

5.) After 30 minutes, CC2-DMPE is removed and the cells are washed twice with 225 μL of BS#2. As before, the residual volume should be 40 μL.

6.) Upon removing the bath, the cells are loaded with 80 μL of the DiSBAC$_2$(3) solution, after which test compound, dissolved in DMSO, is added to achieve the desired test concentration to each well from the drug addition plate and mixed thoroughly. The volume in the well should be roughly 121 μL. The cells are then incubated for 20-30 minutes.

7.) Once the incubation is complete, the cells are ready to be assayed on VIPR® with a sodium addback protocol. 120 μL of Bath solution #1 is added to stimulate the NaV dependent depolarization. 200 μL tetracaine was used as an antagonist positive control for block of the NaV channel.

3. Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\ nm} - \text{background}_{460\ nm})}{(\text{intensity}_{580\ nm} - \text{background}_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound

Solutions [mM]:

Bath Solution #1: NaCl 160, KCl 4.5, $CaCl_2$ 2, $MgCl_2$ 1, HEPES 10, pH 7.4 with NaOH Bath Solution #2 TMA-Cl 160, $CaCl_2$ 0.1, $MgCl_2$ 1, HEPES 10, pH 7.4 with KOH (final K concentration ~5 mM)

CC2-DMPE: prepared as a 5 mM stock solution in DMSO and stored at $-20°$ C.

$DiSBAC_2(3)$: prepared as a 12 mM stock in DMSO and stored at $-20°$ C.

ABSC1: prepared as a 200 mM stock in distilled $H_2O$ and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

4. VIPR® Optical Membrane Potential Assay Method with Electrical Stimulation

The following is an example of how NaV1.3 inhibition activity is measured using the optical membrane potential method #2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM $DiSBAC_2(3)$ (Aurora #00-100-010) in dry DMSO 10 mM CC2-DMPE (Aurora #00-100-008) in dry DMSO 200 mM ABSC1 in $H_2O$ Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×DISBAC2(3) with ABSC1=6 µM $DISBAC_2(3)$ and 1 mM ABSC1: The required amount of 10 mM $DISBAC_2(3)$ is added to a 50 ml conical tube and mixed with 1 µL 10% pluronic for each mL of solution to be made and vortexed together. Then HBSS/HEPES is added to make up 2× solution. Finally, the ABSC1 is added.

The 2×$DiSBAC_2(3)$ solution can be used to solvate compound plates. Note that compound plates are made at 2× drug concentration. Wash stained plate again, leaving residual volume of 50 µL. Add 50 µL/well of the 2×$DiSBAC_2(3)$ w/ ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay buffer #1

140 mM NaCl, 4.5 mM KCl, 2 mM $CaCl_2$, 1 mM $MgCl_2$, 10 mM HEPES, 10 mM glucose, pH 7.40, 330 mOsm Pluronic stock (1000×): 100 mg/mL pluronic 127 in dry DMSO Oxonol stock (3333×): 10 mM $DiSBAC_2(3)$ in dry DMSO Coumarin stock (1000×): 10 mM CC2-DMPE in dry DMSO ABSC1 stock (400×): 200 mM ABSC1 in water Assay Protocol Insert or use electrodes into each well to be assayed.

Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(\text{intensity}_{460\,nm} - \text{background}_{460\,nm})}{(\text{intensity}_{580\,nm} - \text{background}_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

B. Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

1. VOLTAGE-CLAMP Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs-F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), $CdCl_2$ (0.4), $NiCl_2$ (0.1), TTX ($0.25 \times 10^{-3}$).

2. CURRENT-CLAMP Assay for NaV Channel Inhibition Activity of Compounds

Cells were current-clamped in whole-cell configuration with a Multiclamp 700A amplifier (Axon Inst). Borosilicate pipettes (4-5 MOhm) were filled with (in mM):150 K-gluconate, 10 NaCl, 0.1 EGTA, 10 HEPES, 2 $MgCl_2$, (buffered to pH 7.34 with KOH). Cells were bathed in (in mM): 140 NaCl, 3 KCl, 1 MgCl, 1 CaCl, and 10 HEPES). Pipette potential was zeroed before seal formation; liquid junction potentials were not corrected during acquisition. Recordings were made at room temperature.

Examples of activities of the ion channel modulators of formulae (I, Ia, Ib, Ic, and Id) on modulating NaV1.3 receptors are shown below in Table 4. The compound activity for the NaV1.3 receptors is illustrated with "+++" if activity was measured to be less than 2.0 μM, "++" if activity was measured to be 2.0 μM to 5.0 μM, and "+" if activity was measured to be greater than 5.0 μM. The percent activity for the NaV1.3 receptors is illustrated with "+++" if more than 100 percent, "++" if percent activity was measured to be 25 to 100 percent, and "+" if activity was measured to be less than 25 percent.

TABLE 4

Activities of the ion channel modulators of formulae (I, Ia, Ib, Ic, and Id).

| Compound No. | Activity | Percent Activity |
|---|---|---|
| 1 | + | ++ |
| 2 | + | + |
| 3 | + | + |
| 4 | + | ++ |

TABLE 4-continued

Activities of the ion channel modulators of formulae (I, Ia, Ib, Ic, and Id).

| Compound No. | Activity | Percent Activity |
|---|---|---|
| 5 | + | ++ |
| 6 | +++ | ++ |
| 7 | + | + |
| 8 | + | + |
| 9 | + | + |
| 10 | ++ | ++ |
| 11 | + | ++ |
| 12 | + | + |
| 13 | + | + |
| 14 | + | ++ |
| 15 | + | + |
| 16 | ++ | +++ |
| 17 | + | + |
| 18 | + | + |
| 19 | + | + |
| 20 | ++ | ++ |
| 21 | + | ++ |
| 22 | +++ | +++ |
| 23 | +++ | ++ |
| 24 | + | + |
| 25 | + | ++ |
| 26 | + | ++ |
| 27 | + | + |
| 28 | + | + |
| 29 | + | + |
| 30 | + | ++ |
| 31 | + | ++ |
| 32 | + | ++ |
| 33 | + | ++ |
| 34 | +++ | ++ |
| 35 | + | + |
| 36 | + | ++ |
| 37 | + | ++ |
| 38 | + | + |
| 39 | + | ++ |
| 40 | ++ | ++ |
| 41 | + | + |
| 42 | + | ++ |
| 43 | + | + |
| 44 | + | + |
| 45 | + | + |
| 46 | + | ++ |
| 47 | + | ++ |
| 48 | + | + |
| 49 | + | ++ |
| 50 | + | ++ |
| 51 | + | + |
| 52 | + | ++ |
| 53 | + | ++ |
| 54 | + | + |
| 55 | + | ++ |
| 56 | + | + |
| 57 | + | + |
| 58 | + | ++ |
| 59 | +++ | ++ |
| 60 | + | + |
| 61 | + | + |
| 62 | + | ++ |
| 63 | ++ | ++ |
| 64 | + | + |
| 65 | + | + |
| 66 | + | + |
| 67 | + | ++ |
| 68 | + | ++ |
| 69 | + | ++ |
| 70 | + | ++ |
| 71 | + | + |
| 72 | + | + |
| 73 | + | ++ |
| 74 | + | ++ |
| 75 | + | ++ |
| 76 | + | + |
| 77 | + | ++ |
| 78 | + | ++ |
| 79 | + | + |

TABLE 4-continued

Activities of the ion channel modulators of formulae (I, Ia, Ib, Ic, and Id).

| Compound No. | Activity | Percent Activity |
|---|---|---|
| 80 | + | + |
| 81 | + | + |
| 82 | + | + |
| 83 | + | ++ |
| 84 | + | + |
| 85 | + | + |
| 86 | ++ | ++ |
| 87 | +++ | ++ |
| 88 | + | + |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of modulating a sodium ion channel comprising the step of contacting said sodium ion channel with a compound of formula I:

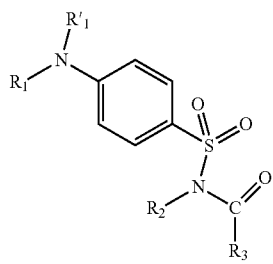

or a pharmaceutically acceptable salt thereof, wherein $R'_1$ and $R_1$ are independently $-Z^A R_4$, wherein each $Z^A$ is independently a bond or an optionally substituted branched or straight $C_{1-12}$ aliphatic chain wherein up to three carbon units of $Z^A$ are optionally and independently replaced by $-C(O)-$, $-C(S)-$, $-C(O)NR^A-$, $-C(O)NR^A NR^A-$, $-C(O)O-$, $-NR^A C(O)O-$, $-O-$, $-NR^A C(O)NR^A-$, $-NR^A NR^A-$, $-S-$, $-SO-$, $-SO_2-$, $-NR^A-$, $-SO_2 NR^A-$, or $-NR^A SO_2 NR^A-$;

$R_4$ is independently $R^A$, halo, $-OH$, $-CN$, $-NO_2$, $-NH_2$, or $-OCF_3$;

$R^A$ is independently hydrogen, an optionally substituted aryl, or an optionally substituted heteroaryl; or $R'_1$ and $R_1$ together with the nitrogen atom to which they are attached form a heterocycloaliphatic that is substituted with two of $-Z^B R_5$, wherein each $Z^B$ is independently a bond or an optionally substituted branched or straight $C_{1-6}$ aliphatic chain wherein up to three carbon units of $Z^B$ are optionally and independently replaced by $-C(O)-$, $-C(S)-$, $-C(O)NR^B-$, $-C(O)NR^B NR^B-$, $-C(O)O-$, $-NR^B C(O)O-$, $-O-$, $-NR^B C(O)NR^B-$, $-NR^B NR^B-$, $-S-$, $-SO-$, $-SO_2-$, $-NR^B-$, $-SO_2 NR^B-$, or $-NR^B SO_2 NR^B-$;

$R_5$ is independently $R^B$, halo, $-OH$, $-CN$, $-NO_2$, $-NH_2$, $=O$, or $-OCF_3$;

$R^B$ is independently hydrogen, an optionally substituted aryl, or an optionally substituted heteroaryl;

$R_2$ is $-Z^C R_6$, wherein each $Z^C$ is independently a bond or an optionally substituted branched or straight $C_{1-6}$ aliphatic chain wherein up to two carbon units of $Z^C$ are optionally and independently replaced by $-C(O)-$, $-C(S)-$, $-C(O)NR^C-$, $-C(O)NR^C NR^C-$, $-C(O)O-$, $-NR^C C(O)O-$, $-O-$, $-NR^C C(O)NR^C-$, $-NR^C NR^C-$, $-S-$, $-SO-$, $-SO_2-$, $-NR^C-$, $-SO_2 NR^C-$, or $-NR^C SO_2 NR^C-$;

$R_6$ is independently $R^C$, halo, $-OH$, $-CN$, $-NO_2$, $-NH_2$, or $-OCF_3$;

$R^C$ is independently hydrogen, optionally substituted cycloaliphatic, optionally substituted heterocycloaliphatic, optionally substituted aryl, or optionally substituted heteroaryl;

$R_3$ is $-Z^D R_7$, wherein each $Z^D$ is independently a bond or an optionally substituted branched or straight $C_{1-6}$ aliphatic chain wherein up to two carbon units of $Z^D$ are optionally and independently replaced by $-C(O)-$, $-C(S)-$, $-C(O)NR^D-$, $-C(O)NR^D NR^D-$, $-C(O)O-$, $-NR^D C(O)O-$, $-O-$, $-NR^D C(O)NR^D-$, $-NR^D NR^D-$, $-S-$, $-SO-$, $-SO_2-$, $-NR^D-$, $-SO_2 NR^D-$, or $-NR^D SO_2 NR^D-$;

$R_7$ is independently $R^D$, halo, $-OH$, $-CN$, $-NO_2$, $-NH_2$, or $-OCF_3$; and $R^D$ is independently hydrogen, optionally substituted cycloaliphatic, optionally substituted heterocycloaliphatic, optionally substituted aryl, or optionally substituted heteroaryl.

2. A method of treating in a subject acute, chronic, neuropathic, or inflammatory pain, visceral pain, osteoarthritis pain, radicular pain, back pain, head or neck pain, severe or intractable pain, nociceptive pain, breakthrough pain, post-surgical pain, or cancer pain, comprising administering an effective amount of a compound of formula I to said subject in need thereof

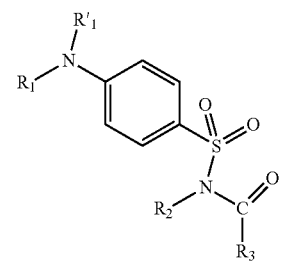

or a pharmaceutically acceptable salt thereof, wherein $R'_1$ and $R_1$ are independently $-Z^A R_4$, wherein each $Z^A$ is independently a bond or an optionally substituted branched or straight $C_{1-12}$ aliphatic chain wherein up to three carbon units of $Z^A$ are optionally and independently replaced by $-C(O)-$, $-C(S)-$, $-C(O)NR^A-$, $-C(O)NR^A NR^A-$, $-C(O)O-$, $-NR^A C(O)O-$, $-O-$, $-NR^A C(O)NR^A-$, $-NR^A NR^A-$, $-S-$, $-SO-$, $-SO_2-$, $-NR^A-$, $-SO_2 NR^A-$, or $-NR^A SO_2 NR^A-$;

$R_4$ is independently $R^A$, halo, —OH, —CN, —NO$_2$, —NH$_2$, or —OCF$_3$;

$R^A$ is independently hydrogen, an optionally substituted aryl, or an optionally substituted heteroaryl; or $R'_1$ and $R_1$ together with the nitrogen atom to which they are attached form a heterocycloaliphatic that is substituted with two of —$Z^B R_5$, wherein each $Z^B$ is independently a bond or an optionally substituted branched or straight $C_{1-6}$ aliphatic chain wherein up to three carbon units of $Z^B$ are optionally and independently replaced by —C(O)—, —C(S)—, —C(O)NR$^B$—, —C(O)NR$^B$NR$^B$—, —C(O)O—, —NR$^B$C(O)O—, —O—, —NR$^B$C(O)NR$^B$—, —NR$^B$NR$^B$—, —S—, —SO—, —SO$_2$—, —NR$^B$—, —SO$_2$NR$^B$—, or —NR$^B$SO$_2$NR$^B$—;

$R_5$ is independently $R^B$, halo, —OH, —CN, —NO$_2$, —NH$_2$, =O or —OCF$_3$;

$R^B$ is independently hydrogen, an optionally substituted aryl, or an optionally substituted heteroaryl;

$R_2$ is —$Z^C R_6$, wherein each $Z^C$ is independently a bond or an optionally substituted branched or straight $C_{1-6}$ aliphatic chain wherein up to two carbon units of $Z^C$ are optionally and independently replaced by —C(O)—, —C(S)—, —C(O)NR$^C$—, —C(O)NR$^C$NR$^C$—, —C(O)O—, —NR$^C$C(O)O—, —O—, —NR$^C$C(O)NR$^C$—, —NR$^C$NR$^C$—, —S—, —SO—, —SO$_2$—, —NR$^C$—, —SO$_2$NR$^C$—, or —NR$^C$SO$_2$NR$^C$—;

$R_6$ is independently $R^C$, halo, —OH, —CN, —NO$_2$, —NH$_2$, or —OCF$_3$;

$R^C$ is independently hydrogen, optionally substituted cycloaliphatic, optionally substituted heterocycloaliphatic, optionally substituted aryl, or optionally substituted heteroaryl;

$R_3$ is —$Z^D R_7$, wherein each $Z^D$ is independently a bond or an optionally substituted branched or straight $C_{1-6}$ aliphatic chain wherein up to two carbon units of $Z^D$ are optionally and independently replaced by —C(O)—, —C(S)—, —C(O)NR$^D$—, —C(O)NR$^D$NR$^D$—, —C(O)O—, —NR$^D$C(O)O—, —O—, —NR$^D$C(O)NR$^D$—, —NR$^D$NR$^D$—, —S—, —SO—, —SO$_2$—, —NR$^D$—, —SO$_2$NR$^D$—, or —NR$^D$SO$_2$NR$^D$—;

$R_7$ is independently $R^D$, halo, —OH, —CN, —NO$_2$, —NH$_2$, or —OCF$_3$; and $R^D$ is independently hydrogen, optionally substituted cycloaliphatic, optionally substituted heterocycloaliphatic, optionally substituted aryl, or optionally substituted heteroaryl.

3. The method of claim 2, wherein said method is used for treating acute, chronic, neuropathic, or inflammatory pain.

4. The method of claim 2, wherein said method is used for treating radicular pain, back pain, head pain, neck pain, intractable pain, acute pain, postsurgical pain, back pain, or cancer pain.

5. The method of claim 2, wherein said method is used for treating femur cancer pain; non-malignant chronic bone pain; neuropathic low back pain; myofascial pain syndrome; temporomandibular joint pain; chronic visceral pain, IBS pain; chronic and acute headache pain; chronic and acute neuropathic pain, chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; injury/exercise pain; acute visceral pain, abdominal pain; chest pain, cardiac pain; pelvic pain, renal colic pain, acute obstetric pain, labor pain; cesarean section pain; burn and trauma pain; acute intermittent pain, acute herpes zoster pain; breakthrough pain; orofacial pain, sinusitis pain, dental pain; multiple sclerosis (MS) pain; leprosy pain; Behcet's disease pain; phlebitic pain; Guillain-Barre pain; erythromelalgia pain; Fabry's disease pain; painful bladder syndrome; complex regional pain syndrome (CRPS), or angina-induced pain.

6. The method of claim 2, wherein $R'_1$ and $R_1$ are independently

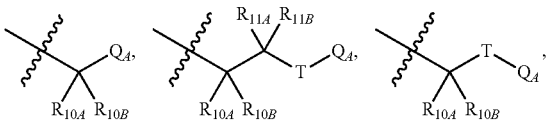

or —$Q_A$, wherein $R_{10A}$ and $R_{10B}$ are independently hydrogen, unsubstituted straight or branched $C_{1-3}$ aliphatic, or $R_{10A}$ and $R_{10B}$ together form an oxo group; $R_{11A}$ and $R_{11B}$ are independently hydrogen, optionally substituted straight or branched $C_{1-5}$ aliphatic, or $R_{11A}$ and $R_{11B}$ together with the carbon atom to which they are attached form an unsubstituted 3-5 membered cycloaliphatic; T is independently a bond, —O—, —NR$_{10A}$—, or —CH$_2$—; and $Q_A$ is hydrogen or an aryl or heteroaryl, each of which is optionally substituted with 1-3 of halo, hydroxy, optionally substituted $C_{1-3}$ alkoxy, or optionally substituted $C_{1-3}$ aliphatic.

7. The method claim 6, wherein one of $R_{11A}$ and $R_{11B}$ is hydrogen and the remaining $R_{11A}$ or $R_{11B}$ is methyl, ethyl, propyl, isopropyl, butyl, isobutyl, or tertbutyl, each of which is optionally substituted with hydroxy.

8. The method of claim 6, wherein T is independently a bond, —O—, —NR$_{10A}$—, or —CH$_2$—, wherein —NR$_{10A}$— is —NH—.

9. The method of claim 6, wherein $Q_A$ is phenyl, a bicyclic aryl, an optionally substituted monocyclic heteroaryl, or an optionally substituted bicyclic heteroaryl, each of which is optionally substituted with 1-3 of halo, —OH, —CN, optionally substituted $C_{1-3}$ alkoxy, optionally substituted $C_{1-3}$ aliphatic, or combinations thereof.

10. The method of claim 6, wherein $Q_A$ is a phenyl that is substituted with 1-3 of halo, unsubstituted $C_{1-3}$ alkyl, or unsubstituted $C_{1-3}$ alkoxy.

11. The method of claim 6, wherein $Q_A$ is an optionally substituted 9-10 membered bicyclic aryl.

12. The method of claim 6, wherein $Q_A$ is naphthylene-yl or 2,3-dihydro-1H-indene-yl, either of which is unsubstituted.

13. The method of claim 6, wherein $Q_A$ is an optionally substituted 5-6 membered monocyclic heteroaryl.

14. The method of claim 6, wherein $Q_A$ is furan-yl, thiophene-yl, oxazole-yl, pyridine-yl, pyramidine-yl, pyrazine-yl, or 1,3,5-triazine-yl, each of which is optionally substituted with 1-3 of –3 of halo, —OH, —CN, optionally substituted $C_{1-3}$ alkoxy, optionally substituted $C_{1-3}$ aliphatic, or combinations thereof.

15. The method of claim 6, wherein $Q_A$ is an optionally substituted bicyclic heteroaryl.

16. The method of claim 6, wherein $Q_A$ is indolizine-yl, indole-yl, isoindole-yl, 3H-indole-yl, indoline-yl, 1,2,3,4-tetrahydroquinoline-yl, benzo[d][1,3]dioxole-yl, quinoline-yl, each of which is optionally substituted with 1-3 of halo, —OH, —CN, optionally substituted $C_{1-3}$ alkoxy, optionally substituted $C_{1-3}$ aliphatic, or combinations thereof.
17. The method of claim 5, wherein one of $R'_1$ and $R_1$ is hydrogen and the remaining $R'_1$ or $R_1$ is selected from:
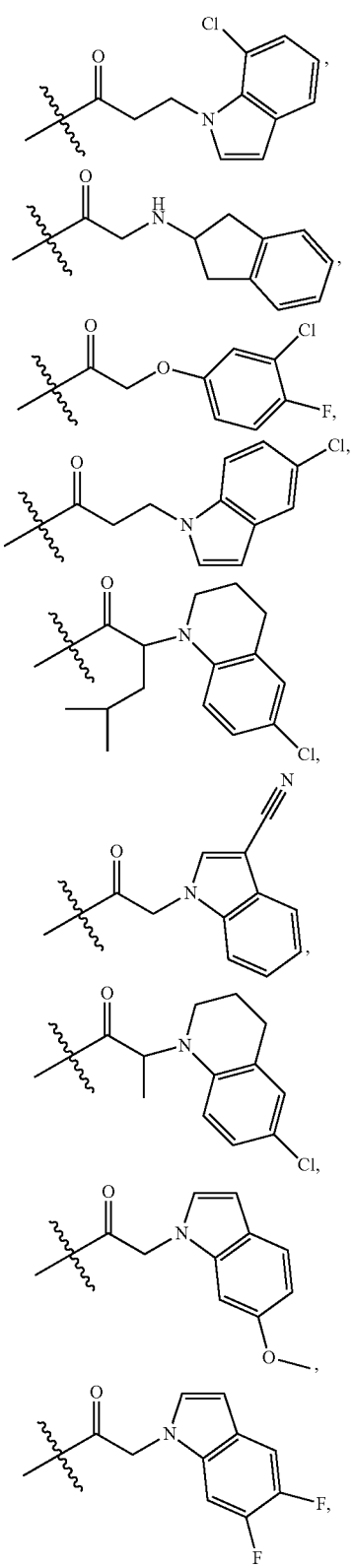
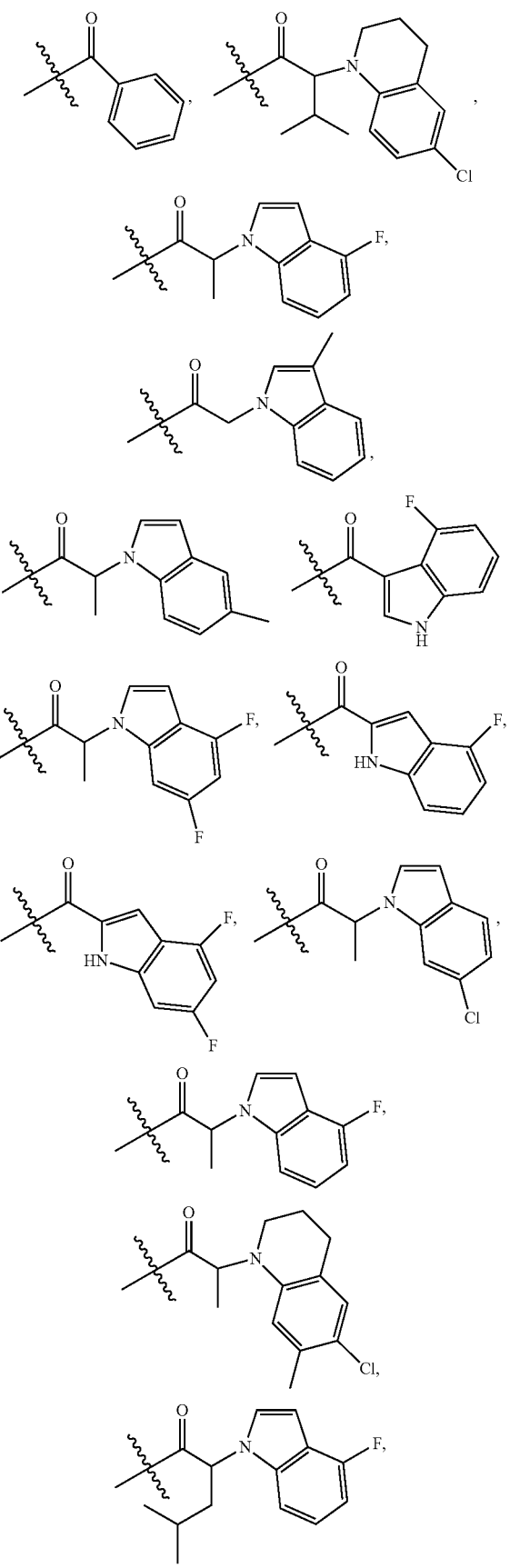

101
-continued
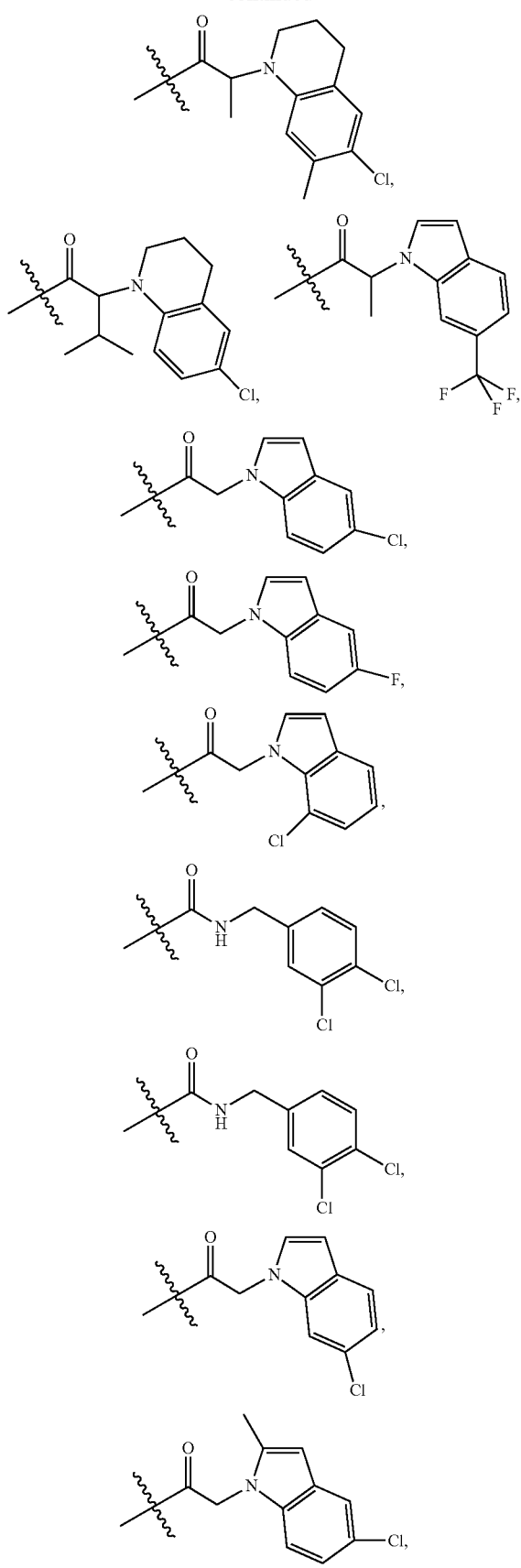
102
-continued
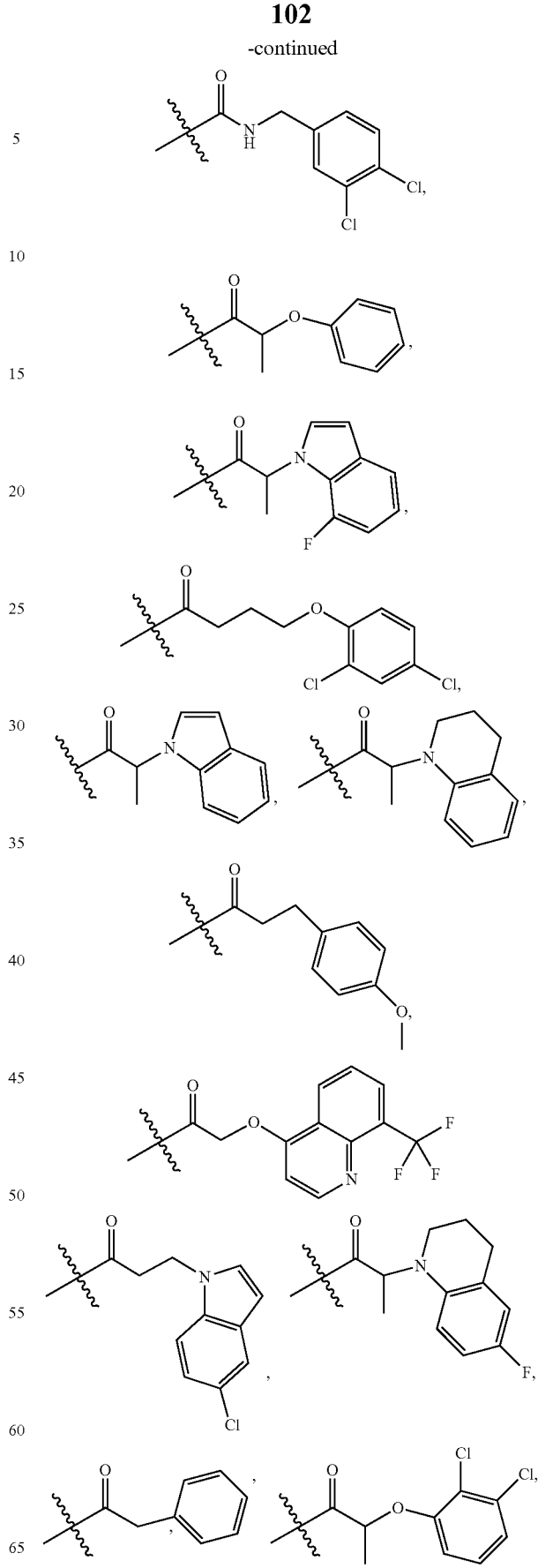

-continued

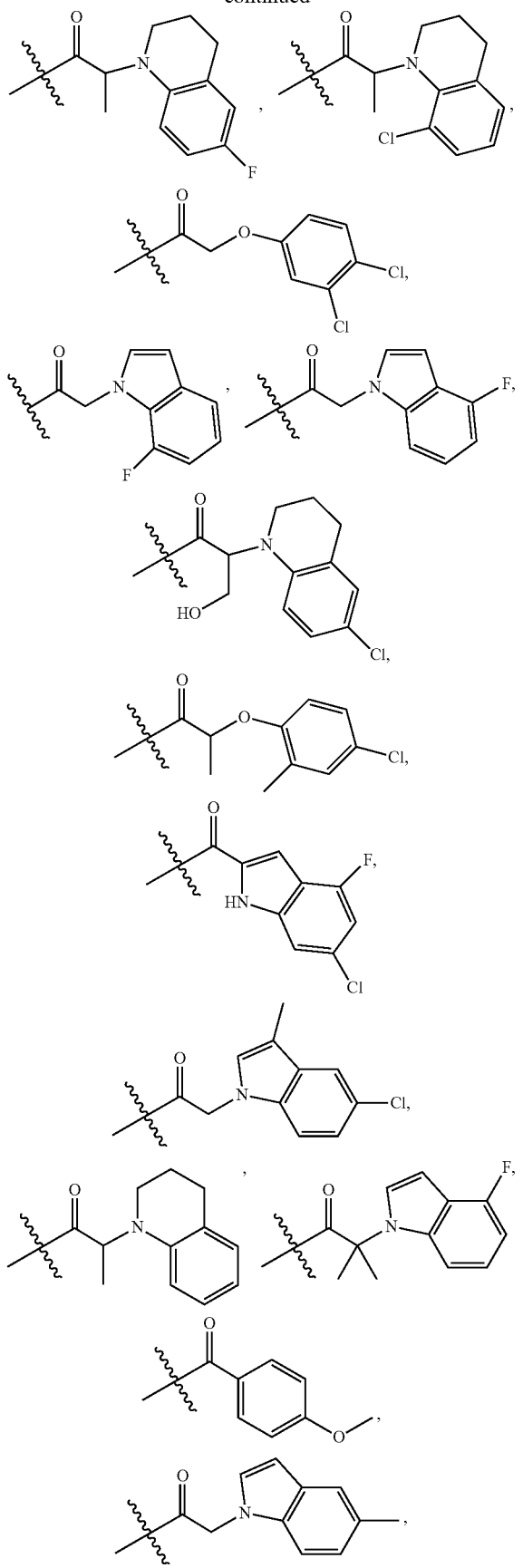

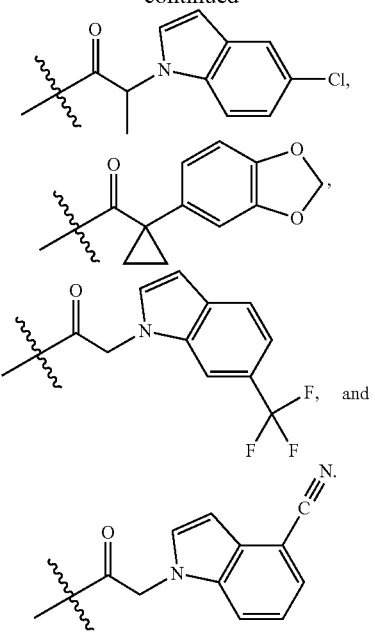

18. The method of claim 2, wherein R'₁ and R₁ together with the nitrogen atom to which they are attached form piperidine-yl, piperazine-yl, or pyrrolidone-yl, each of which is substituted with at least one acyl group, oxo group, heteroaryl group, or combinations thereof.

19. The method of claim 2, wherein, R'₁ and R₁ together with the nitrogen atom to which they are attached form a heterocycloaliphatic selected from:

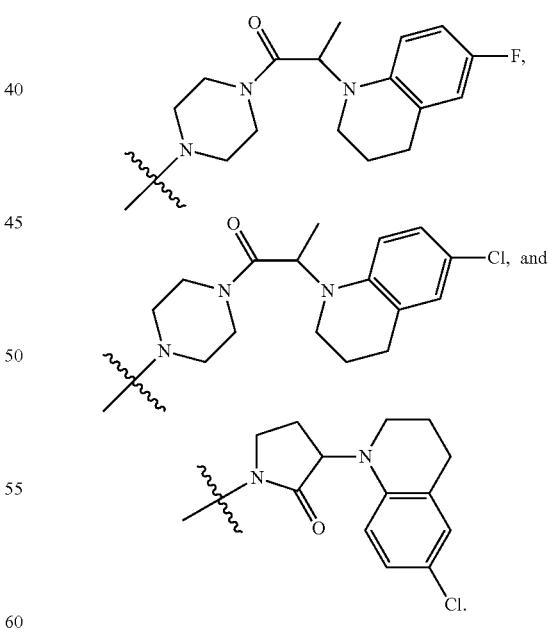

20. The method of claim 2, wherein $R_3$ is an optionally substituted $C_{1-5}$ alkoxy, $C_{1-5}$ alkynyl-oxy, branched or straight $C_{1-6}$ aliphatic, cycloaliphatic, or heterocycloaliphatic.

21. The method of claim 2, wherein $R_3$ is a piperidine-yl, piperazine-yl, pyrrolidine-yl, tetrahydrofuran-yl, tetrahydropyran-yl, thiomorpholine-yl, or imidazolidine-yl, each of which is optionally substituted with an unsubstituted $C_{1-3}$ aliphatic.

22. The method of claim 2, wherein $R_3$ is an optionally substituted aryl, aryloxy, heteroaryl, (aliphatic)amino, (cycloaliphatic)amino, (aryl)amino, or an amido group.

23. The method of claim 2, wherein $R_3$ is one selected from: —$CH_3$, —$NH_2$,

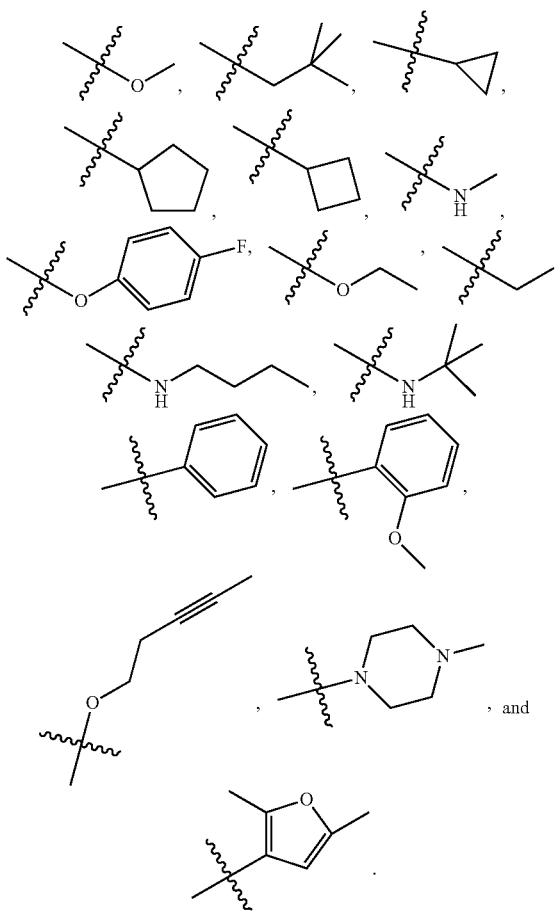

24. The method of claim 2 having formula Ia:

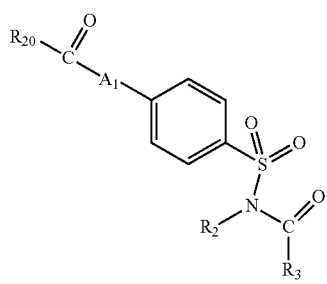

or a pharmaceutically acceptable salt thereof, wherein:

$A_1$ is —$NR_{21}$—, wherein $R_{21}$ is —$Z^E R_{22}$, wherein each $Z^E$ is independently a bond or an optionally substituted branched or straight $C_{1-6}$ aliphatic chain wherein up to three carbon units of $Z^E$ are optionally and independently replaced by —C(O)—, —C(O)$NR^E$—, —C(O)O—, —$NR^E$C(O)O—, —O—, or —$NR^E$—;

$R_{22}$ is independently $R^E$, halo, —OH, —CN, —$NO_2$, —$NH_2$, or —$OCF_3$;

$R^E$ is independently hydrogen, an optionally substituted aryl, or an optionally substituted heteroaryl.

$R_{20}$ is —$Z^F R_{30}$, wherein each $Z^F$ is independently a bond or an optionally substituted branched or straight $C_{1-6}$ aliphatic chain wherein up to three carbon units of $Z^F$ are optionally and independently replaced by —C(O)—, —C(O)$NR^F$—, —C(O)O—, —$NR^F$C(O)O—, —O—, or —$NR^F$—;

$R_{30}$ is independently $R^F$, halo, —OH, —CN, —$NO_2$, —$NH_2$, or —$OCF_3$; and $R^F$ is independently hydrogen, an optionally substituted aryl, or an optionally substituted heteroaryl.

25. The method of claim 2 having formula Ib:

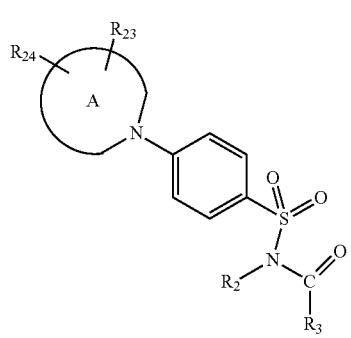

or a pharmaceutically acceptable salt thereof, wherein:

Ring A is a 5-6 membered heterocycloaliphatic ring having at least one nitrogen atom;

$R_{23}$ is independently —$Z^G R_{25}$, wherein each $Z^G$ is independently a bond or an optionally substituted branched or straight $C_{1-3}$ aliphatic chain wherein up to two carbon units of $Z^G$ are optionally and independently replaced by —C(O)—, —C(O)$NR^G$—, —C(O)O—, —$NR^G$C(O)O—, —O—, or —$NR^G$—;

$R_{25}$ is independently $R^G$, halo, —OH, —CN, —$NO_2$, —$NH_2$, or —$OCF_3$;

$R^G$ is independently hydrogen or an optionally substituted heteroaryl; and $R_{24}$ is hydrogen or an oxo group.

26. The method of claim 2 having formula Ic:

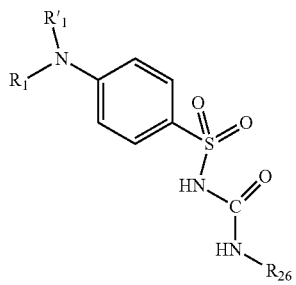

or a pharmaceutically acceptable salt thereof, wherein $R_{26}$ is hydrogen or straight or branched $C_{1-5}$ aliphatic.

27. The method of claim 2 having formula Id:
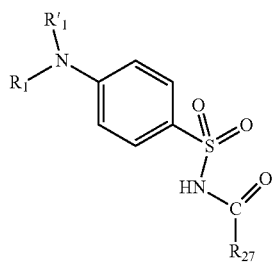
or a pharmaceutically acceptable salt thereof, wherein $R_{27}$ is an optionally substituted cycloaliphatic, heterocycloaliphatic, aryl, or heteraryl.
28. The method of claim 2, wherein the compound is selected from the following table:
| 1 |
|---|
| 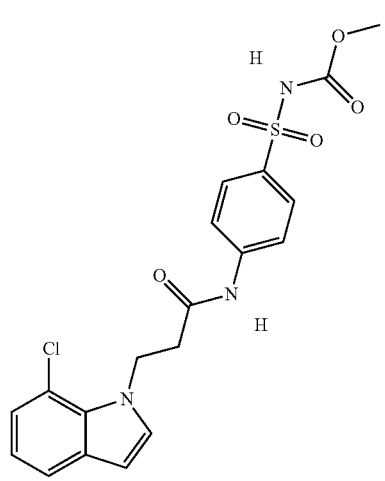 |
| 2 |
| 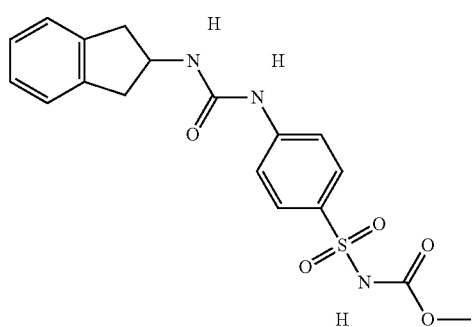 |
| 3 |
| 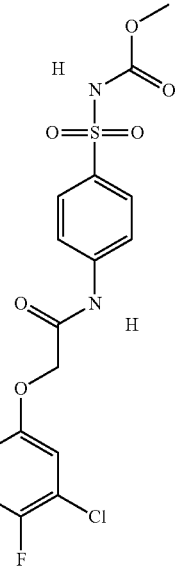 |
| 4 |
| 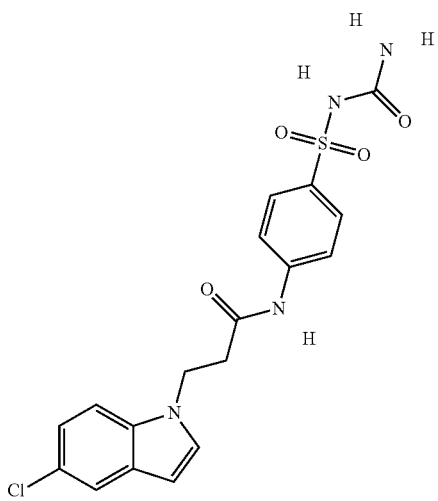 |
| 5 |
| 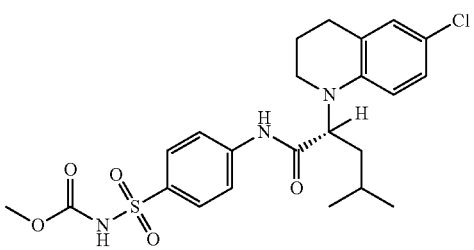 [SMILES: COC(=O)NS(=O)(=O)c1ccc(NC(=O)[C@H](CC(C)C)N2CCCc3cc(Cl)ccc32)cc1] |

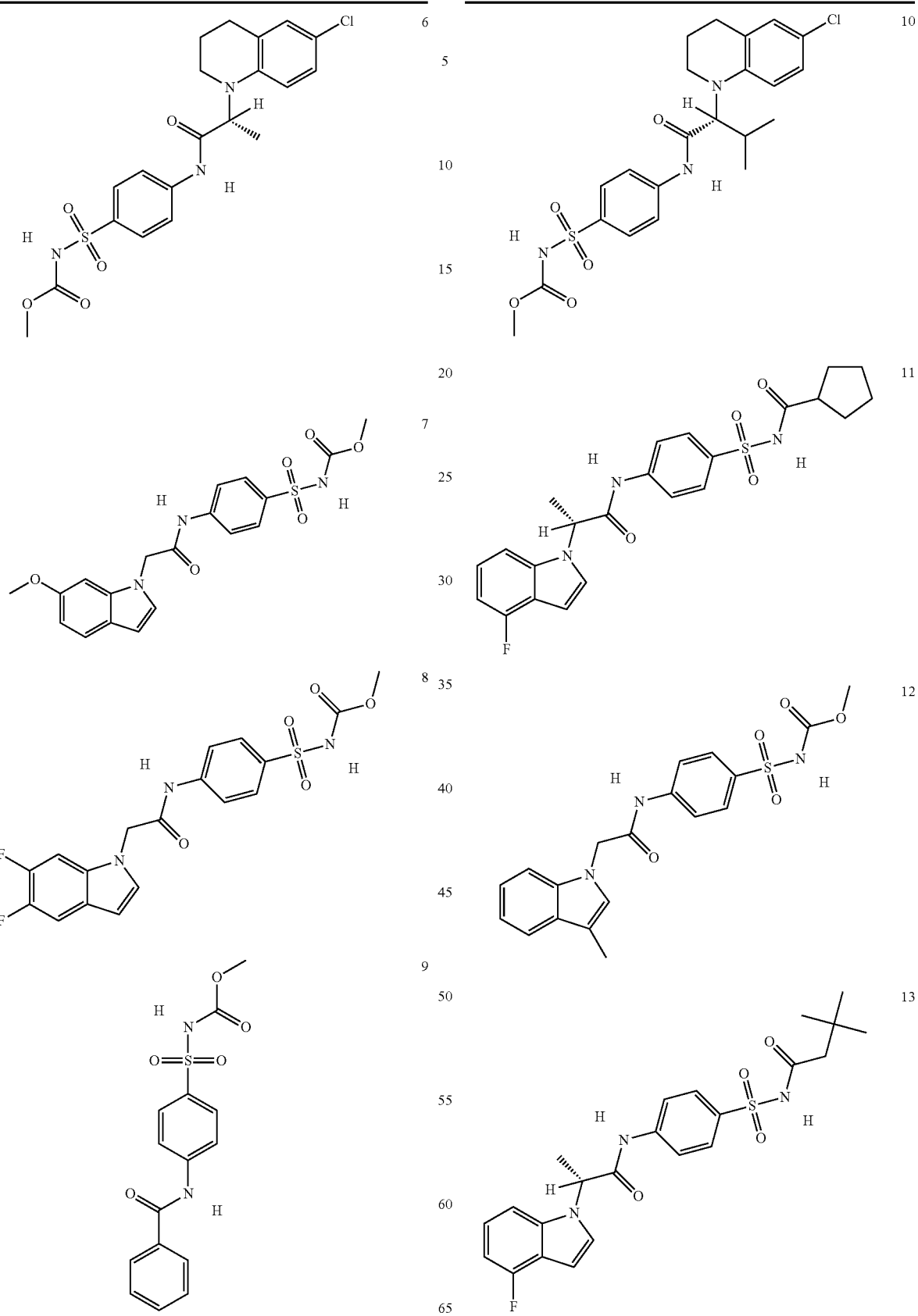

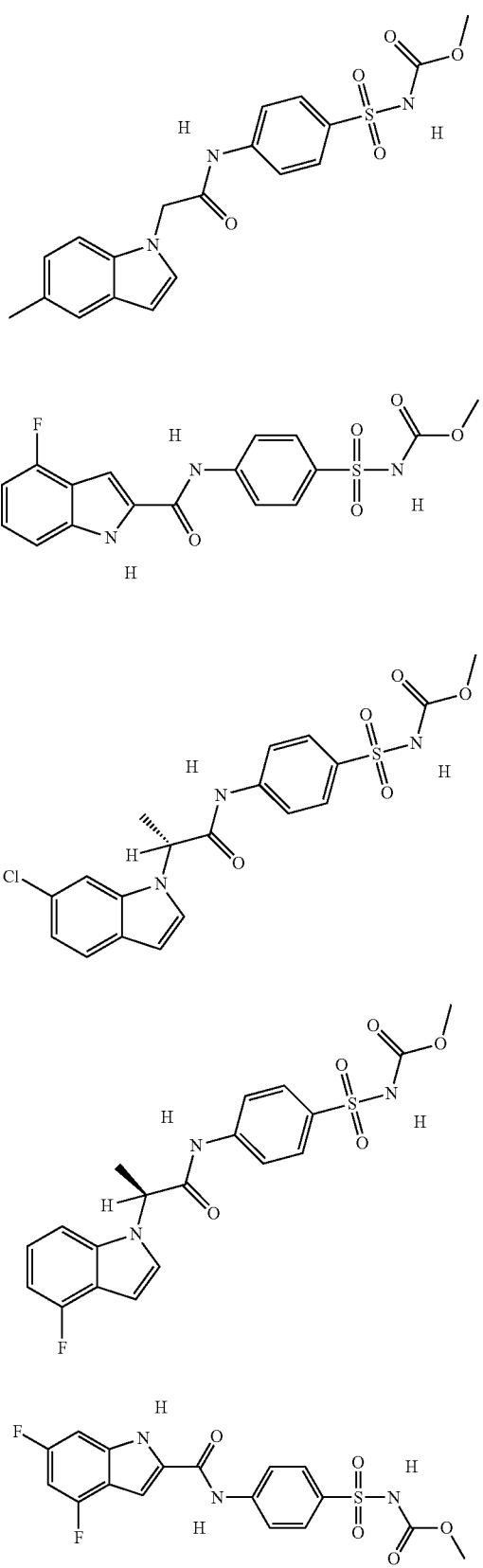
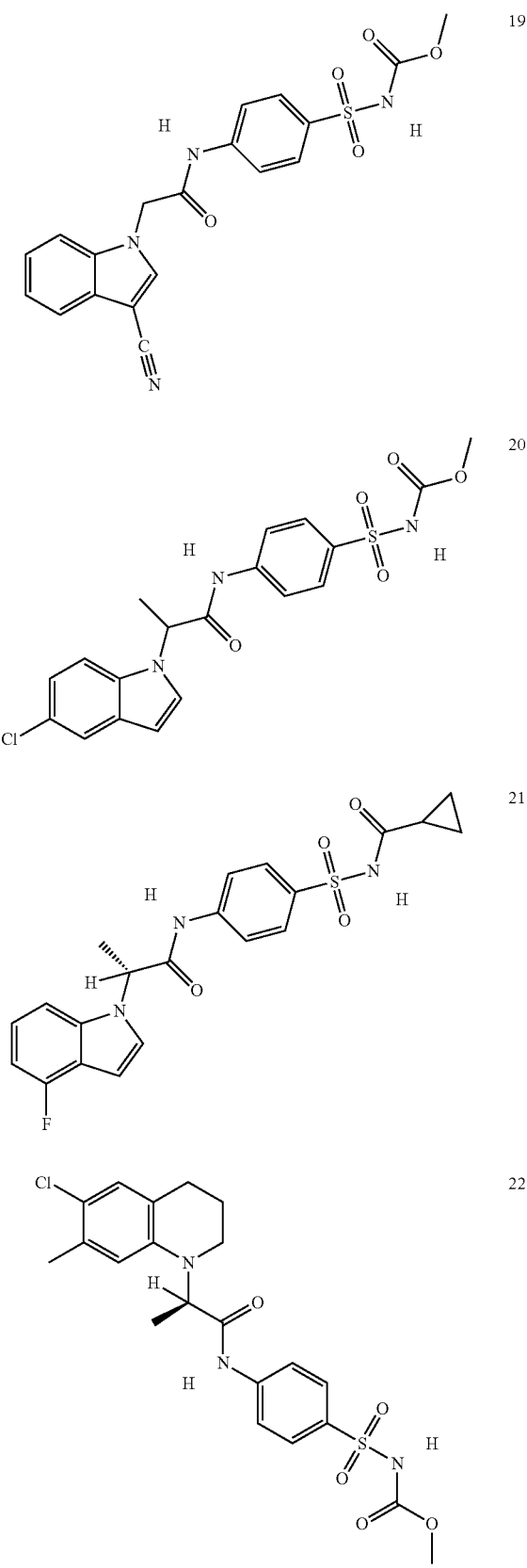

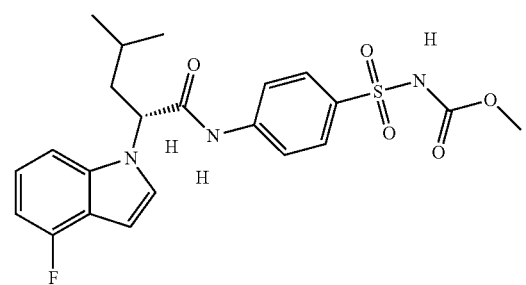
23
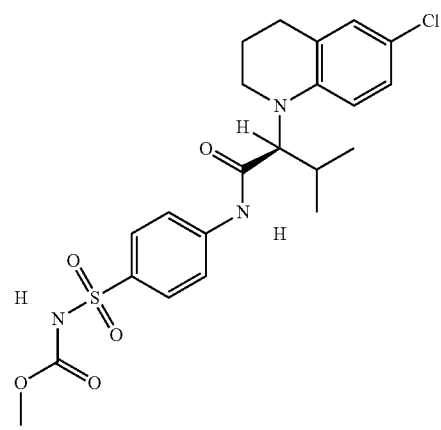
24
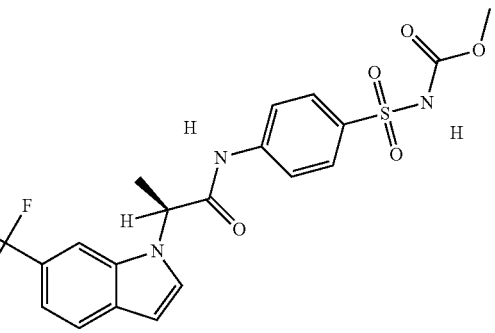
25
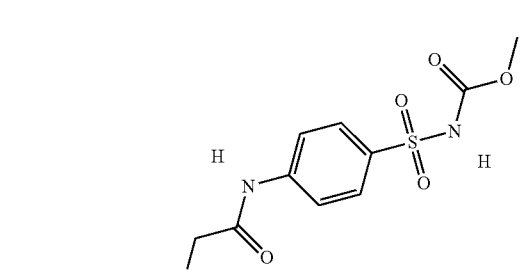
26
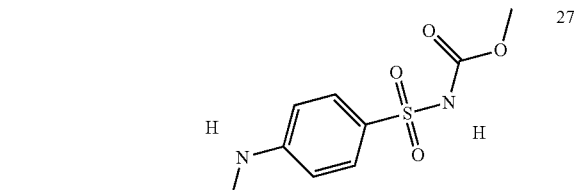
27
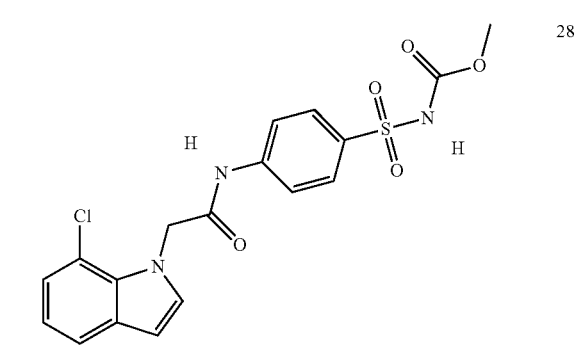
28
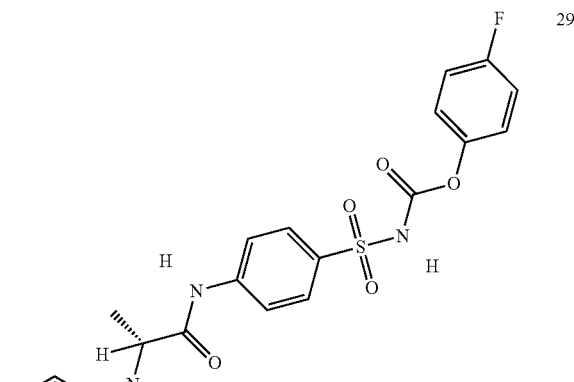
29

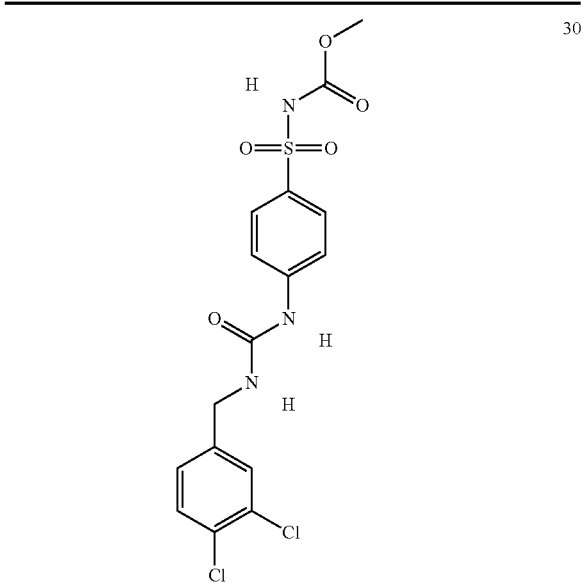
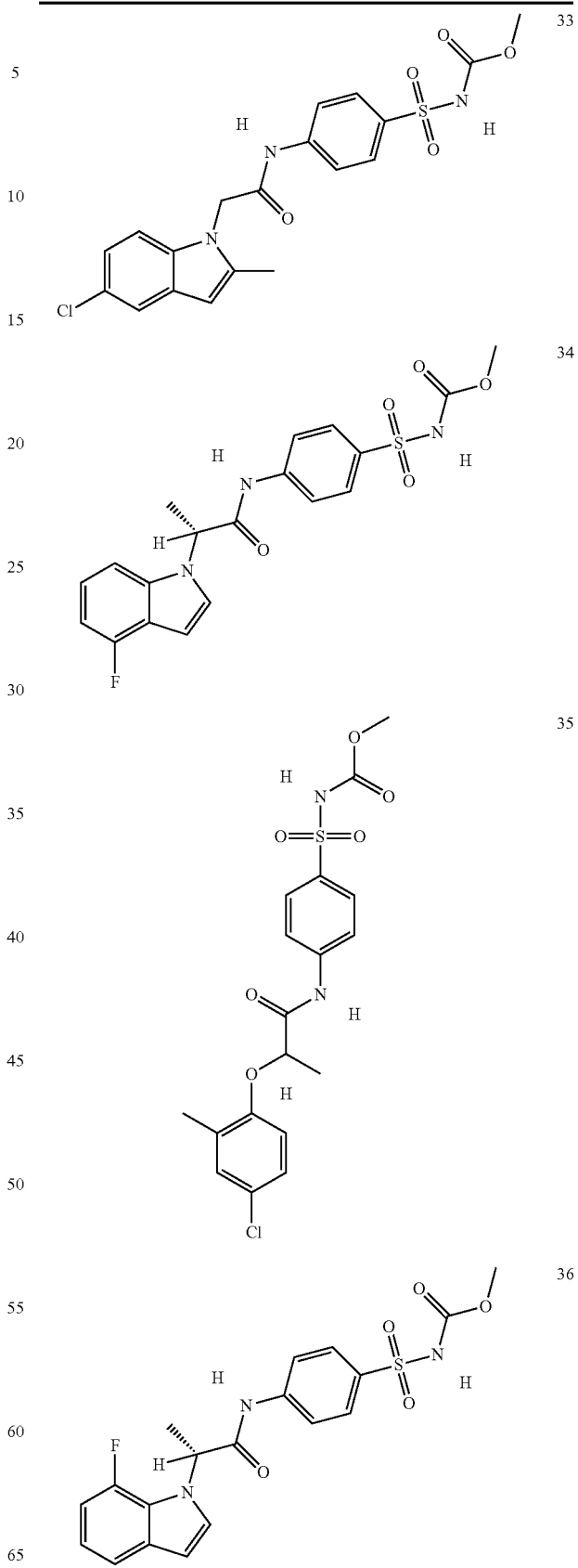

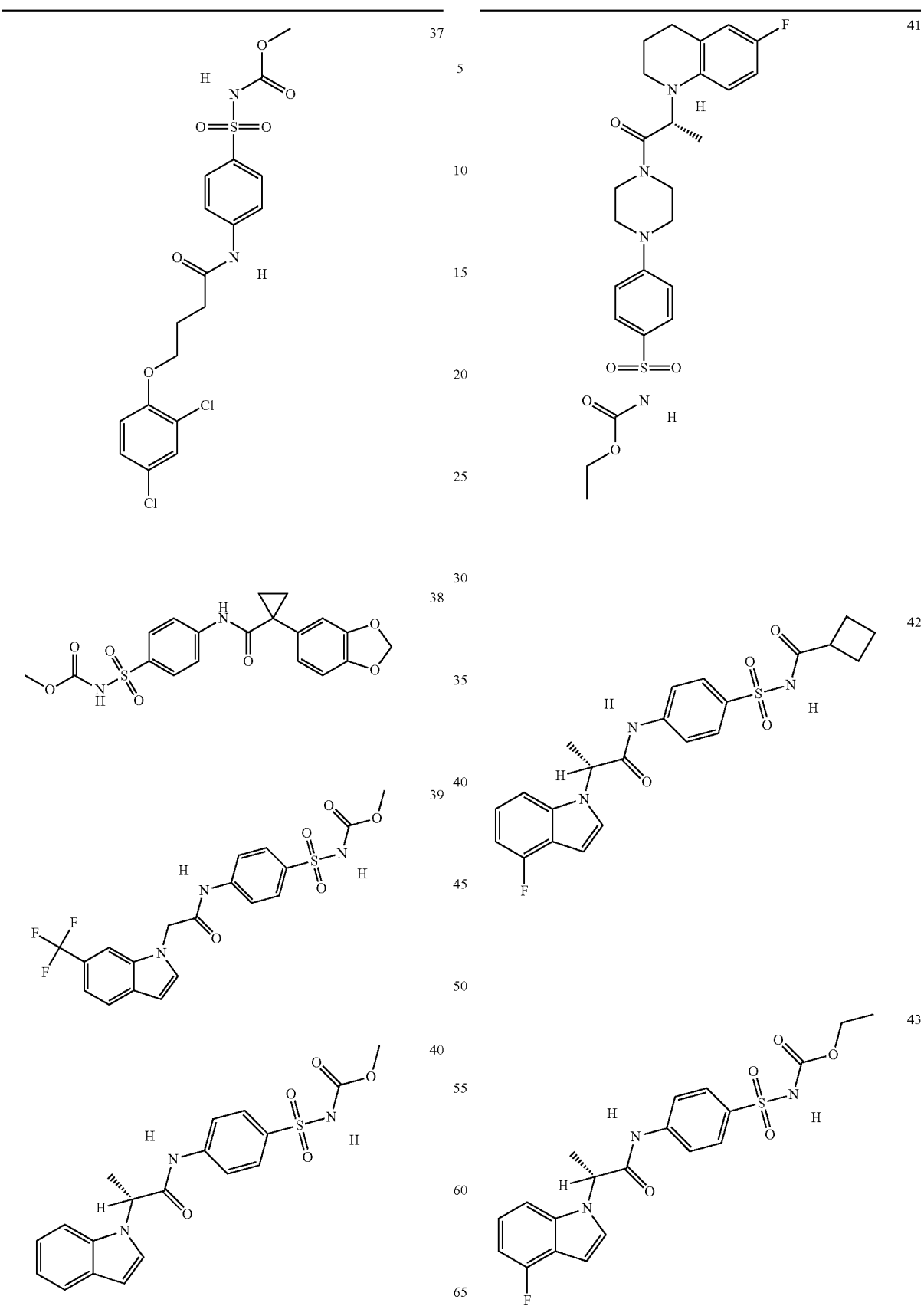

-continued
| | |
|---|---|
| 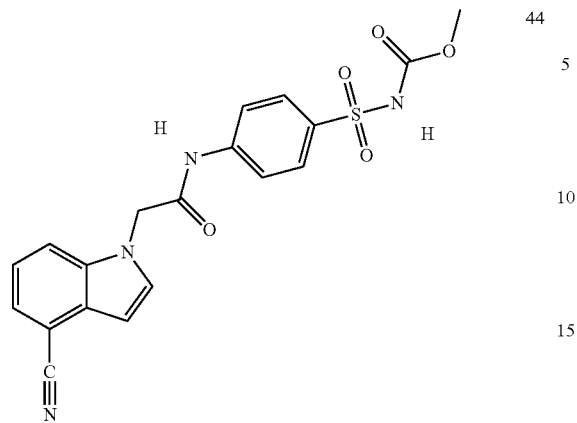 44 | 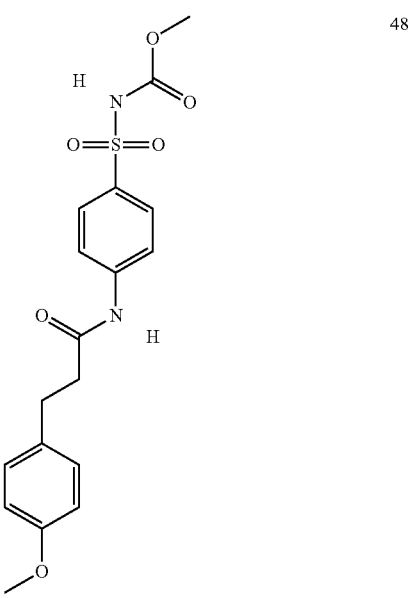 48 |
| 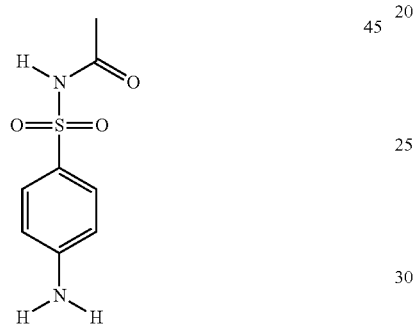 45 | |
| 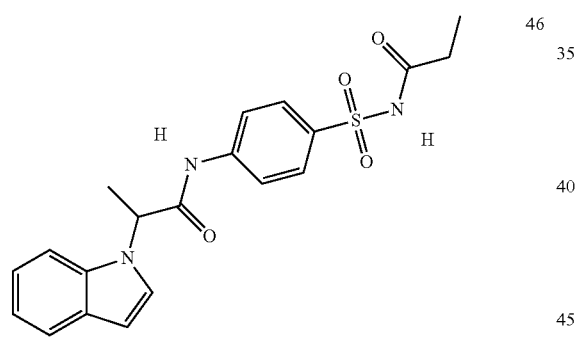 46 | 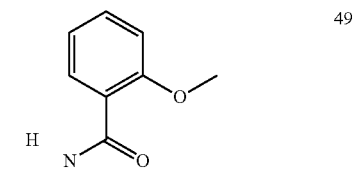 49 |
| 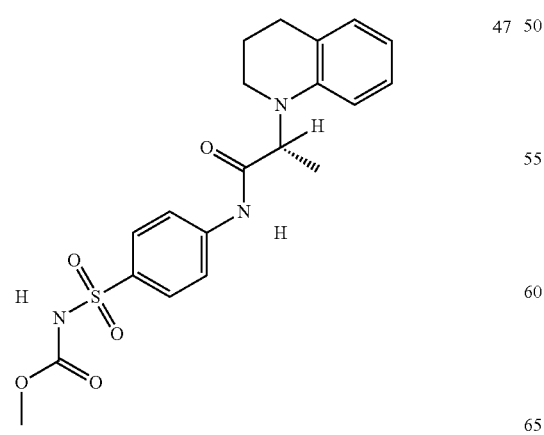 47 | 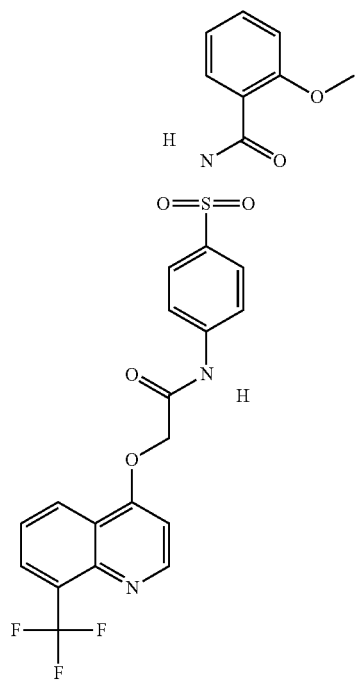 |

| 121 -continued | 122 -continued |
|---|---|
| 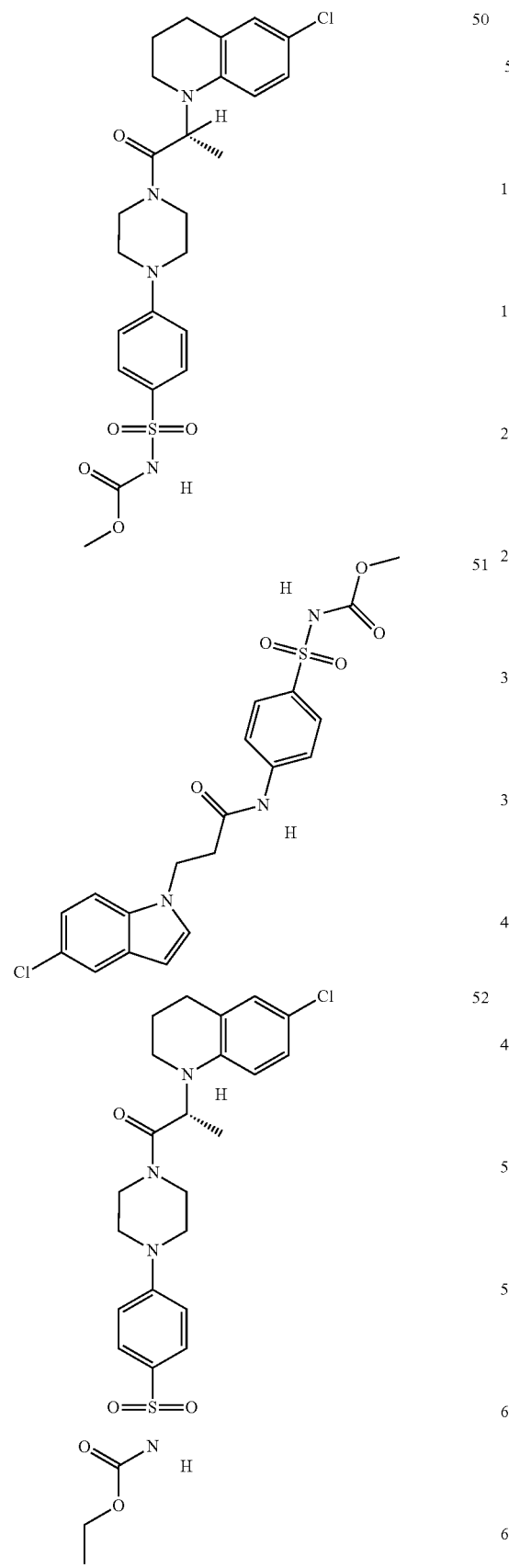 | 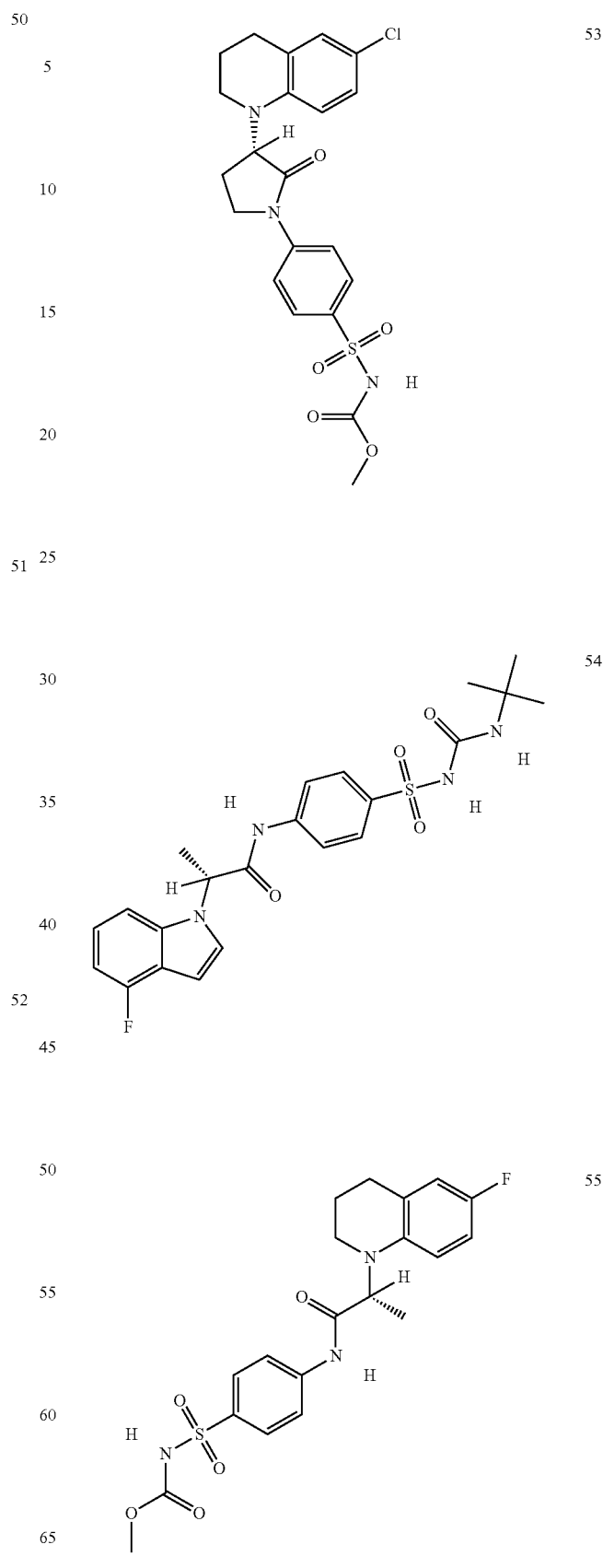 |

-continued
56
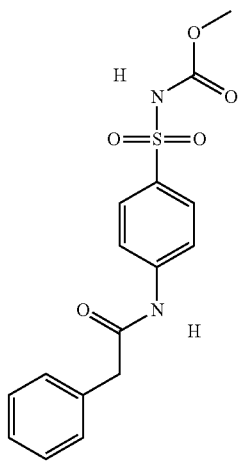
57
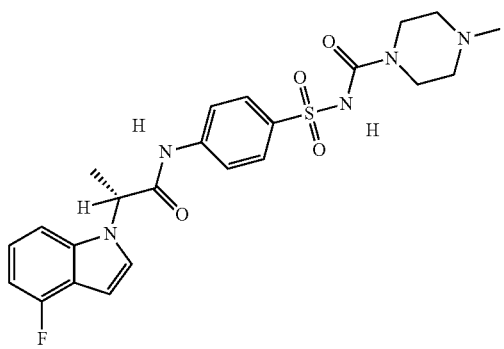
58
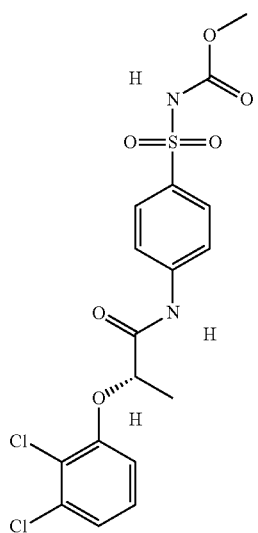
-continued
59
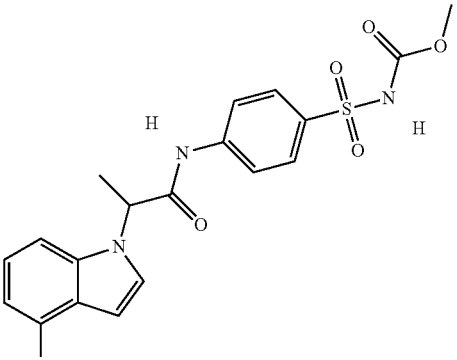
60
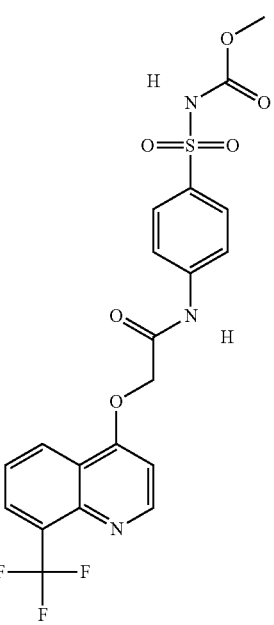
61
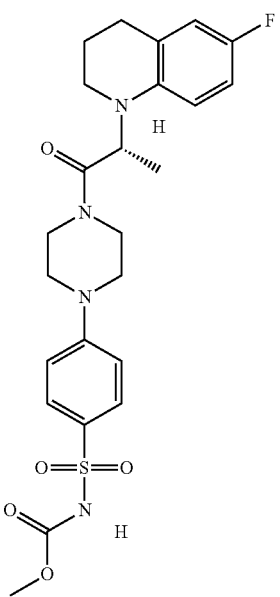

125
-continued
| | |
|---|---|
| 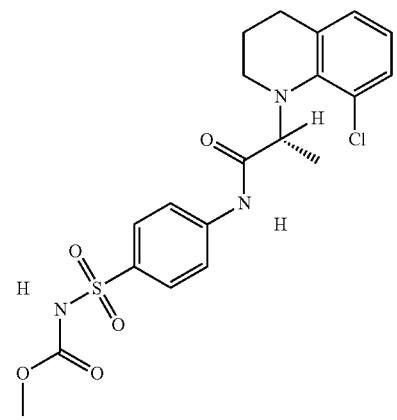 62 | 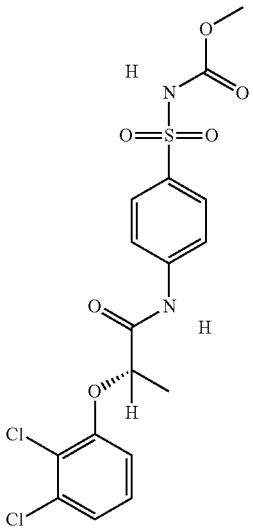 65 |
| 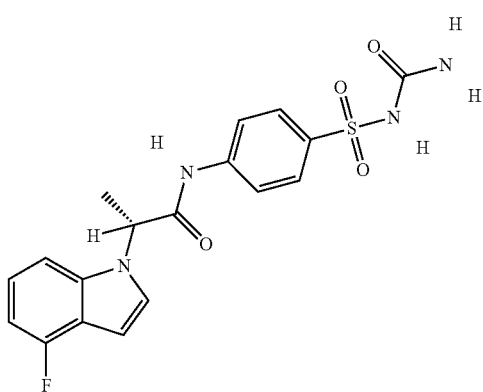 63 | 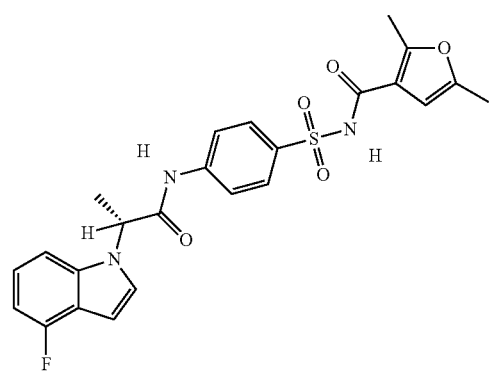 66 |
| 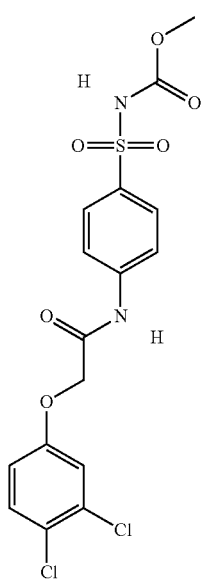 64 | 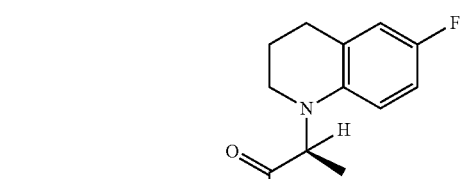 67 |
| | 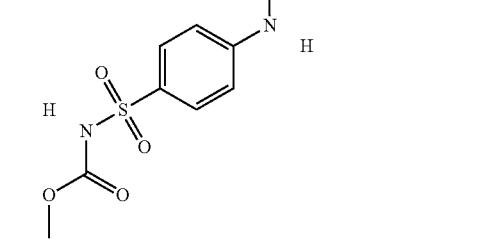 |
| | 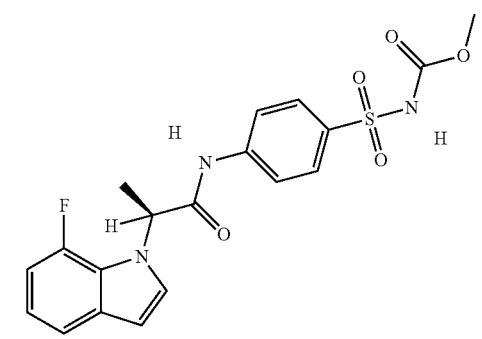 68 |
126
-continued

| 69 | 72 |
|---|---|
| 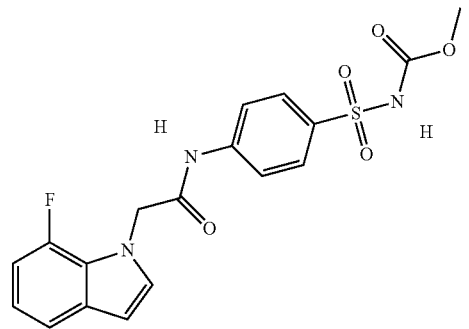 | 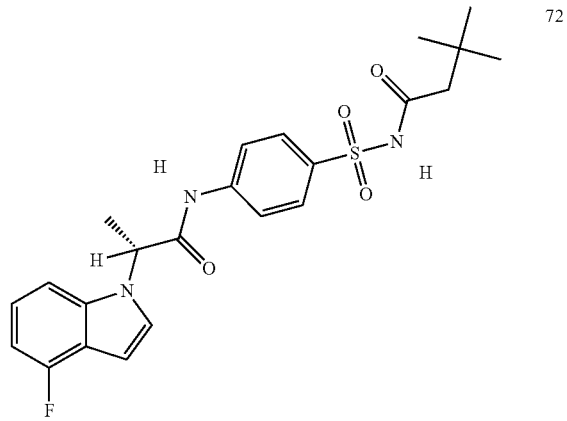 |
| 70 | 73 |
| 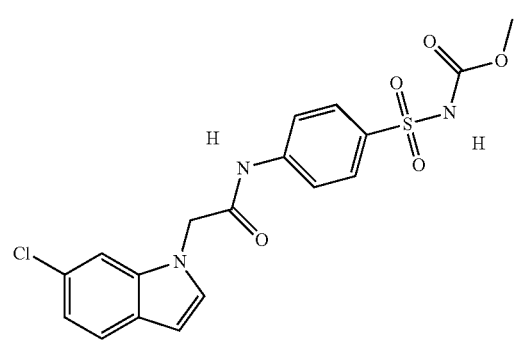 | 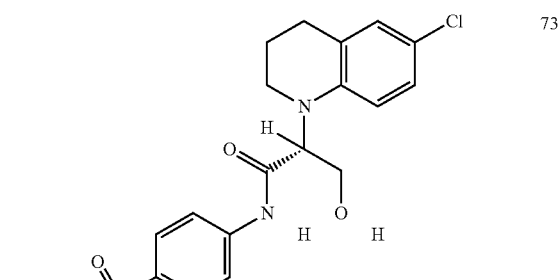 |
| 71 | 74 |
| 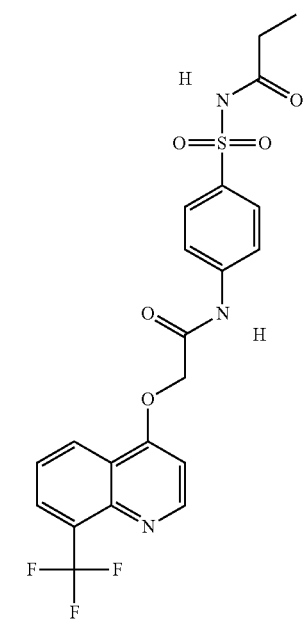 | 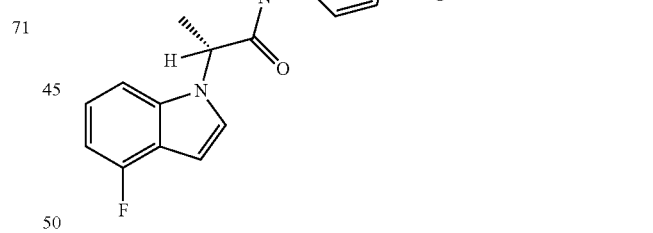 |
|  | 75 |
|  | 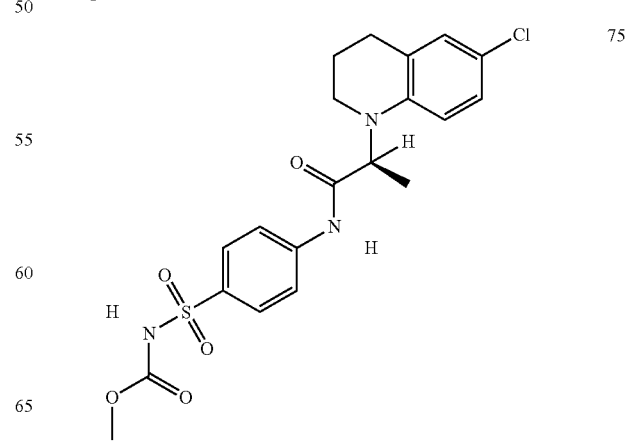 |

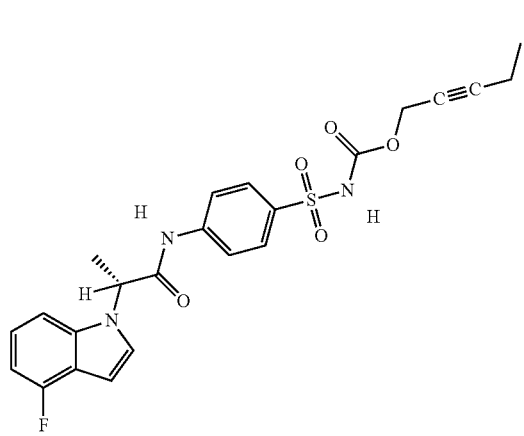
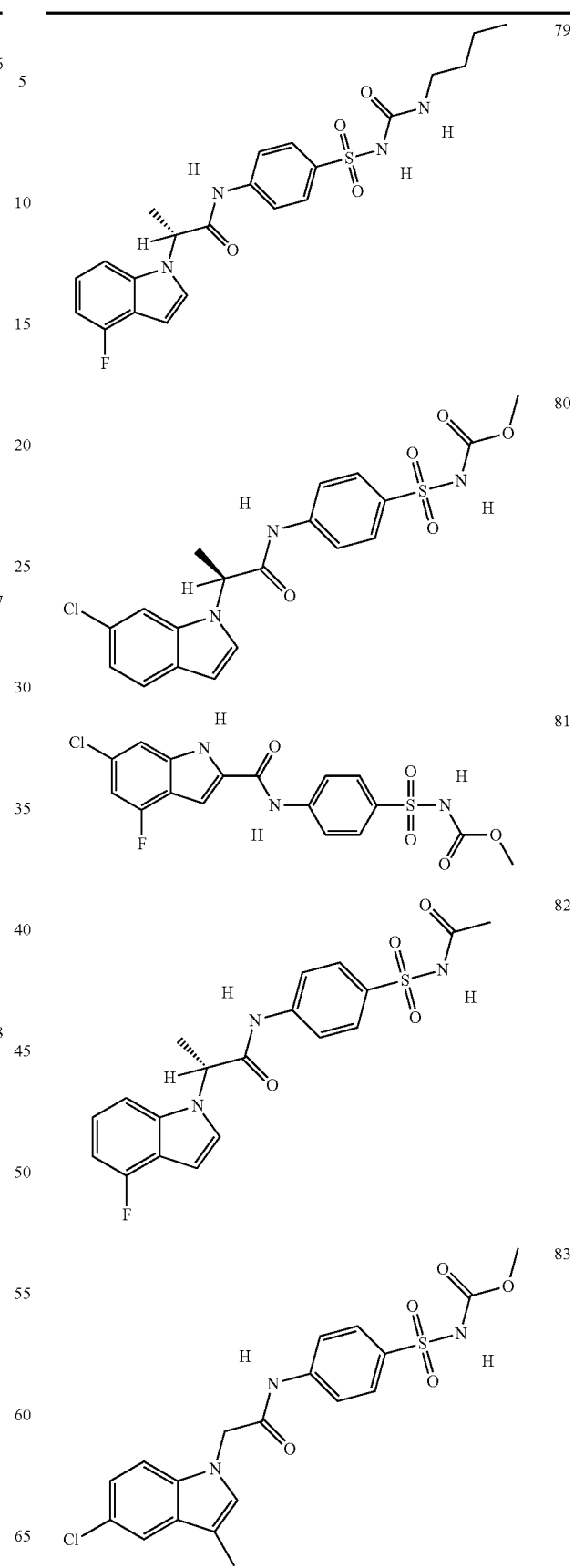

131
-continued
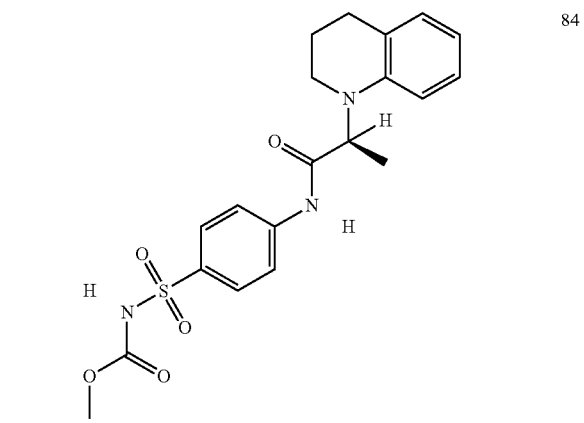
84
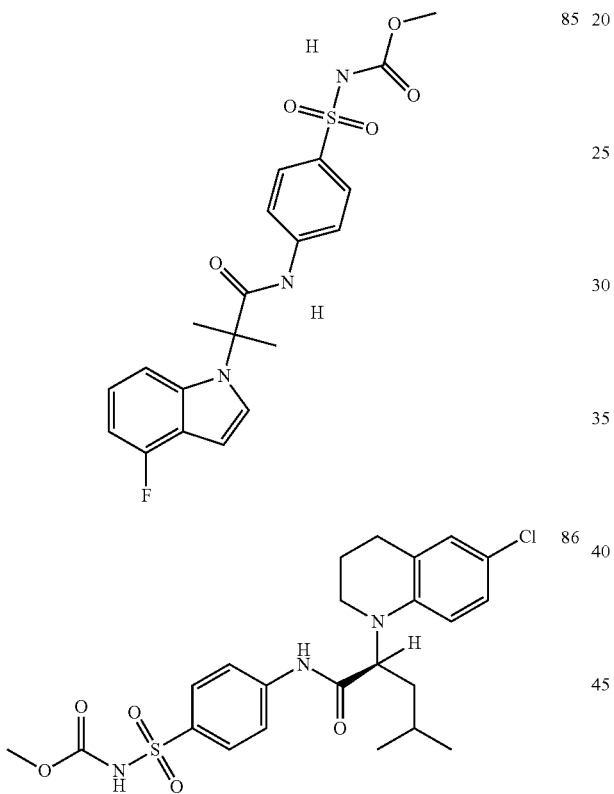
85
86
132
-continued
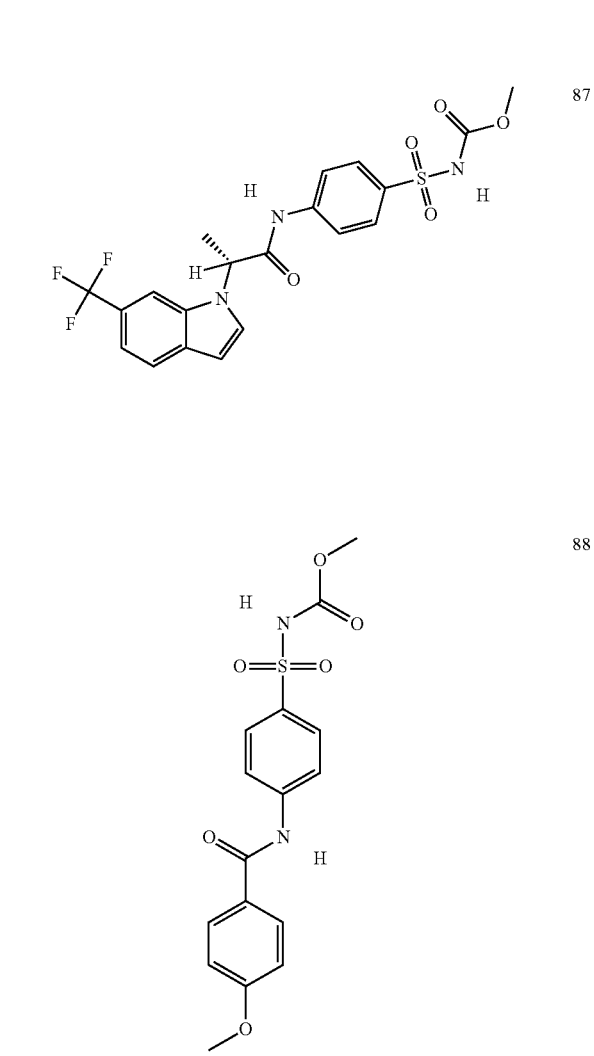
87
88
* * * * *